United States Patent
Geller et al.

(10) Patent No.: US 11,293,024 B2
(45) Date of Patent: Apr. 5, 2022

(54) ANTISENSE ANTIBACTERIAL COMPOUNDS AND METHODS

(71) Applicants: Oregon State University, Corvallis, OR (US); Board of Regents, The University of Texas System, Austin, TX (US)

(72) Inventors: Bruce L. Geller, Corvallis, OR (US); David Greenberg, Coppell, TX (US)

(73) Assignees: Board of Regents, The University of Texas System, Austin, TX (US); Oregon State University, Corvallis, OR (US)

(*) Notice: Subject to any disclaimer, the term of this patent is extended or adjusted under 35 U.S.C. 154(b) by 0 days.

(21) Appl. No.: 15/540,387

(22) PCT Filed: Dec. 23, 2015

(86) PCT No.: PCT/US2015/000280
§ 371 (c)(1),
(2) Date: Jun. 28, 2017

(87) PCT Pub. No.: WO2016/108930
PCT Pub. Date: Jul. 7, 2016

(65) Prior Publication Data
US 2019/0169609 A1    Jun. 6, 2019

Related U.S. Application Data

(60) Provisional application No. 62/098,713, filed on Dec. 31, 2014.

(51) Int. Cl.
| | | |
|---|---|---|
| *C12N 15/11* | (2006.01) | |
| *C12N 15/113* | (2010.01) | |
| *A61K 31/7088* | (2006.01) | |
| *A61K 38/12* | (2006.01) | |
| *A61P 31/04* | (2006.01) | |
| *C07F 9/6558* | (2006.01) | |
| *C07K 19/00* | (2006.01) | |

(52) U.S. Cl.
CPC ...... *C12N 15/113* (2013.01); *A61K 31/7088* (2013.01); *A61K 38/12* (2013.01); *A61P 31/04* (2018.01); *C07F 9/65583* (2013.01); *C07K 19/00* (2013.01); *C12N 2310/11* (2013.01); *C12N 2310/3233* (2013.01); *C12N 2320/31* (2013.01)

(58) Field of Classification Search
CPC .............. C12N 15/113; C12N 2310/11; C12N 2310/3233; A61P 31/04
See application file for complete search history.

(56) References Cited

U.S. PATENT DOCUMENTS

| | | | |
|---|---|---|---|
| 5,034,506 | A | 7/1991 | Summerton et al. |
| 5,142,047 | A | 8/1992 | Summerton et al. |
| 5,166,315 | A | 11/1992 | Summerton et al. |
| 5,185,444 | A | 2/1993 | Summerton et al. |
| 5,217,866 | A | 6/1993 | Summerton et al. |
| 5,506,337 | A | 4/1996 | Summerton et al. |
| 5,521,063 | A | 5/1996 | Summerton et al. |
| 5,698,685 | A | 12/1997 | Summerton et al. |
| 6,245,747 | B1 | 6/2001 | Porter et al. |
| 6,444,804 | B1 | 9/2002 | Lam et al. |
| 6,965,025 | B2 | 11/2005 | Gaarde et al. |
| 6,969,400 | B2 | 11/2005 | Rhee et al. |
| 7,625,873 | B2 | 12/2009 | Geller et al. |
| 7,790,694 | B2 | 9/2010 | Geller et al. |
| 8,067,571 | B2 | 11/2011 | Weller et al. |
| 8,076,476 | B2 | 12/2011 | Reeves et al. |
| 8,299,206 | B2 | 10/2012 | Fox et al. |
| 8,314,072 | B2 | 11/2012 | Geller et al. |
| 8,536,147 | B2 | 9/2013 | Weller et al. |
| 9,249,243 | B2 | 2/2016 | Weller et al. |
| 9,790,495 | B2 | 10/2017 | Geller et al. |
| 2004/0029129 | A1 | 2/2004 | Wang et al. |
| 2004/0033972 | A1 | 2/2004 | Horwitz et al. |
| 2005/0288246 | A1 | 12/2005 | Iversen et al. |
| 2006/0241075 | A1 | 10/2006 | McSwiggen |
| 2006/0270621 | A1 | 11/2006 | Christiano |
| 2007/0049542 | A1 | 3/2007 | Geller et al. |
| 2008/0194463 | A1 | 8/2008 | Weller et al. |
| 2010/0016215 | A1 | 1/2010 | Moulton et al. |
| 2010/0234281 | A1 | 9/2010 | Weller et al. |
| 2010/0261777 | A1 | 10/2010 | Shaw et al. |

(Continued)

FOREIGN PATENT DOCUMENTS

| | | |
|---|---|---|
| JP | 56-068616 | 6/1981 |
| KR | 10-2013-0005208 A | 1/2013 |

(Continued)

OTHER PUBLICATIONS

EP 15792493.7, Partial Supplementary European Search Report dated Nov. 29, 2017, 10 pages.
EP 15795398.5, Partial Supplementary European Search Report dated Nov. 29, 2017, 7 pages.
Greenberg, et al., "Antisense Phosphorodiamidate Morpholino Oligomers Targeted to an Essential Gene Inhibit Burkholderia cepacia Complex." The Journal of Infectious Diseases (2010); 12: 1822-1830.

(Continued)

*Primary Examiner* — Ekaterina Poliakova-Georgantas
(74) *Attorney, Agent, or Firm* — Parker Highlander PLLC

(57) ABSTRACT

Provided are antisense oligonucleotides targeted against bacterial genes involved in biochemical pathways and/or cellular processes, and related compositions and methods of using the oligonucleotides and compositions, alone or in combination with other antimicrobial agents, for instance, in the treatment of an infected mammalian subject.

7 Claims, 22 Drawing Sheets
Specification includes a Sequence Listing.

(56) References Cited

U.S. PATENT DOCUMENTS

| | | |
|---|---|---|
| 2012/0040460 A1 | 2/2012 | Rigoutsos et al. |
| 2012/0122769 A1 | 5/2012 | Iversen |
| 2012/0213663 A1 | 8/2012 | Atieh et al. |
| 2012/0289457 A1 | 11/2012 | Hanson |
| 2012/0296087 A1 | 11/2012 | Sinha et al. |
| 2013/0197220 A1 | 8/2013 | Ueda |
| 2013/0288369 A1 | 10/2013 | Iverson |
| 2015/0141321 A1 | 5/2015 | Kole et al. |
| 2015/0361425 A1 | 12/2015 | Geller et al. |
| 2016/0106857 A1 | 4/2016 | Geller et al. |

FOREIGN PATENT DOCUMENTS

| | | | | |
|---|---|---|---|---|
| KR | 10-2014-0010475 | | 1/2014 | |
| WO | WO 1993/001286 A2 | | 1/1993 | |
| WO | WO-0015265 A1 | * | 3/2000 | ........... C12N 15/113 |
| WO | WO 2004/097017 A2 | | 11/2004 | |
| WO | WO 2006/085973 A2 | | 8/2006 | |
| WO | WO 2007/009094 A2 | | 1/2007 | |
| WO | WO 2008/008113 A1 | | 1/2008 | |
| WO | WO 2009/005793 A2 | | 1/2009 | |
| WO | WO 2009/064471 A1 | | 5/2009 | |
| WO | WO 2009/139635 | | 11/2009 | |
| WO | WO 2012/043730 A1 | | 4/2012 | |
| WO | WO 2012/064991 A1 | | 5/2012 | |
| WO | WO 2012/150960 A1 | | 11/2012 | |
| WO | WO 2013/011072 A1 | | 1/2013 | |
| WO | WO 2013/074834 | | 5/2013 | |
| WO | WO 2015/175977 A2 | | 11/2015 | |
| WO | WO 2015/179249 A1 | | 11/2015 | |
| WO | WO 2016/108930 A2 | | 7/2016 | |
| WO | WO 2017/112885 A1 | | 6/2017 | |
| WO | WO 2017/112888 A1 | | 6/2017 | |

OTHER PUBLICATIONS

GenBank 01251363 [KR 1020130005208-A/39: Method and kit for detecting carbapenem resistant enterobacteriaceae using real-time PCR] (retrieved on Oct. 13, 2015 from http://www.ncbi.nlm.nih.gov/nucleotide/662699238?report=genbank&log$=nuclalign&blast_rank=1&RID=1V403DGD016] Jul. 8, 2014 (Jul. 8, 2014) whole doc.
Summerton et al. 1997, "Morpholino antisense oligomers: design, preparation, and properties." Antisense and Nucleic Acid Drug Development (1997); 7.3: 187-195.
Youngblood, Derek S., et al. "Stability of cell-penetrating peptide-morpholino oligomer conjugates in human serum and in cells." Bioconjugate Chemistry (2007); 18.1: 50-60.
PCT/US2015/031150, International Search Report and Written Opinion dated Jan. 14, 2016.
PCT/US2015/031150, International Preliminary Report on Patentability dated Nov. 22, 2016, 11 pages.
PCT/US2015/031213, International Search Report and Written Opinion dated Sep. 2, 2015.
PCT/US2015/031213, International Preliminary Report on Patentability dated Nov. 22, 2016, 7 pages.
PCT/US2015/000280, International Search Report and Written Opinion dated May 2, 2016.
PCT/US2015/000280, International Preliminary Report on Patentability dated Jul. 4, 2017, 6 pages.
PCT/US2016/068373, International Search Report and Written Opinion dated May 4, 2017, 17 pages.
PCT/US2016/068376, International Search Report and Written Opinion dated Mar. 13, 2017, 11 pages.
Howard et al., "Inhibition of pseudomonas aeruginosa by peptide-conjugated phosphorodiamidate morpholine oligomers," *Antimicrobial Agents and Chemotherapy*, 61(4):e01938, 2017.
Partial Supplementary European Search Report issued in European Application No. 15875820.1, dated Jun. 28, 2018.
Wu et al., "Cell-penetrating peptides as transporters for morpholino oligomers: effects of amino acid composition on intracellular delivery and cytotoxicity," *Nucleic Acids Research*, 35(15):5182-5191, 2007.
Azzolina et al., "The cell wall and cell division gene cluster in the Mra operon of Pseudomonas aeruginosa: cloning, production, and purification of active enzymes," *Protein Expression and Purificatio*, 21(3):393-400, 2001.
Barbier et al., "From the environment to the host: re-wiring of the transcriptome of Pseudomonas aeruginosa from 22° C. to 37° C.," *PLoS One*, 9(2):e89941, 2014.
El Zoeiby et al., "Identification of novel inhibitors of Pseudomonas aeruginosa MurC enzyme derived from phage-displayed peptide libraries," *Journal of Antimicrobial Chemotherapy*, 51(3):531-543, 2003.
Kong et al., "Pseudomonas aeruginosa AmpR is a global transcriptional factor that regulates expression of AmpC and PoxB beta-lactamases, proteases, quorum sensing, and other virulence factors," *Antimicrobial Agents and Chemotherapy*, 49(11):4567-4575, 2005.
Lam et al., "Genetic and Functional Diversity of Pseudomonas aeruginosa Lipopolysaccharide," *Frontiers in Microbiology*, 2(118):1-25, 2011.
Tchufistova et al., "A key role for the mRNA leader structure in translational control of ribosomal protein S1 synthesis in gamma-proteobacteria," *Nucleic Acids Research*, 31(23):6996-7002, 2003.
Tielen et al., "Regulatory and metabolic networks for the adaptation of Pseudomonas aeruginosa biofilms to urinary tract-like conditions," *PLoS One*, 8(8):e71845, 2013.
Tsubery et al., "Structure-function studies of polymyxin B nonapeptide: implications to sensitization of gram-negative bacteria," *J. Med. Chem.*, 43(16):3085-3092, 2000.
Ghosal and Nielsen, "Potent antibacterial antisense peptide-peptide nucleic acid conjugates against *Pseudomonas aeruginosa*," *Nucleic Acid Therapeutics*, 22(5):323-334.

* cited by examiner

| Strain ID | Species | RpsJ-PPMO#13 | WaaA-PPMO#15 | RpsJ-PPMO#26 | MurC-PPMO#8 | AccA-PPMO#9 | FabZ-PPMO#20 | MurB-PPMO#17 | WaaC-PPMO#6 | WaaF-PPMO#16 |
|---|---|---|---|---|---|---|---|---|---|---|
| W40423 | P. aeruginosa | 2 | >16 | 16 | 8 | >16 | >16 | >16 | >16 | >16 |
| M57-15 | P. aeruginosa | >16 | 16 | 16 | >16 | 16 | >16 | >16 | >16 | >16 |
| H25815 | P. aeruginosa | 8 | >16 | 4 | >16 | >16 | >16 | >16 | >16 | >16 |
| M69781 | P. aeruginosa | 4 | 8 | 4 | >16 | 16 | >16 | >16 | >16 | >16 |
| T63621 | P. aeruginosa | >16 | >16 | >16 | >16 | >16 | >16 | >16 | >16 | >16 |
| W41033 | P. aeruginosa | >16 | >16 | >16 | >16 | >16 | >16 | >16 | >16 | >16 |
| W43532 | P. aeruginosa | >16 | >16 | >16 | >16 | >16 | >16 | >16 | >16 | >16 |
| O1 | P. aeruginosa | >16 | >16 | 16 | NT | >16 | >16 | >16 | >16 | >16 |
| H28822 | P. aeruginosa | >16 | >16 | >16 | NT | >16 | >16 | >16 | >16 | >16 |
| PPMO IC$_{50}$ [μM] | | >16 | >16 | >16 | >16 | >16 | >16 | >16 | >16 | >16 |

Key:
- NT: Not Tested
- >16: >16 μM
- 16: 16 μM
- 8: 8 μM
- 4: 4 μM
- 2: 2 μM
- 1: 1 μM
- 0.5: 0.5 μM

| Strain ID | Species | WaaG-PPMO#12 | LpxA-PPMO#10 | LpxB-PPMO#11 | MurF-PPMO#21 | MurG-PPMO#22 | RpsJ-PPMO#23 | Media only PPMO#27 | Scr-PPMO#41 |
|---|---|---|---|---|---|---|---|---|---|
| W40423 | P. aeruginosa | >16 | >16 | >16 | >16 | >16 | >16 | >16 | >16 |
| M57-15 | P. aeruginosa | >16 | >16 | >16 | >16 | >16 | >16 | >16 | >16 |
| H25815 | P. aeruginosa | >16 | >16 | >16 | >16 | >16 | >16 | >16 | >16 |
| M69781 | P. aeruginosa | >16 | >16 | >16 | >16 | >16 | >16 | >16 | >16 |
| T63621 | P. aeruginosa | >16 | >16 | >16 | >16 | >16 | >16 | >16 | >16 |
| W41033 | P. aeruginosa | >16 | >16 | >16 | >16 | >16 | >16 | >16 | >16 |
| W43532 | P. aeruginosa | >16 | >16 | >16 | >16 | >16 | >16 | >16 | >16 |
| O1 | P. aeruginosa | >16 | >16 | >16 | >16 | >16 | >16 | >16 | >16 |
| H28822 | P. aeruginosa | >16 | >16 | >16 | >16 | >16 | >16 | >16 | >16 |
| PPMO IC$_{50}$ [μM] | | >16 | >16 | >16 | >16 | >16 | >16 | | >16 |

Key: NT = Not Tested; >16 μM; 16 μM; 8 μM; 4 μM; 2 μM; 1 μM; 0.5 μM

| Strain ID | Species | Scr-PPMO#43 | Scr-PPMO#44 | Scr-PPMO#45 | Scr-PPMO#46 |
|---|---|---|---|---|---|
| W40423 | P. aeruginosa | >16 | >16 | >16 | >16 |
| M57-15 | P. aeruginosa | >16 | >16 | >16 | >16 |
| H25815 | P. aeruginosa | >16 | >16 | >16 | >16 |
| M69781 | P. aeruginosa | >16 | >16 | >16 | >16 |
| T63621 | P. aeruginosa | >16 | >16 | >16 | >16 |
| W41033 | P. aeruginosa | >16 | >16 | >16 | >16 |
| W43532 | P. aeruginosa | >16 | >16 | >16 | >16 |
| O1 | P. aeruginosa | >16 | >16 | >16 | >16 |
| H28822 | P. aeruginosa | >16 | >16 | >16 | >16 |
| PPMO IC$_{50}$ [μM] | | >16 | >16 | >16 | >16 |

| Key | |
|---|---|
| NT | Not Tested |
| >16 | >16 μM |
| 16 | 16 μM |
| 8 | 8 μM |
| 4 | 4 μM |
| 2 | 2 μM |
| 1 | 1 μM |
| 0.5 | 0.5 μM |

FIG. 4C (Continued)

SEQUENCE LISTING

<160> NUMBER OF SEQ ID NOS: 37

<210> SEQ ID NO 1
<211> LENGTH: 11
<212> TYPE: DNA
<213> ORGANISM: Pseudomonas aeruginosa

<400> SEQUENCE: 1
cctcagactc c                                                          11

<210> SEQ ID NO 2
<211> LENGTH: 11
<212> TYPE: DNA
<213> ORGANISM: Pseudomonas aeruginosa

<400> SEQUENCE: 2
gttgtttgat c                                                          11

<210> SEQ ID NO 3
<211> LENGTH: 11
<212> TYPE: DNA
<213> ORGANISM: Pseudomonas aeruginosa

<400> SEQUENCE: 3
ttctctcctt t                                                          11

<210> SEQ ID NO 4
<211> LENGTH: 11
<212> TYPE: DNA
<213> ORGANISM: Pseudomonas aeruginosa

<400> SEQUENCE: 4
cataccttgt t                                                          11

<210> SEQ ID NO 5
<211> LENGTH: 11
<212> TYPE: DNA
<213> ORGANISM: Pseudomonas aeruginosa

<400> SEQUENCE: 5
ctctagacat g                                                          11

<210> SEQ ID NO 6
<211> LENGTH: 11
<212> TYPE: DNA
<213> ORGANISM: Pseudomonas aeruginosa

<400> SEQUENCE: 6
agcaccctca t                                                          11

<210> SEQ ID NO 7
<211> LENGTH: 11
<212> TYPE: DNA
<213> ORGANISM: Pseudomonas aeruginosa

<400> SEQUENCE: 7
tgactctcct c                                                          11

<210> SEQ ID NO 8
<211> LENGTH: 11
<212> TYPE: DNA
<213> ORGANISM: Pseudomonas aeruginosa

<400> SEQUENCE: 8

-continued

| ccacctccag g | 11 |

<210> SEQ ID NO 9
<211> LENGTH: 11
<212> TYPE: DNA
<213> ORGANISM: Pseudomonas aeruginosa

<400> SEQUENCE: 9

| aggcttccgt c | 11 |

<210> SEQ ID NO 10
<211> LENGTH: 11
<212> TYPE: DNA
<213> ORGANISM: Pseudomonas aeruginosa

<400> SEQUENCE: 10

| atcaaactca t | 11 |

<210> SEQ ID NO 11
<211> LENGTH: 11
<212> TYPE: DNA
<213> ORGANISM: Pseudomonas aeruginosa

<400> SEQUENCE: 11

| taatccgtca g | 11 |

<210> SEQ ID NO 12
<211> LENGTH: 11
<212> TYPE: DNA
<213> ORGANISM: Pseudomonas aeruginosa

<400> SEQUENCE: 12

| gccagggtca t | 11 |

<210> SEQ ID NO 13
<211> LENGTH: 11
<212> TYPE: DNA
<213> ORGANISM: Pseudomonas aeruginosa

<400> SEQUENCE: 13

| gcatttgacc t | 11 |

<210> SEQ ID NO 14
<211> LENGTH: 11
<212> TYPE: DNA
<213> ORGANISM: Pseudomonas aeruginosa

<400> SEQUENCE: 14

| gtacggttca t | 11 |

<210> SEQ ID NO 15
<211> LENGTH: 11
<212> TYPE: DNA
<213> ORGANISM: Pseudomonas aeruginosa

<400> SEQUENCE: 15

| agaattctca t | 11 |

<210> SEQ ID NO 16
<211> LENGTH: 11
<212> TYPE: DNA
<213> ORGANISM: Pseudomonas aeruginosa

```
<400> SEQUENCE: 16
cagtcgcccc t                                                      11

<210> SEQ ID NO 17
<211> LENGTH: 11
<212> TYPE: DNA
<213> ORGANISM: Pseudomonas aeruginosa

<400> SEQUENCE: 17
aggctcatag g                                                      11

<210> SEQ ID NO 18
<211> LENGTH: 11
<212> TYPE: DNA
<213> ORGANISM: Pseudomonas aeruginosa

<400> SEQUENCE: 18
ctagcactcc c                                                      11

<210> SEQ ID NO 19
<211> LENGTH: 11
<212> TYPE: DNA
<213> ORGANISM: Pseudomonas aeruginosa

<400> SEQUENCE: 19
atgtccatca t                                                      11

<210> SEQ ID NO 20
<211> LENGTH: 11
<212> TYPE: DNA
<213> ORGANISM: Pseudomonas aeruginosa

<400> SEQUENCE: 20
acctcccagg c                                                      11

<210> SEQ ID NO 21
<211> LENGTH: 11
<212> TYPE: DNA
<213> ORGANISM: Pseudomonas aeruginosa

<400> SEQUENCE: 21
gcaaagtcct c                                                      11

<210> SEQ ID NO 22
<211> LENGTH: 11
<212> TYPE: DNA
<213> ORGANISM: Pseudomonas aeruginosa

<400> SEQUENCE: 22
gtcgaaccaa t                                                      11

<210> SEQ ID NO 23
<211> LENGTH: 12
<212> TYPE: PRT
<213> ORGANISM: Artificial Sequence
<220> FEATURE:
<223> OTHER INFORMATION: (RXR)4- cell-penetrating peptide
<220> FEATURE:
<221> NAME/KEY: misc_feature
<222> LOCATION: (2)..(2)
<223> OTHER INFORMATION: Xaa may be 6-aminohexanoic acid
<220> FEATURE:
<221> NAME/KEY: misc_feature
<222> LOCATION: (5)..(5)
<223> OTHER INFORMATION: Xaa may be 6-aminohexanoic acid
```

```
<220> FEATURE:
<221> NAME/KEY: misc_feature
<222> LOCATION: (8)..(8)
<223> OTHER INFORMATION: Xaa may be 6-aminohexanoic acid
<220> FEATURE:
<221> NAME/KEY: misc_feature
<222> LOCATION: (11)..(11)
<223> OTHER INFORMATION: Xaa may be 6-aminohexanoic acid

<400> SEQUENCE: 23

Arg Xaa Arg Arg Xaa Arg Arg Xaa Arg Arg Xaa Arg
1               5                   10

<210> SEQ ID NO 24
<211> LENGTH: 12
<212> TYPE: PRT
<213> ORGANISM: Artificial Sequence
<220> FEATURE:
<223> OTHER INFORMATION: (RXRRBR)2- cell-penetrating peptide
<220> FEATURE:
<221> NAME/KEY: misc_feature
<222> LOCATION: (2)..(2)
<223> OTHER INFORMATION: Xaa may be 6-aminohexanoic acid
<220> FEATURE:
<221> NAME/KEY: misc_feature
<222> LOCATION: (5)..(5)
<223> OTHER INFORMATION: Xaa may be beta-alanine
<220> FEATURE:
<221> NAME/KEY: misc_feature
<222> LOCATION: (8)..(8)
<223> OTHER INFORMATION: Xaa may be 6-aminohexanoic acid
<220> FEATURE:
<221> NAME/KEY: misc_feature
<222> LOCATION: (11)..(11)
<223> OTHER INFORMATION: Xaa may be beta-alanine

<400> SEQUENCE: 24

Arg Xaa Arg Arg Xaa Arg Arg Xaa Arg Arg Xaa Arg
1               5                   10

<210> SEQ ID NO 25
<211> LENGTH: 6
<212> TYPE: PRT
<213> ORGANISM: Artificial Sequence
<220> FEATURE:
<223> OTHER INFORMATION: R6- cell-penetrating peptide

<400> SEQUENCE: 25

Arg Arg Arg Arg Arg Arg
1               5

<210> SEQ ID NO 26
<211> LENGTH: 10
<212> TYPE: PRT
<213> ORGANISM: Artificial Sequence
<220> FEATURE:
<223> OTHER INFORMATION: (RFF)3R- cell-penetrating peptide

<400> SEQUENCE: 26

Arg Phe Phe Arg Phe Phe Arg Phe Phe Arg
1               5                   10

<210> SEQ ID NO 27
<211> LENGTH: 12
<212> TYPE: PRT
<213> ORGANISM: Artificial Sequence
<220> FEATURE:
<223> OTHER INFORMATION: (RYR)4- cell-penetrating peptide

<400> SEQUENCE: 27
```

```
Arg Tyr Arg Arg Tyr Arg Arg Tyr Arg Arg Tyr Arg
1               5                   10

<210> SEQ ID NO 28
<211> LENGTH: 12
<212> TYPE: PRT
<213> ORGANISM: Artificial Sequence
<220> FEATURE:
<223> OTHER INFORMATION: (RFR)4- cell-penetrating peptide

<400> SEQUENCE: 28

Arg Phe Arg Arg Phe Arg Arg Phe Arg Arg Phe Arg
1               5                   10

<210> SEQ ID NO 29
<211> LENGTH: 12
<212> TYPE: PRT
<213> ORGANISM: Artificial Sequence
<220> FEATURE:
<223> OTHER INFORMATION: (RGR)4- cell-penetrating peptide

<400> SEQUENCE: 29

Arg Gly Arg Arg Gly Arg Arg Gly Arg Arg Gly Arg
1               5                   10

<210> SEQ ID NO 30
<211> LENGTH: 9
<212> TYPE: PRT
<213> ORGANISM: Artificial Sequence
<220> FEATURE:
<223> OTHER INFORMATION: (dRdFdF)3- cell-penetrating peptide
<220> FEATURE:
<221> NAME/KEY: misc_feature
<222> LOCATION: (1)..(9)
<223> OTHER INFORMATION: Residues may be d seteroisomer forms of the
      amino acids

<400> SEQUENCE: 30

Arg Phe Phe Arg Phe Phe Arg Phe Phe
1               5

<210> SEQ ID NO 31
<211> LENGTH: 12
<212> TYPE: PRT
<213> ORGANISM: Artificial Sequence
<220> FEATURE:
<223> OTHER INFORMATION: (dRXdR)4- cell-penetrating peptide
<220> FEATURE:
<221> NAME/KEY: misc_feature
<222> LOCATION: (1)..(1)
<223> OTHER INFORMATION: Residues may be d seteroisomer forms of the
      amino acids
<220> FEATURE:
<221> NAME/KEY: misc_feature
<222> LOCATION: (2)..(2)
<223> OTHER INFORMATION: Xaa may be 6-aminohexanoic acid
<220> FEATURE:
<221> NAME/KEY: misc_feature
<222> LOCATION: (3)..(4)
<223> OTHER INFORMATION: Residues may be d seteroisomer forms of the
      amino acids
<220> FEATURE:
<221> NAME/KEY: misc_feature
<222> LOCATION: (5)..(5)
<223> OTHER INFORMATION: Xaa may be 6-aminohexanoic acid
<220> FEATURE:
<221> NAME/KEY: misc_feature
<222> LOCATION: (6)..(7)
<223> OTHER INFORMATION: Residues may be d seteroisomer forms of the
      amino acids
<220> FEATURE:
<221> NAME/KEY: misc_feature
```

```
<222> LOCATION: (8)..(8)
<223> OTHER INFORMATION: Xaa may be 6-aminohexanoic acid
<220> FEATURE:
<221> NAME/KEY: misc_feature
<222> LOCATION: (9)..(10)
<223> OTHER INFORMATION: Residues may be d seteroisomer forms of the
      amino acids
<220> FEATURE:
<221> NAME/KEY: misc_feature
<222> LOCATION: (11)..(11)
<223> OTHER INFORMATION: Xaa may be 6-aminohexanoic acid
<220> FEATURE:
<221> NAME/KEY: misc_feature
<222> LOCATION: (12)..(12)
<223> OTHER INFORMATION: Residues may be d seteroisomer forms of the
      amino acids

<400> SEQUENCE: 31

Arg Xaa Arg Arg Xaa Arg Arg Xaa Arg Arg Xaa Arg
1               5                   10

<210> SEQ ID NO 32
<211> LENGTH: 8
<212> TYPE: PRT
<213> ORGANISM: Artificial Sequence
<220> FEATURE:
<223> OTHER INFORMATION: dR8- cell-penetrating peptide
<220> FEATURE:
<221> NAME/KEY: misc_feature
<222> LOCATION: (1)..(8)
<223> OTHER INFORMATION: Residues may be d seteroisomer forms of the
      amino acids

<400> SEQUENCE: 32

Arg Arg Arg Arg Arg Arg Arg Arg
1               5

<210> SEQ ID NO 33
<211> LENGTH: 6
<212> TYPE: PRT
<213> ORGANISM: Artificial Sequence
<220> FEATURE:
<223> OTHER INFORMATION: dR6- cell-penetrating peptide
<220> FEATURE:
<221> NAME/KEY: misc_feature
<222> LOCATION: (1)..(6)
<223> OTHER INFORMATION: Residues may be d seteroisomer forms of the
      amino acids

<400> SEQUENCE: 33

Arg Arg Arg Arg Arg Arg
1               5

<210> SEQ ID NO 34
<211> LENGTH: 10
<212> TYPE: PRT
<213> ORGANISM: Artificial Sequence
<220> FEATURE:
<223> OTHER INFORMATION: (dRdFdF)3dR- cell-penetrating peptide
<220> FEATURE:
<221> NAME/KEY: misc_feature
<222> LOCATION: (1)..(10)
<223> OTHER INFORMATION: Residues may be d seteroisomer forms of the
      amino acids

<400> SEQUENCE: 34

Arg Phe Phe Arg Phe Phe Arg Phe Phe Arg
1               5                   10

<210> SEQ ID NO 35
<211> LENGTH: 11
```

```
<212> TYPE: DNA
<213> ORGANISM: Pseudomonas aeruginosa

<400> SEQUENCE: 35
ctcatacctt g                                                          11

<210> SEQ ID NO 36
<211> LENGTH: 11
<212> TYPE: DNA
<213> ORGANISM: Artificial Sequence
<220> FEATURE:
<223> OTHER INFORMATION: scrambled targeting sequence

<400> SEQUENCE: 36
tctcagatgg t                                                          11

<210> SEQ ID NO 37
<211> LENGTH: 11
<212> TYPE: DNA
<213> ORGANISM: Artificial Sequence
<220> FEATURE:
<223> OTHER INFORMATION: scrambled targeting sequence

<400> SEQUENCE: 37
atcgttgcat c                                                          11
```

ANTISENSE ANTIBACTERIAL COMPOUNDS AND METHODS

CROSS-REFERENCE TO RELATED APPLICATIONS

This application claims priority under 35 U.S.C. § 119(e) to U.S. Application No. 62/098,713, filed Dec. 31, 2014, which is incorporated by reference in its entirety.

STATEMENT REGARDING THE SEQUENCE LISTING

The Sequence Listing associated with this application is provided in text format in lieu of a paper copy, and is hereby incorporated by reference into the specification. The name of the text file containing the Sequence Listing is SATH_005_01WO_SeqList_ST25.txt. The text file is about 9 KB, was created on Dec. 21, 2015, and is being submitted electronically via EFS-Web.

BACKGROUND

Technical Field

The present disclosure relates to antisense oligonucleotides targeted against bacterial genes involved in biochemical pathways and/or cellular processes, and related compositions and methods of using the oligonucleotides and compositions, alone or in combination with other antimicrobial agents, for instance, in the treatment of an infected mammalian subject.

Description of the Related Art

New paradigms in antimicrobial therapeutic development are urgently needed to fight the rapid increase in antibiotic resistance. This is particularly true for hosts that suffer from chronic infections, such as in those with cystic fibrosis (CF). CF patients suffer from chronic pulmonary infections with a variety of pathogens, including *Pseudomonas aeruginosa* and the *Burkholderia cepacia* complex (Bcc), both of which cause significant morbidity and mortality. Cystic fibrosis results from mutations in both alleles of the cystic fibrosis transmembrane conductance regulator (CFTR) gene. Chronic pulmonary infections occur with a variety of pathogens including *Pseudomonas aeruginosa, Staphylococcus aureus,* and *Burkholderia cepacia* complex (Bcc) and are a major cause of the morbidity and mortality in patients with CF. In addition, the proportion of patients harboring antibiotic resistant strains of these organisms is climbing. These pathogens can be impossible to eradicate from the lung and can lead to either progressive or rapid decline in lung function.

The current pipeline for new antimicrobials against these multidrug-resistant Gram-negative pathogens remains narrow. In addition, many drugs that have been developed involve modifying existing antibiotic scaffolds as opposed to radically new innovations in drug development. Thus, there is a need for antimicrobial agents that (i) are not subject to the principal types of antibiotic resistance currently hampering antibiotic treatment of bacterial infection, (ii) can be developed rapidly and with some reasonable degree of predictability as to target-bacteria specificity, (iii) are effective at low doses, and (iv) show few side effects. The current disclosure provides for antisense oligonucleotides that can be used alone or in combination with traditional antibiotics or other antimicrobial agents to target multidrug-resistant pathogens.

BRIEF SUMMARY OF THE DISCLOSURE

Embodiments of the present disclosure relate, in part, to the discovery that the antisense targeting of bacterial genes involved in biochemical pathways and/or cellular processes can, inter alia, increase the antibiotic susceptibility of otherwise antibiotic-resistant pathogenic bacteria, and reduce the ability of certain pathogenic bacteria to grow. For example, the antisense targeting of essential bacterial genes such as genes encoding ribosomal proteins and genes encoding proteins important for lipopolysaccharide biosynthesis was shown to increase the susceptibility of antibiotic resistant (e.g., multi-drug resistant) bacteria to antibiotics such as polymyxins and antimicrobial agents such as polymyxin nonapeptides, and could thus find utility in the treatment of such bacteria, for instance, in combination with antibiotics and/or antimicrobial agents. Such antisense targeting could find utility in standalone therapies against multi-drug resistant bacteria, and as combination therapies, for example, to increase the susceptibility of bacteria to antibiotics and/or antimicrobial agents. In addition, the antisense targeting of antibiotic resistance genes, such as genes encoding resistance to ampicillin, was shown to increase the susceptibility of ampicillin-resistant bacteria to ampicillin.

Embodiments of the present disclosure therefore include a substantially uncharged antisense morpholino oligonucleotide, composed of morpholino subunits and phosphorus-containing intersubunit linkages joining a morpholino nitrogen of one subunit to a 5'-exocyclic carbon of an adjacent subunit, and having (a) about 10-40 nucleotide bases, and (b) a targeting sequence of sufficient length and complementarity to specifically hybridize to a bacterial mRNA target sequence that encodes a protein involved in a bacterial biochemical pathway and/or cellular process; where the oligonucleotide is conjugated to a cell-penetrating peptide (CPP).

In certain embodiments, the target sequence comprises a translational start codon of the bacterial mRNA and/or a sequence within about 30 bases upstream or downstream of the translational start codon of the bacterial mRNA.

In certain embodiments, the phosphorodiamidate morpholino oligonucleotide is a compound, or a pharmaceutically acceptable salt thereof, of formula I:

(I)

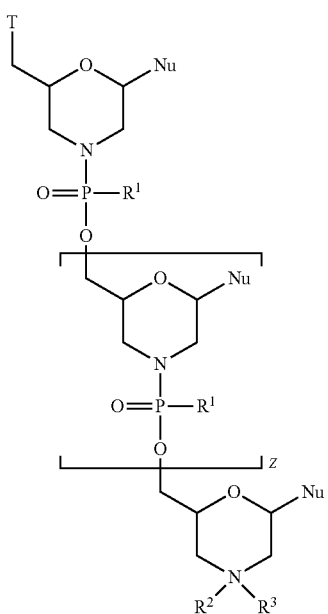

Where each Nu is a nucleobase which taken together forms a nucleobase sequence, Z is an integer from 8 to 38, T is selected from OH and a moiety of the formula:

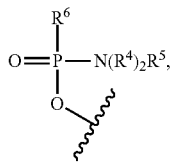

Where each $R^4$ is independently $C_1$-$C_6$ alkyl, and $R^5$ is selected from an electron pair and H, and $R^6$ is selected from —N($R^7$)CH$_2$C(O)NH$_2$, and a moiety of the formula:

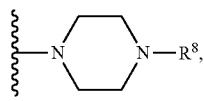

where $R^7$ is selected from H and $C_1$-$C_6$ alkyl, and $R^8$ is selected from G, —C(O)—$R^9$, acyl, trityl, and 4-methoxytrityl, where $R^9$ is of the formula —(O-alkyl)$_y$-OH wherein y is an integer from 3 to 10 and each of the y alkyl groups is independently selected from $C_2$-$C_6$ alkyl; where each instance of $R^1$ is —N($R^{10}$)$_2R^{11}$ wherein each $R^{10}$ is independently $C_1$-$C_6$ alkyl, and $R^{11}$ is selected from an electron pair and H; where $R^2$ is selected from the group consisting of H, G, acyl, trityl, 4-methoxytrityl, and a moiety of the formula:

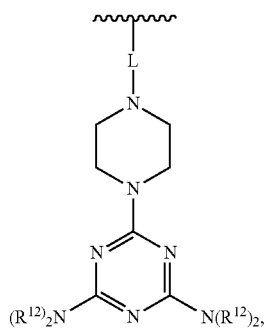

Where L is selected from —C(O)(CH$_2$)$_6$C(O)— and —C(O)(CH$_2$)$_2$S$_2$(CH$_2$)$_2$C(O)—, and each $R^{12}$ is of the formula —(CH$_2$)$_2$OC(O)N($R^{26}$)$_2$ wherein each $R^{26}$ is of the formula (CH$_2$)$_6$NHC(=NH)NH$_2$; where $R^3$ is selected from the group consisting of an electron pair, H, and $C_1$-$C_6$ alkyl, wherein G is a cell penetrating peptide ("CPP") and linker moiety selected from the group consisting of: —C(O)(CH$_2$)$_5$NH—CPP, —C(O)(CH$_2$)$_2$NH—CPP, —C(O)(CH$_2$)$_2$NHC(O)(CH$_2$)$_5$NH—CPP, —C(O)CH$_2$NH—CPP, and —C(O)CH(pyrrolidin-2-yl)NH—CPP wherein the CPP is attached to the linker moiety by an amide bond at the CPP carboxy terminus, with the proviso that one instance of G is present.

In some embodiments, the targeting sequence is complimentary to a *Pseudomonas aeruginosa* mRNA that encodes RpsJ, LpxC, FabG, AcpP, RpmB, WaaC, MraY, MurC, AccA, LpxA, LpxB, WaaG, WaaA, WaaF, MurB, MurE, AccB, FabZ, MurF, MurG, or AmpR.

In some embodiments the nucleobase sequence comprises a targeting sequence that is complementary to a *Pseudomonas aeruginosa* mRNA, wherein the targeting sequence is selected from Table 1, a fragment of at least 10 contiguous nucleotides of a targeting sequence in Table 1, or variant having at least 80% sequence identity to a targeting sequence in Table 1, wherein the thymine bases may be uracil bases.

In certain embodiments, the CPP is an arginine-rich peptide. In certain embodiments, the CPP is selected from Table 2.

In some embodiments, $R^2$ is selected from H or G, and $R^3$ is selected from an electron pair or H. In a particular embodiment, $R^2$ is G and G is selected from Table 2. In some embodiments, $R^2$ is H or acyl. In some embodiments, each $R^1$ is —N(CH$_3$)$_2$.

In certain embodiments, T is of the formula:

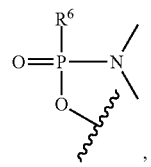

and $R^6$ is of the formula:

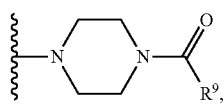

and $R^2$ is G.

In certain embodiments, T is of the formula:

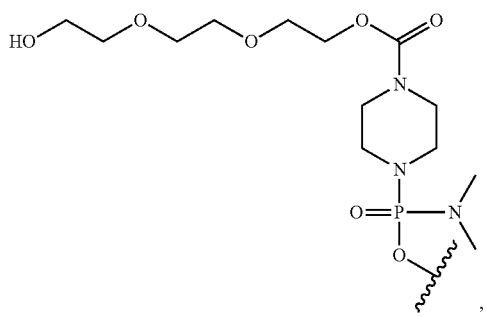 [SMILES: *OP(=O)(N(C)C)N1CCN(C(=O)OCCOCCOCCO)CC1]

and $R^2$ is G.

In certain embodiments, T is of the formula:

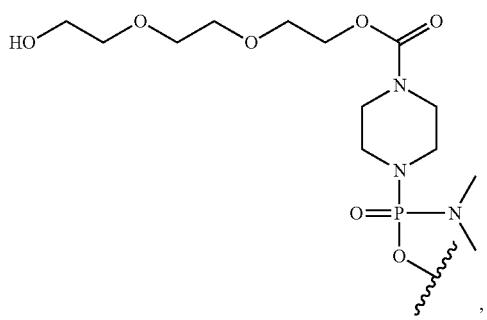 [SMILES: *OP(=O)(N(C)C)N1CCN(C(=O)OCCOCCOCCO)CC1]

each $R^1$ is —N(CH$_3$)$_2$, $R^2$ is G and wherein the targeting sequence and corresponding G are selected from Table 3.

In certain embodiments, T is of the formula:

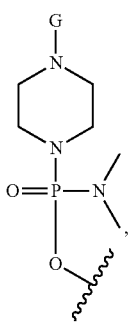

each $R^1$ is —N(CH$_3$)$_2$, and $R^2$ is —C(O)CH$_3$, wherein the targeting sequence and corresponding G are selected from Table 4.

Also included is a combination comprising: a) the compound of Formula (I) according to any one of the above permutations or described in further detail below, or a pharmaceutically acceptable salt thereof; and b) a second compound selected from the group consisting of polymyxin E (PME), polymyxin B (PMB), polymyxin B nonapeptide (PMBN), polymyxin E nonapeptide (PMEN), a pharmaceutically acceptable salt of any of the foregoing, and combinations thereof. In some embodiments, the ratio of compound (I) to second compound is selected from about 1:1, 2:1, 4:1, 8:1, 10:1, 12:1, 14:1, 16:1, 18:1, and 20:1. In particular embodiments, the second compound is PME. In other embodiments, the ratio of compound (I) to PME is selected from about 1:1, 2:1, 4:1, 8:1, 10:1, 12:1, 14:1, 16:1, 18:1, and 20:1. In some embodiments, the second compound is PMBN. In some embodiments, the ratio of compound (I) to PMBN is selected from about 1:1, 2:1, 4:1, 8:1, 10:1, 12:1, 14:1, 16:1, 18:1, and 20:1. In other embodiments, the amount of second compound present relative to compound (I) is subtherapeutic for antibacterial activity of the second compound.

Also included is a pharmaceutical composition, comprising:

(1) a compound, or a pharmaceutically acceptable salt thereof, of formula (I) of the disclosure, and (2) a pharmaceutically acceptable carrier.

In some embodiments, the targeting sequence is complimentary to a *Pseudomonas aeruginosa* mRNA that encodes RpsJ, LpxC, FabG, AcpP, RpmB, WaaC, MraY, MurC, AccA, LpxA, LpxB, WaaG, WaaA, WaaF, MurB, MurE, AccB, FabZ, MurF, MurG, or AmpR.

In some embodiments the nucleobase sequence comprises a targeting sequence that is complementary to a *Pseudomonas aeruginosa* mRNA, wherein the targeting sequence is selected from Table 1, a fragment of at least 10 contiguous nucleotides of a targeting sequence in Table 1, or variant having at least 80% sequence identity to a targeting sequence in Table 1, wherein the thymine bases may be uracil bases.

In some embodiments, the pharmaceutical composition further comprises a second compound selected from the group consisting of polymyxin E (PME), polymyxin B (PMB), polymyxin B nonapeptide (PMBN), polymyxin E nonapeptide (PMEN), a pharmaceutically acceptable salt of any of the foregoing, and combinations thereof. In some embodiments, the ratio of compound (I) to second compound is selected from about 1:1, 2:1, 4:1, 8:1, 10:1, 12:1, 14:1, 16:1, 18:1, and 20:1. In particular embodiments, the second compound is PME. In some embodiments, the ratio of compound (I) to PME is selected from about 1:1, 2:1, 4:1, 8:1, 10:1, 12:1, 14:1, 16:1, 18:1, and 20:1. In some embodiments, the second compound is PMBN. In other embodiments, the ratio of compound (I) to PMBN is selected from about 1:1, 2:1, 4:1, 8:1, 10:1, 12:1, 14:1, 16:1, 18:1, and 20:1. In other embodiments, the amount of second compound present relative to compound (I) is subtherapeutic for antibacterial activity of the second compound.

Also included are methods of treating a *Pseudomonas aeruginosa* infection, comprising administering to a patient in need thereof an effective amount of a composition comprising a compound of formula (I) of the disclosure, and a pharmaceutically acceptable carrier.

In some embodiments the nucleobase sequence comprises a targeting sequence that is complementary to a *Pseudomonas aeruginosa* mRNA, wherein the targeting sequence is selected from Table 1, a fragment of at least 10 contiguous nucleotides of a targeting sequence in Table 1, or variant having at least 80% sequence identity to a targeting sequence in Table 1, wherein the thymine bases may be uracil bases.

In some embodiments, the method further comprises administering a composition that comprises a compound selected from the group consisting of polymyxin E (PME), polymyxin B (PMB), polymyxin B nonapeptide (PMBN), polymyxin E nonapeptide (PMEN), a pharmaceutically acceptable salt of any of the foregoing, and combinations thereof. In particular embodiments, the second compound is PME. In other embodiments, the ratio of compound (1) to PME is selected from about 1:1, 2:1, 4:1, 8:1, 10:1, 12:1, 14:1, 16:1, 18:1, and 20:1. In some embodiments, the second compound is PMBN. In other embodiments, the ratio of compound (I) to PMBN is selected from about 1:1, 2:1, 4:1, 8:1, 10:1, 12:1, 14:1, 16:1, 18:1, and 20:1. In some embodiments, the amount of the second compound present in the pharmaceutical composition is below a therapeutic level for antibiotic activity of the second compound in treating the *Pseudomonas aeruginosa* infection.

In some embodiments, the method further comprises the step of administering ampicillin to the patient. In other embodiments, the ampicillin is co-administered with the pharmaceutical composition. In certain embodiments, the pharmaceutical composition further comprises ampicillin.

Also included is a pharmaceutical combination therapy for the treatment or prevention of a *Pseudomonas aeruginosa* infection in a patient in need thereof, comprising:

(1) a compound of formula (I) according to the disclosure, and (2) a second compound selected from the group consisting of polymyxin E (PME), polymyxin B (PMB), polymyxin B nonapeptide (PMBN), polymyxin E nonapeptide (PMEN), a pharmaceutically acceptable salt of any of the foregoing, and combinations thereof. In some embodiments, the amount of second compound relative to compound (I) is subtherapeutic for antibacterial activity of the second compound.

In some embodiments the nucleobase sequence comprises a targeting sequence that is complementary to a *Pseudomonas aeruginosa* mRNA, wherein the targeting sequence is selected from Table 1, a fragment of at least 10 contiguous nucleotides of a targeting sequence in Table 1, or variant having at least 80% sequence identity to a targeting sequence in Table 1, wherein the thymine bases may be uracil bases.

In some embodiments, the subject or patient is infected with a drug-resistant or multiple-drug resistant (MDR) strain of *Pseudomonas aeruginosa*. In particular embodiments, the subject has or is at risk for having cystic fibrosis (CF).

BRIEF DESCRIPTION OF THE FIGURES

FIG. 4A: MICs were performed in MH with 2 µg/mL PMBN. FIG. 4B: MICs were performed in MOPS MM without PMBN. FIG. 4C: MICs were performed in MOPS MM with 0.25 µg/mL of PMBN.

FIG. 6 shows PPMO treatment prevents formation of *P. aeruginosa* biofilm. *P. aeruginosa* PAO1 ($5 \times 10^5$ cfu/mL) was grown in MHII media in an MBEC plate for 20 hours either alone or in the presence of 5 µM of the indicated PPMOs, PMBN alone, $(RXR)_4$, or a scrambled PPMO. All conditions contained 2 µg/mL of PMBN unless indicated otherwise. Pegs were processed for crystal violet or visualized by microscopy at 20 hours.

FIG. 7 shows PPMO treatment diminishes existing *P. aeruginosa* biofilm. *P. aeruginosa* PAO1 ($5 \times 10^5$ cfu/mL) was grown in an MBEC plate for 24 hours. At 24 hours, the pegs were moved to a new 96-well plate containing fresh MHII media and either scrambled, RpsJ, or AcpP PPMO at the indicated concentrations. All wells containing PPMOs (including Scrambled) contained 2 µg/mL of PMBN. The pegs were again moved to new plates with or without PPMOs at 32 and 40 hours. Pegs were processed for crystal violet or visualized with microscopy at 48 hours.

DETAILED DESCRIPTION

Definitions

Figure 1:
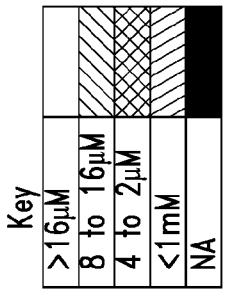
FIG. 1 shows a heat map of the minimal inhibitory concentration (MIC) values for PPMOs of Tables 3 and 4 tested against a panel of 21 *P. aeruginosa* clinical isolates with varying levels of antibiotic resistance. MICs are indicated under each PPMO by color (grey=>16 µM, blue=8 to 16 µM, red=2 to 4 µM, and maroon=<1 µM, white=MIC not detected) and by numeric value.
Figure 1:
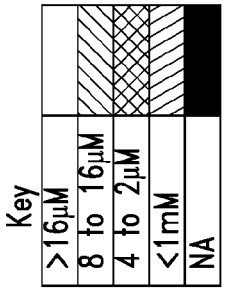

Unless defined otherwise, all technical and scientific terms used herein have the same meaning as commonly understood by those of ordinary skill in the art to which the disclosure belongs. Although any methods and materials similar or equivalent to those described herein can be used in the practice or testing of the present disclosure, preferred methods and materials are described. For the purposes of the present disclosure, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight, or length that varies by as much as 30, 25, 20, 15, 10, 9, 8, 7, 6, 5, 4, 3, 2 or 1% to a reference quantity, level, value, number, frequency, percentage, dimension, size, amount, weight, or length.

By "coding sequence" is meant any nucleic acid sequence that contributes to the code for the polypeptide product of a gene. By contrast, the term "non-coding sequence" refers to any nucleic acid sequence that does not directly contribute to the code for the polypeptide product of a gene.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of:" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

As used herein, the terms "contacting a cell", "introducing" or "delivering" include delivery of the oligonucleotides of the disclosure into a cell by methods routine in the art, e.g., transfection (e.g., liposome, calcium-phosphate, polyethyleneimine), electroporation (e.g., nucleofection), microinjection), transformation, and administration.

The terms "cell penetrating peptide" (CPP) or "a peptide moiety which enhances cellular uptake" are used interchangeably and refer to cationic cell penetrating peptides, also called "transport peptides", "carrier peptides", or "peptide transduction domains". In some aspects, the peptides have the capability of inducing cell penetration within about or at least about 30%, 40%, 50%, 60%, 70%, 80%, 90%, or 100% of cells of a given population and/or allow macromolecular translocation to or within multiple tissues in vivo upon systemic administration. Particular examples of CPPs include "arginine-rich peptides." CPPs are well-known in the art and are disclosed, for example, in U.S. Application No. 2010/0016215, which is incorporated by reference in its entirety.

"An electron pair" refers to a valence pair of electrons that are not bonded or shared with other atoms.

"Homology" refers to the percentage number of amino acids that are identical or constitute conservative substitutions. Homology may be determined using sequence comparison programs such as GAP (Deveraux et al., 1984, Nucleic Acids Research 12, 387-395) or BLAST. In this way sequences of a similar or substantially different length to those cited herein could be compared by insertion of gaps into the alignment, such gaps being determined, for example, by the comparison algorithm used by GAP.

By "isolated" is meant material that is substantially or essentially free from components that normally accompany it in its native state. For example, an "isolated polynucleotide" or "isolated oligonucleotide," as used herein, may refer to a polynucleotide that has been purified or removed from the sequences that flank it in a naturally-occurring state, e.g., a DNA fragment that is removed from the sequences that are adjacent to the fragment in the genome. The term "isolating" as it relates to cells refers to the purification of cells (e.g., fibroblasts, lymphoblasts) from a source subject (e.g., a subject with a polynucleotide repeat disease). In the context of mRNA or protein, "isolating" refers to the recovery of mRNA or protein from a source, e.g., cells.

The term "modulate" includes to "increase" or "decrease" one or more quantifiable parameters, optionally by a defined and/or statistically significant amount. By "increase" or "increasing," "enhance" or "enhancing," or "stimulate" or "stimulating," refers generally to the ability of one or antisense compounds or compositions to produce or cause a greater physiological response (i.e., downstream effects) in a cell or a subject relative to the response caused by either no antisense compound or a control compound. Relevant physiological or cellular responses (in vivo or in vitro) will be apparent to persons skilled in the art. An "increased" or "enhanced" amount is typically a "statistically significant" amount, and may include an increase that is 1.1, 1.2, 2, 3, 4, 5, 6, 7, 8, 9, 10, 15, 20, 30, 40, 50 or more times (e.g., 500, 1000 times) (including all integers and ranges between and above 1), e.g., 1.5, 1.6, 1.7, 1.8) the amount produced by no antisense compound (the absence of an agent) or a control compound. The term "reduce" or "inhibit" may relate generally to the ability of one or more antisense compounds or compositions to "decrease" a relevant physiological or cellular response, such as a symptom of a disease or condition described herein, as measured according to routine techniques in the diagnostic art. Relevant physiological or cellular responses (in vivo or in vitro) will be apparent to persons skilled in the art, and may include reductions in bacterial cell growth, reductions in the minimum inhibitory concentration (MIC) of an antimicrobial agent, and others. A "decrease" in a response may be "statistically significant" as compared to the response produced by no antisense compound or a control composition, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers and ranges in between.

As used herein, an "antisense oligonucleotide" or "oligonucleotide" refers to a linear sequence of nucleotides, or nucleotide analogs, which allows the nucleobase to hybridize to a target sequence in an RNA by Watson-Crick base pairing, to form an oligonucleotide:RNA heteroduplex within the target sequence. The terms "antisense oligonucleotide", "antisense oligomer", "oligomer" and "compound" may be used interchangeably to refer to an oligonucleotide. The cyclic subunits may be based on ribose or another pentose sugar or, in certain embodiments, a morpholino group (see description of morpholino oligonucleotides below).

The term "oligonucleotide" or "antisense oligonucleotide" also encompasses an oligonucleotide having one or more additional moieties conjugated to the oligonucleotide, e.g., at its 3'- or 5'-end, such as a polyethylene glycol moiety or other hydrophilic polymer, e.g., one having 10-100 monomeric subunits, which may be useful in enhancing solubility, or a moiety such as a lipid or peptide moiety that is effective to enhance the uptake of the compound into target bacterial cells and/or enhance the activity of the compound within the cell, e.g., enhance its binding to a target polynucleotide.

A "nuclease-resistant" oligonucleotides refers to one whose backbone is substantially resistant to nuclease cleavage, in non-hybridized or hybridized form; by common extracellular and intracellular nucleases in the body or in a bacterial cell (for example, by exonucleases such as 3'-exonucleases, endonucleases, RNase H); that is, the oligonucleotide shows little or no nuclease cleavage under normal nuclease conditions to which the oligonucleotide is exposed. A "nuclease-resistant heteroduplex" refers to a heteroduplex formed by the binding of an antisense oligomer to its complementary target, such that the heteroduplex is substantially resistant to in vivo degradation by intracellular and extracellular nucleases, which are capable of cutting double-stranded RNA/RNA or RNA/DNA complexes. A "heteroduplex" refers to a duplex between an antisense oligonucleotide and the complementary portion of a target RNA.

As used herein, "nucleobase" (Nu), "base pairing moiety" or "base" are used interchangeably to refer to a purine or pyrimidine base found in native DNA or RNA (uracil, thymine, adenine, cytosine, and guanine), as well as analogs of the naturally occurring purines and pyrimidines, that confer improved properties, such as binding affinity to the oligonucleotide. Exemplary analogs include hypoxanthine (the base component of the nucleoside inosine); 2, 6-diaminopurine; 5-methyl cytosine; C5-propynyl-modified pyrimidines; 9-(aminoethoxy)phenoxazine (G-clamp), and the like.

A nucleobase covalently linked to a ribose, sugar analog or morpholino comprises a nucleoside. "Nucleotides" are composed of a nucleoside together with one phosphate group. The phosphate groups covalently link adjacent nucleotides to one another to form an oligonucleotide.

An oligonucleotide "specifically hybridizes" to a target sequence if the oligonucleotide hybridizes to the target under physiological conditions, with a Tm substantially greater than 40° C. or 45° C., preferably at least 50° C., and typically 60° C.–80° C. or higher. Such hybridization preferably corresponds to stringent hybridization conditions. At a given ionic strength and pH, the Tm is the temperature at which 50% of a target sequence hybridizes to a complementary polynucleotide. Such hybridization may occur with "near" or "substantial" complementarity of the antisense oligonucleotide to the target sequence, as well as with exact complementarity.

As used herein, "sufficient length" includes an antisense oligonucleotide that is complementary to at least about 8, more typically about 8-10, 8-11, 8-12, 8-13, 8-14, 8-15, 8-16, 8-17, 8-18, 8-19, 8-20, 8-30, 8-40, or 10-11, 10-12, 10-13, 10-14, 10-15, 10-16, 10-17, 10-18, 10-19, 10-20, 10-30, 10-40 (including all integers and ranges in between) contiguous or non-contiguous nucleobases in a region of a bacterial mRNA target sequence. An antisense oligonucleotide of sufficient length has at least a minimal number of nucleotides to be capable of specifically hybridizing to a region of the bacterial mRNA target. In some embodiments, an oligonucleotide of sufficient length is from 8 to 30 nucleotides in length, for example, about 10-20 nucleotides in length.

The terms "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., Nucl. Acids Res. 25:3389, 1997.

A "subject" or a "subject in need thereof" includes a mammalian subject such as a human subject or patient.

The terms "TEG" or "triethylene glycol tail" refer to triethylene glycol moieties conjugated to the oligonucleotide, e.g., at its 3'- or 5'-end. For example, in some embodiments, "TEG" includes wherein T of the compound of formula (I) is of the formula:

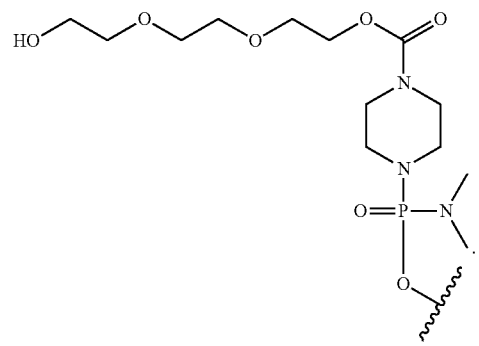 [SMILES: *OP(=O)(N(C)C)N1CCN(C(=O)OCCOCCOCCO)CC1]

The term "target sequence" refers to a portion of the target RNA, for example, a bacterial mRNA, against which the antisense oligonucleotide is directed, that is, the sequence to which the oligonucleotide will hybridize by Watson-Crick base pairing of a complementary sequence. In certain embodiments, the target sequence may be a contiguous region of the translation initiation region of a bacterial gene.

The "translational start codon region" refers to a region that is 30 bases upstream or downstream of a translation initiation codon of a gene.

The term "targeting sequence" or "antisense targeting sequence" refers to the sequence in an oligonucleotide that is complementary or substantially complementary to the target sequence in the RNA, e.g., the bacterial mRNA. The entire sequence, or only a portion, of the antisense compound may be complementary to the target sequence. For example, in an oligonucleotide of about 10-30 bases, about 6, 7, 8, 9, 10, 11, 12, 13, 14, 15, 16, 17, 18, 19, 20, 21, 22, 23, 24, 25, 26, 27, 28, or 29 of the bases may be targeting sequences that are complementary to the target region. Typically, the targeting sequence is formed of contiguous bases, but may alternatively be formed of non-contiguous sequences that when placed together, e.g., from opposite ends of the oligonucleotide, constitute sequence that spans the target sequence.

A "targeting sequence" may have "near" or "substantial" complementarity to the target sequence and still function for the purpose of the present disclosure, that is, still be "complementary." In some embodiments, the oligonucleotide analog compounds employed in the present disclosure have, for example, at most one mismatch with the target sequence out of 10 nucleotides, and at most one mismatch out of 20. Alternatively, the antisense oligonucleotides employed may have, for example, sequence homology of at least 85%, of at least 90%, or at least 95% sequence homology with the exemplary targeting sequences as described herein.

As used herein, the term "quantifying", "quantification" or other related words refer to determining the quantity, mass, or concentration in a unit volume, of a nucleic acid, polynucleotide, oligonucleotide, peptide, polypeptide, or protein.

As used herein, "treatment" of a subject (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent. Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

As used herein, the term "pharmaceutical combination therapy" or just "combination therapy" generally refers to the administration of a compound of formula (I) described herein in combination with a second compound, such as a polymyxin or polymyxin nonapeptide selected from the group consisting of polymyxin E (PME), polymyxin B (PMB), polymyxin B nonapeptide (PMBN), polymyxin E nonapeptide (PMEN), a pharmaceutically acceptable salt of any of the foregoing, and combinations thereof disclosed herein. In other words, the term "pharmaceutical combination therapy" means a PPMO of the disclosure, such as a compound of formula (I), may be administered concomitantly in a pharmaceutically acceptable form with one or more of the second compounds disclosed herein: (i) in the same dosage form, e.g., the same tablet or pharmaceutical composition meaning a pharmaceutical composition comprising a PPMO of the disclosure, such as a compound of formula (I), one or more second compounds disclosed herein, and a pharmaceutically acceptable carrier; (ii) in a separate dosage form having the same mode of administration, e.g., a kit comprising a first pharmaceutical composition suitable for oral administration comprising a PPMO of the disclosure, such as a compound of formula (I) and a pharmaceutically acceptable carrier, and a second pharmaceutical composition suitable for oral administration comprising a second compound of the disclosure and a pharmaceutically acceptable carrier; and (iii) in a separate dosage form having different modes of administration, e.g., a kit comprising a first pharmaceutical composition suitable for oral administration comprising a PPMO of the disclosure, such as a compound of formula (I) and a pharmaceutically acceptable carrier, and a second pharmaceutical composition suitable for parenteral administration comprising a second compound of the disclosure and a pharmaceutically acceptable carrier. Further, those of skill in the art given the benefit of the present disclosure will appreciate that when more than one second compound of the disclosure is being administered, the agents need not share the same mode of administration, e.g., a kit comprising a first pharmaceutical composition suitable for oral administration comprising a PPMO of the disclosure, such as a compound of formula (I) and a pharmaceutically acceptable carrier, a second pharmaceutical composition suitable for oral administration comprising a first second compound of the disclosure and a pharmaceutically acceptable carrier, and a third pharmaceutical composition suitable for parenteral administration comprising a second compound of the disclosure and a pharmaceutically acceptable carrier. Those of skill in the art will appreciate that the concomitant administration referred to above in the context of a "pharmaceutical combination therapy" means that the pharmaceutical composition comprising a PPMO of the disclosure and a pharmaceutical composition(s) comprising the second compound can be administered on the same schedule, i.e., at the same time and day, or on a different schedule, i.e., on different, although not necessarily distinct, schedules. In that regard, when the pharmaceutical composition comprising a PPMO of the disclosure and a pharmaceutical composition(s) comprising the second compound of the disclosure is administered on a different schedule, such a different schedule may also be referred to herein as "background" or "background administration." For example, the pharmaceutical composition comprising a PPMO of the disclosure may be administered in a certain dosage form twice a day, and the pharmaceutical composition(s) comprising the second compound of the disclosure may be administered once a day, such that the pharmaceutical composition comprising a PPMO of the disclosure may but not necessarily be administered at the same time as the pharmaceutical composition(s) comprising the second compound of the disclosure during one of the daily administrations. Of course, other suitable variations to "pharmaceutical combination therapy" will be readily apparent to those of skill in the art given the benefit of the present disclosure and are part of the meaning of this term.

Sequences for Targeting Bacterial Genes in Biochemical Pathways and Cellular Processes Certain embodiments relate to antisense oligonucleotides, and related compositions and methods, which are of sufficient length and complementarity to specifically hybridize to a bacterial mRNA target sequence that encodes a gene in a biochemical pathway and/or cellular process. General examples include: murein biosynthesis, cell division, global gene regulatory mechanisms, fatty acid biosynthesis, ribosomal proteins, DNA replication, transcription, translation initiation, lipopolysaccharide biosynthesis, nucleic acid biosynthesis, and intermediary metabolism. Particular examples of genes in biochemical pathways and cellular processes include: RpsJ and RpmB (ribosomal proteins); LpxC, WaaC, WaaG, WaaA, WaaF, LpxA, and LpxB (lipopolysaccharide biosynthesis); MraY, MurC, MurB, MurE, MurF, and MurG (murein biosynthesis); and FabG, AcpP (fatty acid biosynthesis), AccA, AccB, and FabZ (fatty acid biosynthesis).

Also included are bacterial mRNA target sequences that encode at least one virulence factor such as an antibiotic resistance gene/protein. One specific example includes AmpR, a global transcriptional regulator of the β-lactamase AmpC.

In certain embodiments, the target sequence contains all or a portion (e.g., 1 or 2 nucleotides) of a translational start codon of the bacterial mRNA. In some embodiments, the target sequence contains a sequence that is about or within about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 bases upstream or downstream of a translational start codon (e.g., ATG; AUG) of the bacterial mRNA target sequence. For example, in particular embodiments, the 5'-end of the target sequence is the adenine, uracil, or guanine nucleotide in a translational start codon of the bacterial mRNA. In some embodiments, the 5'-end or 3'-end of the target sequence begins at residue 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 downstream of the last nucleotide (e.g., guanine) of a translational start codon of the bacterial mRNA. In some embodiments, the 5'-end or 3'-end of the target sequence begins at residue 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 upstream of the first nucleotide (e.g., adenine) of a translational start codon of the bacterial mRNA.

Selected antisense targeting sequences can be made shorter, e.g., about 8, 9, 10, 11, 12, 13, 14, or 15 bases, or longer, e.g., about 20, 30, or 40 bases, and include a small number of mismatches, as long as the sequence is sufficiently complementary to reduce transcription or translation upon hybridization to the target sequence, and optionally forms with the RNA a heteroduplex having a Tm of 45° C. or greater.

In certain embodiments, the degree of complementarity between the target sequence and antisense targeting sequence is sufficient to form a stable duplex. The region of complementarity of the antisense oligonucleotides with the target RNA sequence may be as short as 8-9 bases, 8-10 bases, 8-11 bases, 8-12 bases, 10-11 bases, 10-12 bases, but can be 12-15 bases or more, e.g., 10-40 bases, 12-30 bases, 12-25 bases, 15-25 bases, 12-20 bases, or 15-20 bases, including all integers in between these ranges. An antisense oligonucleotide of about 10-15 bases is generally long enough to have a unique complementary sequence. In certain embodiments, a minimum length of complementary bases may be required to achieve the requisite binding Tm, as discussed herein.

In certain embodiments, oligonucleotides as long as 40 bases may be suitable, where at least a minimum number of bases, e.g., 10-12 bases, are complementary to the target sequence. In general, however, facilitated or active uptake in cells is optimized at oligonucleotide lengths of less than about 30 bases and less than about 20 bases. Included are antisense oligonucleotides that comprises or consist of about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bases, for example, 10 to 40 bases, 10 to 30 bases, 10 to 20 bases, 15 to 40, 15 to 30, 15 to 20, 11 to 40, 11 to 30, or 11 to 20 bases (including all integers and ranges in between), in which at least about 6, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 contiguous or non-contiguous bases are complementary to a target gene described herein In some embodiments, the target gene is RpsJ, LpxC, FabG, AcpP, RpmB, WaaC, MraY, MurC, AccA, LpxA, LpxB, WaaG, WaaA, WaaF, MurB, MurE, AccB, FabZ, MurF, MurG, or AmpR. In certain embodiments, the antisense oligonucleotides of the disclosure comprise a targeting sequence that is complementary to a *Pseudomonas aeruginosa* mRNA encoding RpsJ, LpxC, FabG, AcpP, RpmB, WaaC, MraY, MurC, AccA, LpxA, LpxB, WaaG, WaaA, WaaF, MurB, MurE, AccB, FabZ, MurF, MurG, or AmpR.

In certain embodiments, antisense oligonucleotides may be 100% complementary to the target sequence, or may include mismatches, e.g., to accommodate variants, as long as a heteroduplex formed between the oligonucleotide and target sequence is sufficiently stable to withstand the action of cellular nucleases and other modes of degradation which may occur in vivo, and reduce expression of the targeted mRNA. Hence, certain oligonucleotides may have about or at least about 70% sequence complementarity, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence complementarity, between the oligonucleotide and the target sequence. Oligonucleotide backbones that are less susceptible to cleavage by nucleases are discussed herein. Mismatches, if present, are typically less destabilizing toward the end regions of the hybrid duplex than in the middle. The number of mismatches allowed will depend on the length of the oligonucleotide, the percentage of G:C base pairs in the duplex, and the position of the mismatch(es) in the duplex, according to well understood principles of duplex stability. Although such an antisense oligonucleotide is not necessarily 100% complementary to the target sequence, it is effective to stably and specifically bind to the target sequence, for example, such that translation of the target RNA is reduced.

The stability of the duplex formed between an oligonucleotide and a target sequence is a function of the binding Tm and the susceptibility of the duplex to cellular enzymatic cleavage. The Tm of an oligonucleotide with respect to complementary-sequence RNA may be measured by conventional methods, such as those described by Hames et al., Nucleic Acid Hybridization, IRL Press, 1985, pp. 107-108 or as described in Miyada C. G. and Wallace R. B., 1987, Oligonucleotide Hybridization Techniques, Methods Enzymol. Vol. 154 pp. 94-107. In certain embodiments, antisense oligonucleotides may have a binding Tm, with respect to a complementary-sequence RNA, of greater than body temperature and preferably greater than about 45° C. or 50° C. Tm's in the range 60-80° C. or greater are also included. According to well-known principles, the Tm of an oligonucleotide, with respect to a complementary-based RNA hybrid, can be increased by increasing the ratio of C:G paired bases in the duplex, and/or by increasing the length (in base pairs) of the heteroduplex. At the same time, for purposes of optimizing cellular uptake, it may be advantageous to limit the size of the oligonucleotide.

Table 1 below shows exemplary targeting sequences (in a 5'-to-3' orientation) of the antisense oligonucleotides described herein.

TABLE 1

Exemplary Targeting Sequences

| Target gene | Targeting Sequence* | SEQ ID NO: |
|---|---|---|
| RpsJ | CCT CAG ACT CC | 1 |
| LpxC | GTT GTT TGA TC | 2 |
| FabG | TTC TCT CCT TT | 3 |
| AcpP | CAT ACC TTG TT | 4 |
| RpmB | CTC TAG ACA TG | 5 |
| WaaC | AGC ACC CTC AT | 6 |
| MraY | TGA CTC TCC TC | 7 |
| MurC | CCA CCT CCA GG | 8 |
| AccA | AGG CTT CCG TC | 9 |
| LpxA | ATC AAA CTC AT | 10 |
| LpxB | TAA TCC GTC AG | 11 |
| WaaG | GCC AGG GTC AT | 12 |
| RpsJ | GCA TTT GAC CT | 13 |
| WaaA | GTA CGG TTC AT | 14 |
| WaaF | AGA ATT CTC AT | 15 |
| MurB | CAG TCG CCC CT | 16 |
| MurE | AGG CTC ATA GG | 17 |
| AccB | CTA GCA CTC CC | 18 |
| FabZ | ATG TCC ATC AT | 19 |
| MurF | ACC TCC CAG GC | 20 |
| MurG | GCA AAG TCC TC | 21 |
| AmpR | GTC GAA CCA AT | 22 |
| AcpP | CTC ATA CCT TG | 35 |

*The thymines (T) can be uracils (U), and vice versa

TABLE A

Exemplary Scrambled Control Sequences

| Target gene | Targeting Sequence* | SEQ ID NO: |
|---|---|---|
| scrambled | TCT CAG ATG GT | 36 |
| scrambled | ATC GTT GCA TC | 37 |

*The thymines (T) can be uracils (U), and vice versa

In some embodiments, the thymine bases of the targeting sequences of Table 1 are uracil bases.

Certain antisense oligonucleotides thus comprise, consist, or consist essentially of a targeting sequence in Table 1 (e.g., SEQ ID NOS: 1-22, 35) or a variant or contiguous or non-contiguous portion(s) thereof. For instance, certain antisense oligonucleotides comprise about or at least about 6, 7, 8, 9, 10, 11, 12, 13, 14, 15, 16, 17, 18, 19, 20, 21, 22, 23, 24, 25, 26, or 27 contiguous or non-contiguous nucleotides of any of the targeting sequences in Table 1 (e.g., SEQ ID NOS: 1-22, 35). For non-contiguous portions, intervening nucleotides can be deleted or substituted with a different nucleotide, or intervening nucleotides can be added. Additional examples of variants include oligonucleotides having about or at least about 70% sequence identity or homology, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity or homology, over the entire length of any of the targeting sequences in Table 1 (e.g., SEQ ID NOS: 1-22, 35).

The activity of antisense oligonucleotides and variants thereof can be assayed according to routine techniques in the art (see, e.g., the Examples).

Antisense Oligonucleotide Chemistries

The antisense oligonucleotides typically comprises a base sequence of sufficient length and complementarity to specifically hybridize to a bacterial mRNA target sequence that encodes a gene in a biochemical pathway and/or cellular process, and thereby reduce expression (e.g., translation) of the biochemical pathway and/or cellular process protein. This requirement is optionally met when the oligomer compound has the ability to be actively taken up by bacterial cells, and once taken up, form a stable duplex (or heteroduplex) with the target mRNA, optionally with a Tm greater than about 40° C. or 45° C.

In certain embodiments, the backbone of the antisense oligonucleotide is substantially uncharged, and is optionally recognized as a substrate for active or facilitated transport across a cell wall and/or cell membrane. The ability of the oligonucleotide to form a stable duplex with the target RNA may also relate to other features of the backbone, including the length and degree of complementarity of the antisense oligonucleotide with respect to the target, the ratio of G:C to A:T base matches, and the positions of any mismatched bases. The ability of the antisense oligonucleotide to resist cellular nucleases may promote survival and ultimate delivery of the agent to the cell. Thus, in some embodiments, the antisense oligonucleotide is nuclease-resistant. Exemplary antisense oligonucleotide targeting sequences are listed in Table 1 (supra).

In certain embodiments, the antisense oligonucleotide is a morpholino oligonucleotide, for example, a phosphorodiamidate morpholino oligonucleotide (PMO). A "morpholino oligonucleotide" or "PMO" includes an oligonucleotide having a backbone which supports a nucleobase capable of hydrogen bonding to typical polynucleotides, wherein the polymer lacks a pentose sugar backbone moiety, but instead contains a morpholino ring. Thus, in a PMO a morpholino ring structure supports a base pairing moiety, to form a sequence of base pairing moieties which is typically designed to hybridize to a selected antisense target in a cell or in a subject being treated. An exemplary "morpholino" oligonucleotide comprises morpholino subunit structures linked together by phosphoramidate or phosphorodiamidate linkages, joining the morpholino nitrogen of one subunit to the 5' exocyclic carbon of an adjacent subunit, each subunit comprising a purine or pyrimidine nucleobase effective to bind, by base-specific hydrogen bonding, to a base in a polynucleotide.

Morpholino oligonucleotides (including antisense oligonucleotides) and their synthesis are detailed, for example, in U.S. Pat. Nos. 5,698,685; 5,217,866; 5,142,047; 5,034,506; 5,166,315; 5,185,444; 5,521,063; 5,506,337 and pending U.S. patent application Ser. Nos. 12/271,036; 12/271,040; and PCT publication numbers WO/2009/064471 and WO/2012/043730, all of which are incorporated herein by reference in their entireties.

Within the oligonucleotide structure, the phosphate groups are commonly referred to as forming the "internucleoside linkages" of the oligonucleotide. The naturally occurring internucleoside linkage of RNA and DNA is a 3' to 5' phosphodiester linkage. A "phosphoramidate" group comprises phosphorus having three attached oxygen atoms and one attached nitrogen atom, while a "phosphorodiamidate" group comprises phosphorus having two attached oxygen atoms and two attached nitrogen atoms.

In particular embodiments, the morpholino subunits are joined by phosphorodiamidate linkages in accordance with the structure:

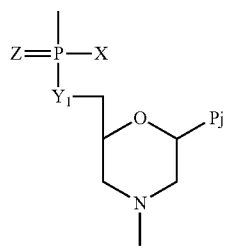

where $Y_1$=oxygen (O) or sulfur, nitrogen, or carbon; Z=oxygen or sulfur; Pj is a purine or pyrimidine base-pairing moiety effective to bind, by base-specific hydrogen bonding, to a base in a polynucleotide, and X is —NRR' where R and R' are the same or different and are either H or alkyl. In particular embodiments, X is —NRR', where R and R' are the same or different and are either H or methyl.

In certain embodiments, the phosphorodiamidate morpholino oligonucleotide is a compound, or a pharmaceutically acceptable salt thereof, of formula I:

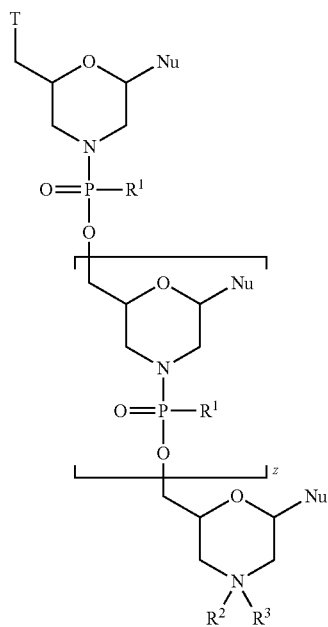

(I)

Where each Nu is a nucleobase which taken together forms a nucleobase sequence, Z is an integer from 8 to 38, T is selected from OH and a moiety of the formula:

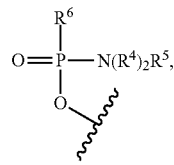

Where each $R^4$ is independently $C_1$-$C_6$ alkyl, and $R^5$ is selected from an electron pair and H, and $R^6$ is selected from —N($R^7$)$CH_2$C(O)$NH_2$, and a moiety of the formula:

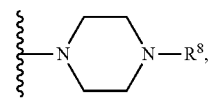

where $R^7$ is selected from H and $C_1$-$C_6$ alkyl, and $R^8$ is selected from G, —C(O)—$R^9$, acyl, trityl, and 4-methoxytrityl, where $R^9$ is of the formula —(O-alkyl)$_y$-OH wherein y is an integer from 3 to 10 and each of the y alkyl groups is independently selected from $C_2$-$C_6$ alkyl; where each instance of $R^1$ is —N($R^{10}$)$_2R^{11}$ wherein each $R^{10}$ is independently $C_1$-$C_6$ alkyl, and $R^{11}$ is selected from an electron pair and H; where $R^2$ is selected from the group consisting of H, G, acyl, trityl, 4-methoxytrityl, and a moiety of the formula:

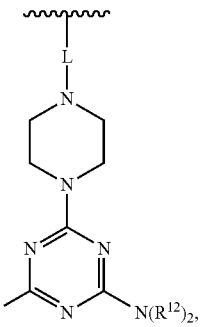

Where L is selected from —C(O)(CH$_2$)$_6$C(O)— and —C(O)(CH$_2$)$_2$S$_2$(CH$_2$)$_2$C(O)—, and each $R^{12}$ is of the formula —(CH$_2$)$_2$OC(O)N($R^{26}$)$_2$ wherein each $R^{26}$ is of the formula (CH$_2$)$_6$NHC(=NH)NH$_2$; where $R^3$ is selected from the group consisting of an electron pair, H, and $C_1$-$C_6$ alkyl, wherein G is a cell penetrating peptide ("CPP") and linker moiety selected from the group consisting of: —C(O)(CH$_2$)$_5$NH—CPP, —C(O)(CH$_2$)$_2$NH—CPP, —C(O)(CH$_2$)$_2$NHC(O)(CH$_2$)$_5$NH—CPP, —C(O)CH$_2$NH—CPP, and —C(O)CH(pyrrolidin-2-yl)NH—CPP wherein the CPP is attached to the linker moiety by an amide bond at the CPP carboxy terminus, with the proviso that one instance of G is present.

In some embodiments, Z is from 8 to 28, from 8 to 18. In certain embodiments, Z is 9 and the targeting sequence is selected from Table 1.

In some embodiments, $R^2$ is selected from H or G, and $R^3$ is selected from an electron pair or H. In a particular embodiment, $R^2$ is G and is selected from Table 2. In some embodiments, $R^2$ is H or acyl. In some embodiments, each $R^1$ is —N(CH$_3$)$_2$.

In certain embodiments, T is of the formula:

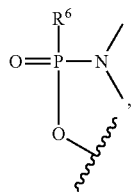

and $R^6$ is of the formula:

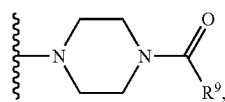

and $R^2$ is G.

In certain embodiments, T is of the formula:

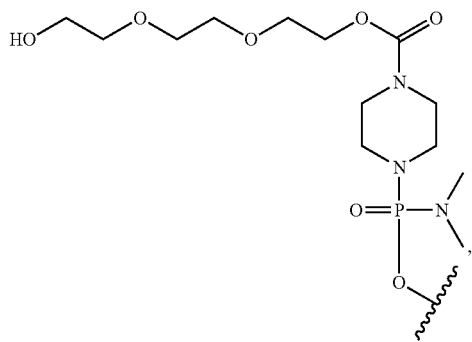 [SMILES: *OP(=O)(N(C)C)N1CCN(C(=O)OCCOCCOCCO)CC1]

and $R^2$ is G.

In certain embodiments, T is of the formula:

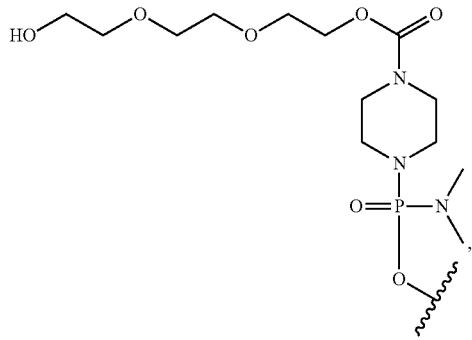 [SMILES: *OP(=O)(N(C)C)N1CCN(C(=O)OCCOCCOCCO)CC1]

each $R^1$ is —N(CH$_3$)$_2$, $R^2$ is G.

In certain embodiments, T is of the formula:

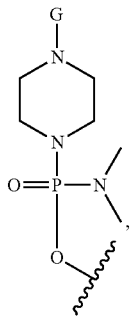

each $R^1$ is —N(CH$_3$)$_2$, and $R^2$ is —C(O)CH$_3$.

Because of the molecular weight and polar characteristics of PMOs, conjugating these oligonucleotides to membrane-penetrating or cell-penetrating peptides can improve entry into bacterial cells. Peptide-PMO conjugates (PPMO) are significantly more effective in inhibiting the expression of their specific targets than their non-conjugated counterparts. The membrane-penetrating peptide carries its cargo (the antisense oligomer) across the Gram-negative outer membrane, after which it traverses the plasma membrane.

In certain embodiments, the antisense oligonucleotide is conjugated to at least one cell-penetrating peptide (CPP). In some embodiments, the CPP is an arginine-rich peptide. By "arginine-rich carrier peptide" is meant that the CPP has at least 2, for example, 2, 3, 4, 5, 6, 7, or 8 arginine residues, each optionally separated by one or more uncharged, hydrophobic residues, and optionally containing about 6-14 amino acid residues. Exemplary CPPs are provided in Table 2 (SEQ ID NOS: 23-34).

TABLE 2

Exemplary Cell-Penetrating Peptide (CPP) Sequences

| CPP Name | Sequence | SEQ ID NO: |
|---|---|---|
| (RXR)4- | RXRRXRRXRRXR- | 23 |
| (RXRRBR)2- | RXRRBRRXRRBR- | 24 |
| R6- | RRRRRR- | 25 |
| (RFF)3R- | RFFRFFRFFR- | 26 |
| (RYR)4- | RYRRYRRYRRYR- | 27 |
| (RFR)4- | RFRRFRRFRRFR- | 28 |
| (RGR)4- | RGRRGRRGRRGR- | 29 |
| (dRdFdF)3- | dRdFdFdRdFdFdRdFdF- | 30 |
| (dRXdR)4- | dRXdRdRXdRdRXdRdRXdR- | 31 |
| dR8- | dRdRdRdRdRdRdRdR- | 32 |
| dR6- | dRdRdRdRdRdR- | 33 |
| (dRdFdF)3dR- | dRdFdFdRdFdFdRdFdFdR- | 34 |

X is 6-aminohexanoic acid; B is β-alanine

In some embodiments, the CPP is linked at its C-terminus to the 3'-end or the 5'-end of the oligonucleotide via a 1, 2, 3, 4, or 5 amino acid linker. In particular embodiments, the linkers can include: —C(O)(CH$_2$)$_5$NH—CPP (X linker), —C(O)(CH$_2$)$_2$NH—CPP (B linker), —C(O)(CH$_2$)$_2$NHC(O)(CH$_2$)$_5$NH—CPP (XB peptide linker), —C(O)CH$_2$NH—CPP (G linker), and —C(O)CH(pyrrolidin-2-yl)NH—CPP (P linker) wherein the CPP is attached to the linker moiety by an amide bond at the CPP carboxy terminus. Exemplary 3' CCP PPMOs used in the Examples are provided in Table 3 and exemplary 5' CCP PPMOs used in the Examples are provided in Table 4.

TABLE 3

Exemplary 3' CPP PPMO Compounds

| PPMO Name | Target Gene | Targeting Sequence (TS)* | TS SEQ ID NO: | 5' | 3' CPP/ Linker | CPP SEQ ID NO: |
|---|---|---|---|---|---|---|
| PPMO#1 | RpsJ5 | CCTCAGACTCC | 1 | TEG | (RGR)4XB | 29 |
| PPMO#2 | LpxC | GTTGTTTGATC | 2 | TEG | (RXR)4XB | 23 |
| PPMO#3 | FabG | TTCTCTCCTTT | 3 | TEG | (RXR)4XB | 23 |
| PPMO#4 | AcpP7 | CATACCTTGTT | 4 | TEG | (RXR)4XB | 23 |
| PPMO#5 | RpmB | CTCTAGACATG | 5 | TEG | (RXR)4XB | 23 |
| PPMO#6 | WaaC | AGCACCCTCAT | 6 | TEG | (RXR)4XB | 23 |
| PPMO#7 | MraY | TGACTCTCCTC | 7 | TEG | (RXR)4XB | 23 |
| PPMO#8 | MurC | CCACCTCCAGG | 8 | TEG | (RXR)4XB | 23 |
| PPMO#9 | AccA | AGGCTTCCGTC | 9 | TEG | (RXR)4XB | 23 |
| PPMO#10 | LpxA | ATCAAACTCAT | 10 | TEG | (RXR)4XB | 23 |
| PPMO#11 | LpxB | TAATCCGTCAG | 11 | TEG | (RXR)4XB | 23 |
| PPMO#12 | WaaG | GCCAGGGTCAT | 12 | TEG | (RXR)4XB | 23 |
| PPMO#13 | RpsJ6 | CCTCAGACTCC | 1 | TEG | RRRRRRG | 25 |
| PPMO#14 | RpsJ7 | GCATTTGACCT | 13 | TEG | (RXR)4XB | 23 |
| PPMO#15 | WaaA | GTACGGTTCAT | 14 | TEG | (RXR)4XB | 23 |
| PPMO#16 | WaaF | AGAATTCTCAT | 15 | TEG | (RXR)4XB | 23 |
| PPMO#17 | MurB | CAGTCGCCCCT | 16 | TEG | (RXR)4XB | 23 |
| PPMO#18 | MurE | AGGCTCATAGG | 17 | TEG | (RXR)4XB | 23 |
| PPMO#19 | AccB | CTAGCACTCCC | 18 | TEG | (RXR)4XB | 23 |
| PPMO#20 | FabZ | ATGTCCATCAT | 19 | TEG | (RXR)4XB | 23 |
| PPMO#21 | MurF | ACCTCCCAGGC | 20 | TEG | (RXR)4XB | 23 |
| PPMO#22 | MurG | GCAAAGTCCTC | 21 | TEG | (RXR)4XB | 23 |
| PPMO#41 | Scrambled1 | TCTCAGATGGT | 36 | TEG | (RXR)4XB | 23 |

*The thymines (T) can be uracils (U), and vice versa
X is 6-aminohexanoic acid; B is β-alanine
In some embodiments, the thymine bases of the targeting sequences of Table 3 are uracil bases.

In some embodiments, exemplary structures of oligonucleotides or a pharmaceutically acceptable salt thereof of the disclosure may be represented by:

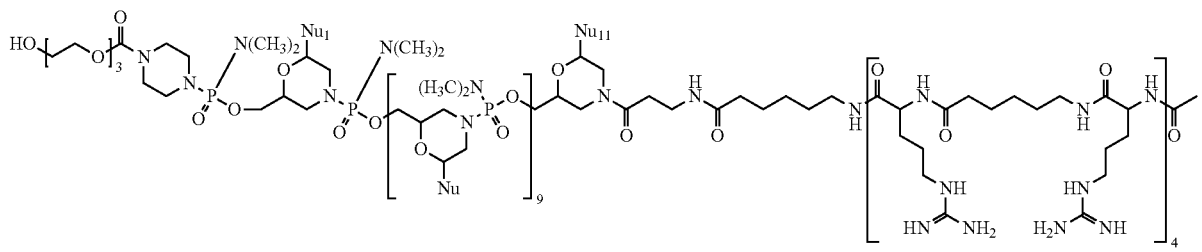

wherein the targeting sequence is selected from the group consisting of:

a)
(SEQ ID NO: 2)
GTT GTT TGA TC;

b)
(SEQ ID NO: 3)
TTC TCT CCT TT;

c)
(SEQ ID NO: 4)
CAT ACC TTG TT;

d)
(SEQ ID NO: 5)
CTC TAG ACA TG;

e)
(SEQ ID NO: 6)
AGC ACC CTC AT;

f)
(SEQ ID NO: 7)
TGA CTC TCC TC;

g)
(SEQ ID NO: 8)
CCA CCT CCA GG;

h)
(SEQ ID NO: 9)
AGG CTT CCG TC;

i)
(SEQ ID NO: 10)
ATC AAA CTC AT;

j)
(SEQ ID NO: 11)
TAA TCC GTC AG;

k)
(SEQ ID NO: 12)
GCC AGG GTC AT;

l)
(SEQ ID NO: 13)
GCA TTT GAC CT;

m)
(SEQ ID NO: 14)
GTA CGG TTC AT;

n)
(SEQ ID NO: 15)
AGA ATT CTC AT;

o)
(SEQ ID NO: 16)
CAG TCG CCC CT;

p)
(SEQ ID NO: 17)
AGG CTC ATA GG;

q)
(SEQ ID NO: 18)
CTA GCA CTC CC;

r)
(SEQ ID NO: 19)
ATG TCC ATC AT;

s)
(SEQ ID NO: 20)
ACC TCC CAG GC;

t)
(SEQ ID NO: 21)
GCA AAG TCC TC;
and u)
(SEQ ID NO: 35)
CTC ATA CCT TG wherein thymine bases may be uracil bases.

In certain embodiments, exemplary structures of an oligonucleotide or a pharmaceutically acceptable salt thereof of the disclosure may be represented by:

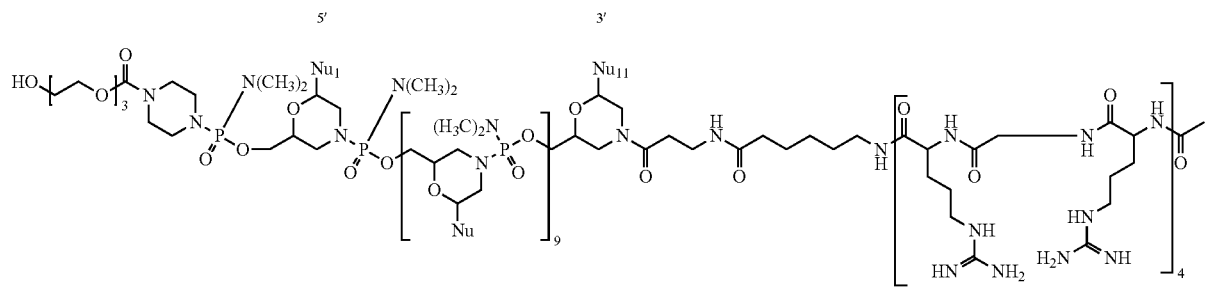

wherein the targeting sequence is CCT CAG ACT CC (SEQ ID NO: 1), wherein thymine bases may be uracil bases.

In some embodiments, an exemplary structure of an oligonucleotide or a pharmaceutically acceptable salt thereof of the disclosure may be represented by:

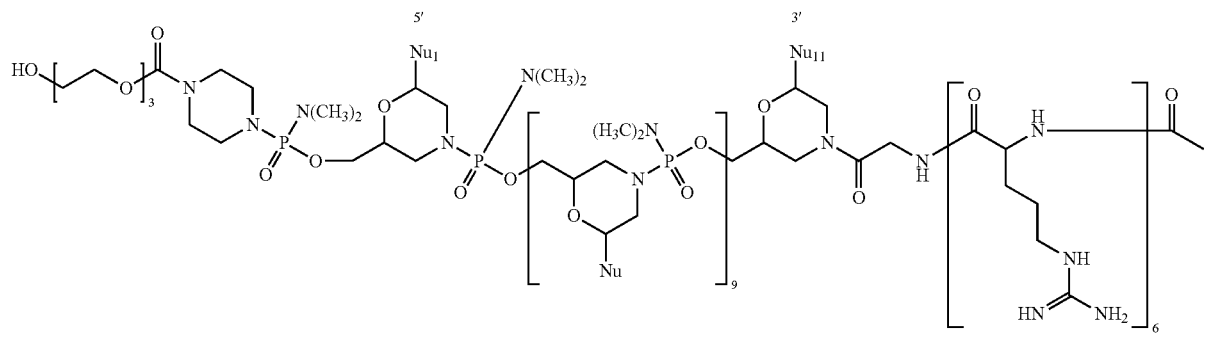

wherein the targeting sequence is CCT CAG ACT CC (SEQ ID NO: 1), wherein thymine bases may be uracil bases.

In some embodiments, the thymine bases of the targeting sequences of the above structures are uracil bases.

TABLE 4

Exemplary 5' CPP PPMO Compounds

| PPMO Name | Target Gene | Targeting Sequence (TS)* | TS SEQ ID NO: | 5' CPP/ Linker | 3' | CPP SEQ ID NO: |
|---|---|---|---|---|---|---|
| PPMO#23 | RpsJ | CCTCAGACTCC | 1 | (dRdFdF)3XB | COCH3 | 30 |
| PPMO#24 | RpsJ | CCTCAGACTCC | 1 | (dRXdR)4XB | COCH3 | 31 |
| PPMO#25 | RpsJ | CCTCAGACTCC | 1 | dR8B | COCH3 | 32 |
| PPMO#26 | RpsJ | CCTCAGACTCC | 1 | dR6G | COCH3 | 33 |
| PPMO#27 | RpsJ | CCTCAGACTCC | 1 | (dRdFdF)3dRXB | COCH3 | 34 |
| PPMO#29 | RpsJ | CCTCAGACTCC | 1 | (RXR)4XB | H | 23 |
| PPMO#30 | RpsJ | CCTCAGACTCC | 1 | R6G | H | 25 |
| PPMO#32 | RpsJ | GCATTTGACCT | 13 | (RXR)4XB | COCH3 | 23 |
| PPMO#33 | RpsJ | GCATTTGACCT | 13 | (RXR)4XB | H | 23 |
| PPMO#34 | RpsJ | GCATTTGACCT | 13 | R6G | H | 25 |
| PPMO#35 | AcpP | CTCATACCTTG | 35 | (RXR)4XB | H | 23 |
| PPMO#36 | AcpP | CTCATACCTTG | 35 | (RGR)4XB | H | 29 |
| PPMO#37 | AcpP | CTCATACCTTG | 35 | (RFR)4XB | H | 28 |
| PPMO#38 | LpxC | GTTGTTTGATC | 2 | (RXR)4XB | COCH3 | 23 |
| PPMO#39 | LpxC | GTTGTTTGATC | 2 | (RXR)4XB | H | 23 |
| PPMO#40 | LpxC | GTTGTTTGATC | 2 | R6G | H | 25 |
| PPMO#42 | Scrambled2 | ATCGTTGCATC | 37 | (RXR)4XB | H | 23 |
| PPMO#43 | Scrambled3 | TCTCAGATGGT | 36 | (RFR)4XB | H | 28 |

TABLE 4-continued

Exemplary 5' CPP PPMO Compounds

| PPMO Name | Target Gene | Targeting Sequence (TS)* | TS SEQ ID NO: | 5' CPP/ Linker | 3' | CPP SEQ ID NO: |
|---|---|---|---|---|---|---|
| PPMO#44 | Scrambled4 | TCTCAGATGGT | 36 | (RXR)4XB | H | 23 |
| PPMO#45 | Scrambled5 | TCTCAGATGGT | 36 | (RGR)4XB | COCH3 | 29 |
| PPMO#46 | Scrambled6 | TCTCAGATGGT | 36 | (dRXdR)4XB | COCH3 | 31 |

*The thymines (T) can be uracils (U), and vice versa
X is 6-aminohexanoic acid; B is β-alanine In some embodiments, the thymine bases of the targeting sequences of Table 4 are uracil bases.

In some embodiments, exemplary structures of oligonucleotides or a pharmaceutically acceptable salt thereof of the disclosure may be represented by:

wherein the targeting sequence is CCT CAG ACT CC (SEQ ID NO: 1), wherein thymine bases may be uracil bases.

In some embodiments, the thymine bases of the targeting sequences of the above structures are uracil bases.

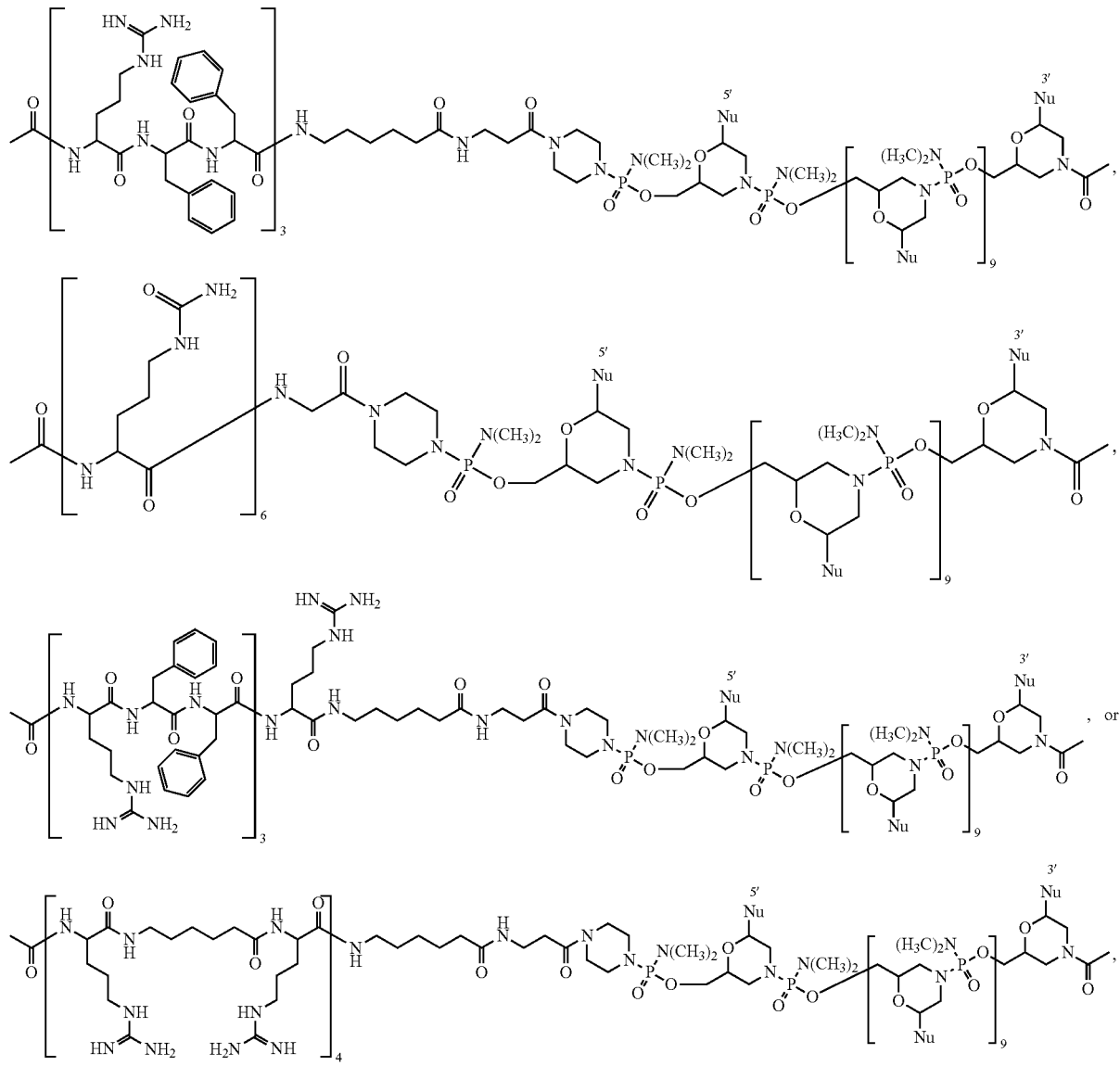

The antisense oligonucleotides can be prepared by stepwise solid-phase synthesis, employing methods known in the art and described in the references cited herein.

Methods of Use and Formulations

Embodiments of the present disclosure include methods of using the antisense oligonucleotides described herein to reduce the expression and activity of one or more bacterial proteins involved in a biochemical pathway and/or cellular process. Certain embodiments include methods of using the antisense oligonucleotides to reduce replication, proliferation, virulence factors, or growth of bacteria, for example, to treat bacterial infections in a subject, either alone or in combination with one or more additional antimicrobial agents. In some instances, the antisense oligonucleotides increase the susceptibility of the bacterium to one or more antibiotics.

Also included are pharmaceutical compositions comprising the antisense oligonucleotides, typically in combination with a pharmaceutically-acceptable carrier. In some instances, the pharmaceutical compositions comprise one or more additional compounds, for example, one or more additional antibiotics. The methods provided herein can be practiced in vitro or in vivo.

For example, certain embodiments include methods of treating a bacterial infection in a subject, comprising administering to a subject in need thereof (e.g., subject having or at risk for having a bacterial infection) an antisense oligonucleotide or pharmaceutical composition described herein. Also included are methods of reducing virulence and/or biofilm formation of a bacteria or bacterium which comprises a gene encoding a virulence factor, comprising contacting the bacteria or bacterium with an antisense oligonucleotide described herein.

In some embodiments, the bacterium is selected from the genus *Pseudomonas*. *Pseudomonas* is a genus of Gram-negative aerobic gammaproteobacteria, belonging to the family Pseudomonadaceae. *Pseudomonas* spp. are naturally resistant to penicillin and the majority of related beta-lactam antibiotics, but some are sensitive to piperacillin, imipenem, ticarcillin, and/or ciprofloxacin. Aminoglycosides such as tobramycin, gentamicin, and amikacin are other potential microbial agents for the treatment of *Pseudomonas* infections. *Pseudomonas aeruginosa* is ubiquitous in the environment and is a major opportunistic pathogen in the hospital setting. It is also the major pathogen associated with lung infections in cystic fibrosis (CF). CF patients become infected with strains of *P. aeruginosa* from the environment, after which they evolve in the CF lung. Eighty percent of CF patients are infected with *P. aeruginosa* by adulthood and chronic lung infections with this pathogen are the primary cause of morbidity and mortality. Currently, complete eradication of *P. aeruginosa* is rarely achieved. Chronic infection isolates can have phenotypes distinct from those in the environment or those that cause acute infections including expression of the mucoid exopolysaccharide alginate (responsible for the formation of antibiotic recalcitrant biofilms), defective lipopolysaccharide O antigen synthesis, loss of flagella and/or type IV pili, and decreased exoenzyme production. Multi-drug resistant isolates of *P. aeruginosa* are now common in CF leaving virtually no therapeutic options.

Thus, in some embodiments, the bacterium is any of the foregoing members of the genera *Pseudomonas*. In specific embodiments, the bacterium is one or more of *Pseudomonas aeruginosa*.

In certain embodiments, the bacterium is multi-drug resistance (MDR) bacteria or bacterium. Multiple drug resistance (MDR), multi-drug resistance or multiresistance is a condition enabling disease-causing microorganisms (bacteria, viruses, fungi or parasites) to resist distinct antimicrobials such as antibiotics, antifungal drugs, antiviral medications, antiparasitic drugs, and others. In particular embodiments, the bacterium is extensively-drug resistant (XDR) or pan-drug resistant (PDR). In some embodiments, the bacterium is an extended-spectrum β-lactamase (ESBLs) producing Gram-negative bacteria, or a multi-drug-resistant gram negative rod (MDR GNR) MDRGN bacteria. In specific embodiments, the bacterium is MDR *Pseudomonas aeruginosa*.

In some embodiments in a method of treating a *Pseudomonas aeruginosa* infection, the targeting sequence is selected from Table 1, a fragment of at least 10 contiguous nucleotides of a targeting sequence in Table 1, or variant having at least 80% sequence identity to a targeting sequence in Table 1, wherein the thymine bases may be uracil bases.

In some embodiments in a method of treating a *Pseudomonas aeruginosa* infection, the compound is of the formula:

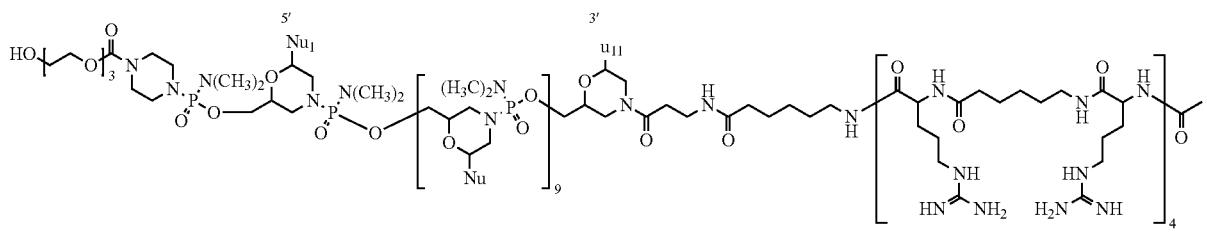

or a pharmaceutically acceptable salt thereof, wherein the targeting sequence, from 5' to 3', is selected from the group consisting of:

a)
(SEQ ID NO: 2)
GTT GTT TGA TC;

b)
(SEQ ID NO: 3)
TTC TCT CCT TT;

c)
(SEQ ID NO: 4)
CAT ACC TTG TT;

d)
(SEQ ID NO: 5)
CTC TAG ACA TG;

-continued e)
AGC ACC CTC AT; (SEQ ID NO: 6)

f)
TGA CTC TCC TC; (SEQ ID NO: 7)

g)
CCA CCT CCA GG; (SEQ ID NO: 8)

h)
AGG CTT CCG TC; (SEQ ID NO: 9)

i)
ATC AAA CTC AT; (SEQ ID NO: 10)

j)
TAA TCC GTC AG; (SEQ ID NO: 11)

k)
GCC AGG GTC AT; (SEQ ID NO: 12)

l)
GCA TTT GAC CT; (SEQ ID NO: 13)

m)
GTA CGG TTC AT; (SEQ ID NO: 14)

-continued n)
AGA ATT CTC AT; (SEQ ID NO: 15)

o)
CAG TCG CCC CT; (SEQ ID NO: 16)

p)
AGG CTC ATA GG; (SEQ ID NO: 17)

q)
CTA GCA CTC CC; (SEQ ID NO: 18)

r)
ATG TCC ATC AT; (SEQ ID NO: 19)

s)
ACC TCC CAG GC; (SEQ ID NO: 20)

t)
GCA AAG TCC TC; (SEQ ID NO: 21)
and u)
CTC ATA CCT TG, (SEQ ID NO: 35)

wherein thymine bases may be uracil bases.

In certain embodiments, the compound is selected from:

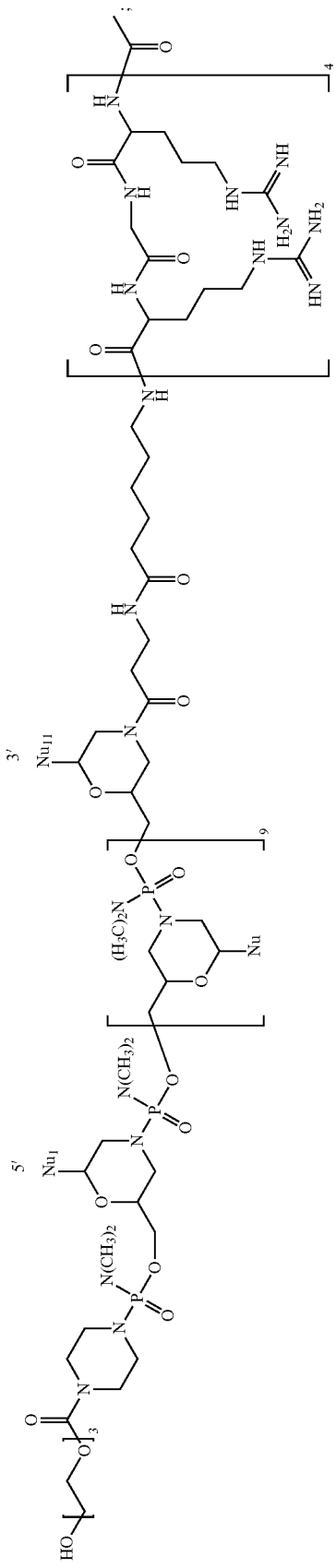
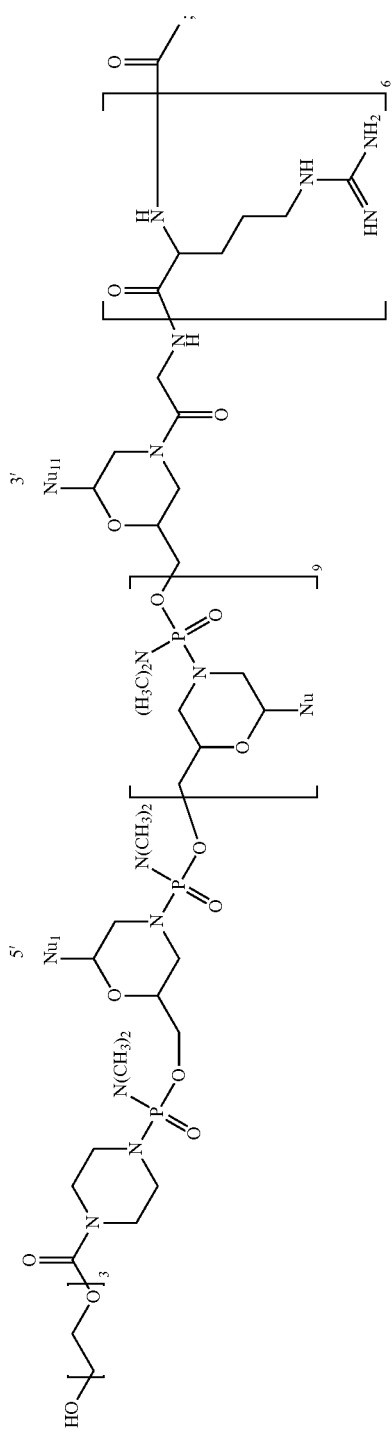

-continued
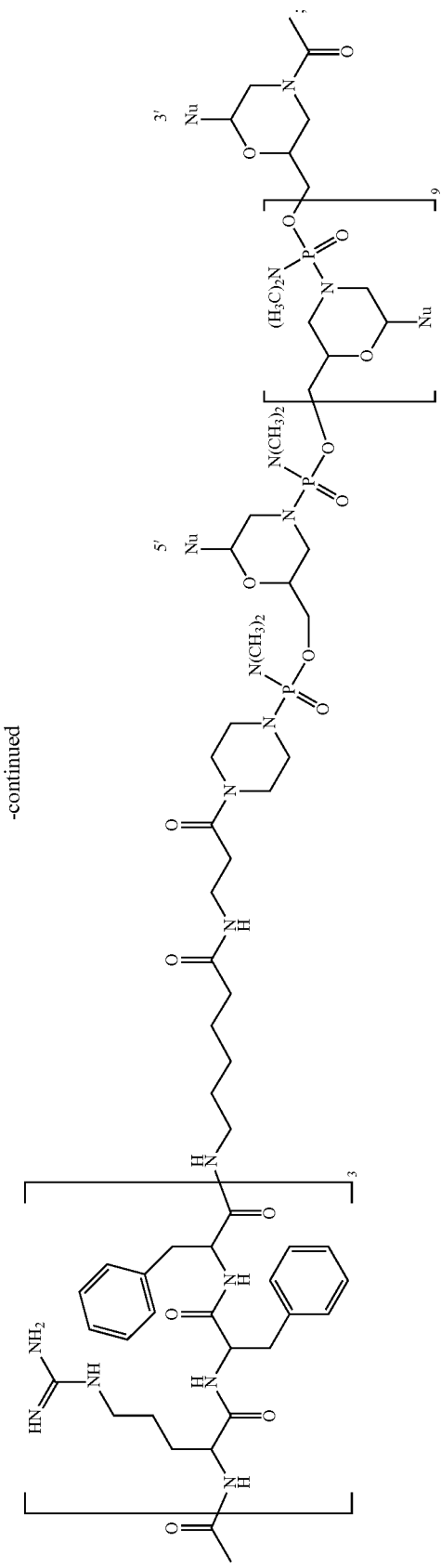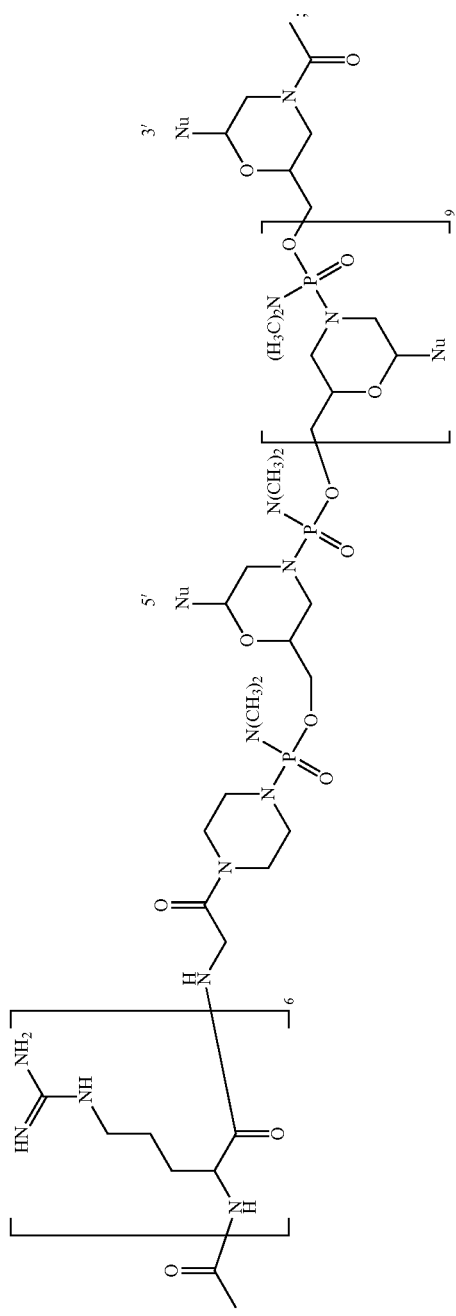

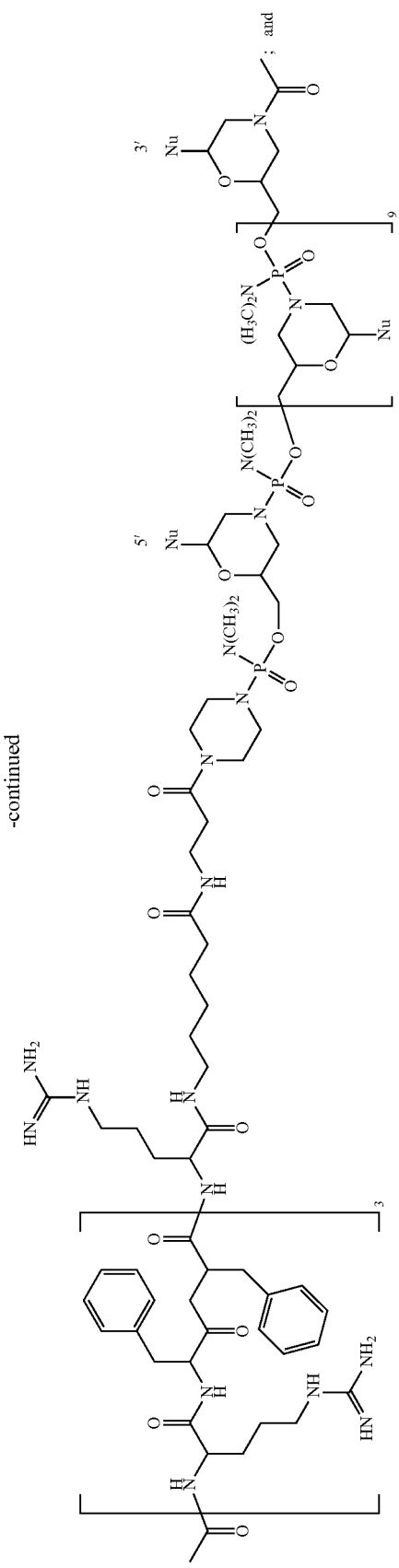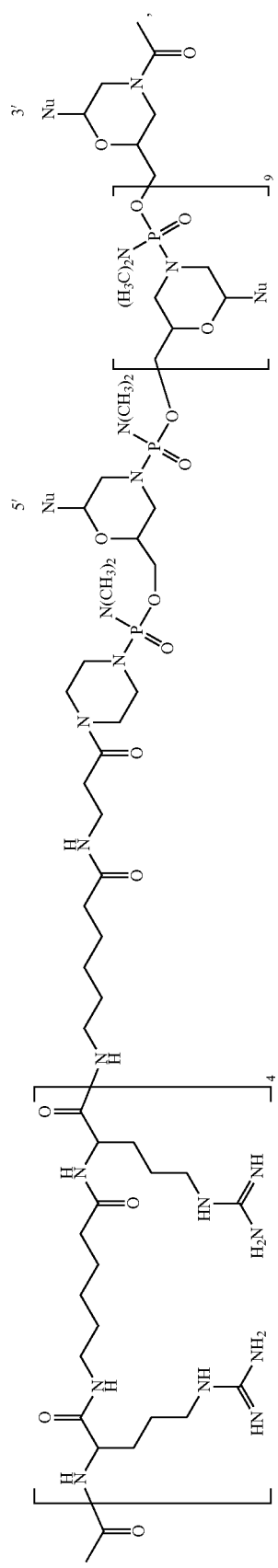

or a pharmaceutically acceptable salt thereof,
wherein the targeting sequence, from 5' to 3', is CCT CAG ACT CC (SEQ ID NO: 1), wherein thymine bases may be uracil bases.

In certain embodiments, the compound is of the formula:

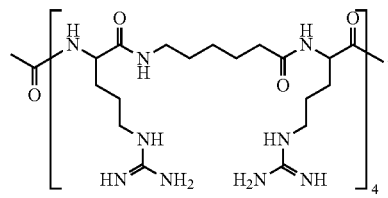 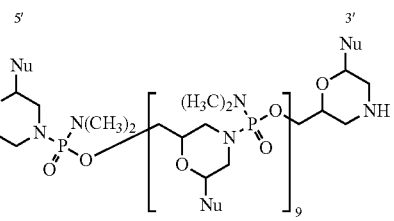

wherein the targeting sequence, from 5' to 3', is GTC GAA CCA AT (SEQ ID NO: 22), wherein thymine bases may be uracil bases.

In some embodiments in a method of treating a *Pseudomonas aeruginosa* infection, the pharmaceutical composition further comprises a second compound selected from the group consisting of polymyxin E (PME), polymyxin B (PMB), polymyxin B nonapeptide (PMBN), polymyxin E nonapeptide, a pharmaceutically acceptable salt of any of the foregoing, and combinations thereof.

In some embodiments, the second compound is PME.

In some embodiments, the ratio of compound (I) to PME is selected from about 1:1, 2:1, 4:1, 8:1, 10:1, 12:1, 14:1, 16:1, 18:1, and 20:1.

In some embodiments, the second compound is PMBN.

In some embodiments, the ratio of compound (I) to PMBN is selected from about 1:1, 2:1, 4:1, 8:1, 10:1, 12:1, 14:1, 16:1, 18:1, and 20:1.

In some embodiments, the amount of the second compound present in the pharmaceutical composition is below a therapeutic level for antibiotic activity of the second compound in treating the *Pseudomonas aeruginosa* infection.

In some embodiments in the method of treating a *Pseudomonas aeruginosa* infection, the method further comprises the step of administering ampicillin to the patient.

In some embodiments, the ampicillin is co-administered with the pharmaceutical composition.

In some embodiments, the pharmaceutical composition further comprises ampicillin.

In some embodiments in the method of treating a *Pseudomonas aeruginosa* infection, the patient is immunocompromised.

In some embodiments in the method of treating a *Pseudomonas aeruginosa* infection, the patient has or is at risk for having cystic fibrosis (CF).

In some embodiments in the method of treating a *Pseudomonas aeruginosa* infection, the thymine bases are uracil bases.

As noted above, the bacteria or bacterium described herein can comprise (e.g., encode) one or more virulence factors such as antibiotic resistance genes. One example of an antibiotic resistance gene (and their related proteins) includes beta-lactamases, which can enzymatically deactivate certain antimicrobial agents. In particular embodiments, the antibiotic resistance gene is AmpR, a global transcriptional regulator of the β-lactamase AmpC.

In some of these and related embodiments, the subject or patient in need thereof has an underlying lung disease, such as cystic fibrosis (CF) or chronic granulomatous disease (CGD). In some embodiments, the subject or patient is immunocompromised. In specific embodiments, the subject or patient is immunocompromised and has an underlying lung disease, such as CF or CGD. Thus, certain embodiments include methods of treating a bacterial infection (e.g., *P. aeruginosa* infection) in a subject, where the subject has is or at risk for having a lung disease, for example, CF and/or CGD. Some embodiments include methods of treating a bacterial infection (e.g., *P. aeruginosa* infection) in an immunocompromised subject, for example, a subject that has or is at risk for having a lung disease such as CF and/or CGD.

In some embodiments, the antisense oligonucleotide reduces or inhibits the growth of the bacterium. For instance, in some embodiments, the antisense oligonucleotide reduces growth of the bacterium by about or at least about 5, 10, 15, 20, 25, 30, 35, 40, 45, 50, 55, 60, 65, 70, 75, 80, 85, 90, 95, 100, 150, 200, 250, 300, 350, 400, 450, 500, 600, 700, 800, 900, or 1000% or more (including all integers and ranges in between), relative to a control (e.g., absence of the antisense oligonucleotide, scrambled oligonucleotide, prior to contacting with the oligonucleotide), or by about or at least about 2, 3, 4, 5, 6, 7, 8, 9, 10, 15, 20, 25, 30, 35, 40, 45, 50, 55, 60, 65, 70, 75, 80, 85, 90, 95, or 100-fold or more (including all integers and ranges in between), relative to a control. Bacterial growth can be measured in vitro (see, e.g., the Examples) or in vivo. In some embodiments, as described herein, the antisense oligonucleotide is employed in combination with one or more antimicrobial agents.

In some embodiments, the antisense oligonucleotide reduces ribosomal protein (e.g., RpsJ, RpmB) levels in the bacterium by about or at least about 5, 10, 15, 20, 25, 30, 35, 40, 45, 50, 55, 60, 65, 70, 75, 80, 85, 90, 95, 100, 150, 200, 250, 300, 350, 400, 450, 500, 600, 700, 800, 900, or 1000% or more (including all integers and ranges in between), relative to a control, or by at least about 2, 3, 4, 5, 6, 7, 8, 9, 10, 15, 20, 25, 30, 35, 40, 45, 50, 55, 60, 65, 70, 75, 80, 85, 90, 95, or 100-fold or more (including all integers and ranges in between), relative to a control. In particular embodiments, the antisense oligonucleotide that reduces ribosomal protein levels is targeted against RpsJ and/or RpmB, and the bacterium is a *Pseudomonas* species, for example, *Pseudomonas aeruginosa*, which comprises or expresses RpsJ and/or RpmB. This is an exemplary bacterial species and it is expected that any bacterium expressing the RpsJ and/or RpmB genes is susceptible to the compounds and methods described herein. Ribosomal protein levels can be measured according to routine techniques in the art.

In some embodiments, the antisense oligonucleotide reduces lipopolysaccharide (LPS) biosynthesis and/or LPS levels in a bacterium relative to a control (e.g., absence of the oligonucleotide). For instance, in some embodiments, the antisense oligonucleotide reduces LPS biosynthesis and/or LPS levels by at least about 5, 10, 15, 20, 25, 30, 35, 40, 45, 50, 55, 60, 65, 70, 75, 80, 85, 90, 95, 100, 150, 200, 250, 300, 350, 400, 450, 500, 600, 700, 800, 900, or 1000% or more (including all integers and ranges in between), relative to a control, or by at least about 2, 3, 4, 5, 6, 7, 8, 9, 10, 15, 20, 25, 30, 35, 40, 45, 50, 55, 60, 65, 70, 75, 80, 85, 90, 95, or 100-fold or more (including all integers and ranges in between), relative to a control. In particular embodiments, the antisense oligonucleotide that reduces LPS biosynthesis and/or LPS levels is targeted against LpxC, WaaC, WaaG, WaaA, WaaF, LpxA and/or LpxB, and the bacterium is an *Pseudomonas* species, for example, *Pseudomonas aeruginosa*, which comprises or expresses LpxC, WaaC, WaaG, WaaA, WaaF, LpxA and/or LpxB. LPS biosynthesis and/or LPS levels can be measured according to routine techniques in the art.

In some embodiments, the methods are practiced in vivo, and comprise administering the antisense oligonucleotide to a subject in need thereof, for example, a subject in need thereof that is infected or at risk for being infected by one or more of the bacteria or bacterium described herein. The antisense oligonucleotides of the disclosure can thus be administered to subjects to treat (prophylactically or therapeutically) an infection by any of the bacteria or bacterium described herein. In conjunction with such treatment, pharmacogenomics (e.g., the study of the relationship between an individual's genotype/phenotype and that individual's response to a foreign compound or drug) may be considered. Differences in metabolism of therapeutics can lead to severe toxicity or therapeutic failure by altering the relation between dose and blood concentration of the pharmacologically active drug.

Thus, a physician or clinician may consider applying knowledge obtained in relevant pharmacogenomics studies in determining whether to administer a therapeutic agent as well as tailoring the dosage and/or therapeutic regimen of treatment with a therapeutic agent.

Effective delivery of the antisense oligonucleotide to the target nucleic acid is one aspect of treatment. Routes of antisense oligonucleotide delivery include, but are not limited to, various systemic routes, including oral and parenteral routes, e.g., intravenous, subcutaneous, intraperitoneal, and intramuscular, as well as inhalation, transdermal, and topical delivery. The appropriate route may be determined by one of skill in the art, as appropriate to the condition of the subject under treatment. Vascular or extravascular circulation, the blood or lymph system, and the cerebrospinal fluid are some non-limiting sites where the antisense oligonucleotides may be introduced. Direct CNS delivery may be employed, for instance, intracerebral, intraventricular, or intrathecal administration may be used as routes of administration.

In certain embodiments, the antisense oligonucleotides of the disclosure can be delivered by transdermal methods (e.g., via incorporation of the antisense oligonucleotides into, e.g., emulsions, with such antisense oligonucleotides optionally packaged into liposomes). Such transdermal and emulsion/liposome-mediated methods of delivery are described for delivery of antisense oligonucleotides in the art, e.g., in U.S. Pat. No. 6,965,025, the contents of which are incorporated in their entirety by reference herein.

The antisense oligonucleotides described herein may also be delivered via an implantable device. Design of such a device is an art-recognized process, with, e.g., synthetic implant design described in, e.g., U.S. Pat. No. 6,969,400, the contents of which are incorporated by reference.

Antisense oligonucleotides can be introduced into cells using art-recognized techniques (e.g., transfection, electroporation, fusion, liposomes, colloidal polymeric particles and viral and non-viral vectors as well as other means known in the art). The method of delivery selected will depend at least on the oligonucleotide chemistry, the cells to be treated and the location of the cells and will be apparent to the skilled artisan. For instance, localization can be achieved by liposomes with specific markers on the surface to direct the liposome, direct injection into tissue containing target cells, specific receptor-mediated uptake, or the like.

As known in the art, antisense oligonucleotides may be delivered using, e.g., methods involving liposome-mediated uptake, lipid conjugates, polylysine-mediated uptake, nanoparticle-mediated uptake, and receptor-mediated endocytosis, as well as additional non-endocytic modes of delivery, such as microinjection, permeabilization (e.g., streptolysin-O permeabilization, anionic peptide permeabilization), electroporation, and various non-invasive non-endocytic methods of delivery that are known in the art (see, e. g., Dokka and Rojanasakul, Advanced Drug Delivery Reviews 44:35-49, incorporated by reference in its entirety).

The antisense oligonucleotides may be administered in any convenient vehicle or carrier which is physiologically and/or pharmaceutically acceptable. Such a composition may include any of a variety of standard pharmaceutically acceptable carriers employed by those of ordinary skill in the art. Examples include, but are not limited to, saline, phosphate buffered saline (PBS), water, aqueous ethanol, emulsions, such as oil/water emulsions or triglyceride emulsions, tablets and capsules. The choice of suitable physiologically acceptable carrier will vary dependent upon the chosen mode of administration. "Pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

In certain embodiments, the disclosure provides for a pharmaceutical composition, comprising a compound of formula (I):

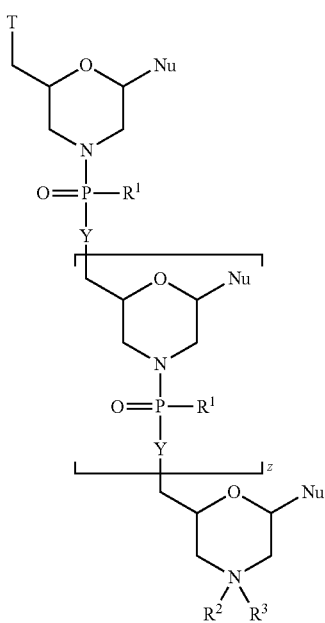
(I)

or a pharmaceutically acceptable salt thereof, wherein:

each Nu is a nucleobase which taken together forms a nucleobase sequence;

Z is an integer from 8 to 38;

T is selected from OH and a moiety of the formula:

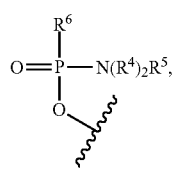

wherein:

each $R^4$ is independently selected from H and $C_1$-$C_6$ alkyl, and $R^5$ is selected from an electron pair and H, and $R^6$ is selected from —N($R^7$)CH$_2$C(O)NH$_2$, and a moiety of the formula:

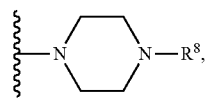

wherein:

$R^7$ is selected from H and $C_1$-$C_6$ alkyl; and $R^8$ is selected from G, —C(O)—$R^9$, acyl, trityl, and 4-methoxytrityl, wherein:

$R^9$ is of the formula —(O-alkyl)$_y$-OH wherein y is an integer from 3 to 10 and each of the y alkyl groups is independently selected from $C_2$-$C_6$ alkyl optionally containing one or more intervening oxygen radicals;

each instance of $R^1$ is —N($R^{10}$)$_2$$R^{11}$ wherein each $R^{10}$ is independently $C_1$-$C_6$ alkyl, and $R^{11}$ is selected from an electron pair and H;

$R^2$ is selected from the group consisting of H, G, acyl, trityl, 4-methoxytrityl, and a moiety of the formula:

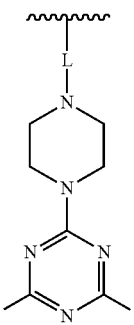

wherein,

L is selected from —C(O)(CH$_2$)$_6$C(O)— and —C(O)(CH$_2$)$_2$S$_2$(CH$_2$)$_2$C(O)—; and each $R^{12}$ is of the formula —(CH$_2$)$_2$OC(O)N($R^{26}$)$_2$ wherein each $R^{26}$ is of the formula (CH$_2$)$_6$NHC(=NH)NH$_2$; and $R^3$ is selected from the group consisting of an electron pair, H, and $C_1$-$C_6$ alkyl, wherein G is a cell penetrating peptide ("CPP") and linker moiety selected from the group consisting of —C(O)(CH$_2$)$_5$NH—CPP, —C(O)(CH$_2$)$_2$NH—CPP, —C(O)(CH$_2$)$_2$NHC(O)(CH$_2$)$_5$NH—CPP, —C(O)CH$_2$NH—CPP, and —C(O)CH(pyrrolidin-2-yl)NH—CPP wherein the CPP is attached to the linker moiety by an amide bond at the CPP carboxy terminus, with the proviso that up to one instance of G is present, and wherein the nucleobase sequence comprises a targeting sequence that is complementary to a *Pseudomonas aeruginosa* mRNA that encodes RpsJ, LpxC, FabG, AcpP, RpmB, WaaC, MraY, MurC, AccA, LpxA, LpxB, WaaG, WaaA, WaaF, MurB, MurE, AccB, FabZ, MurF, MurG, or AmpR; and a pharmaceutically acceptable carrier.

In certain embodiments, the targeting sequence is selected from Table 1, a fragment of at least 10 contiguous nucleotides of a targeting sequence in Table 1, or variant having at least 80% sequence identity to a targeting sequence in Table 1, wherein the thymine bases may be uracil bases.

In some embodiments, the compound is of the formula:

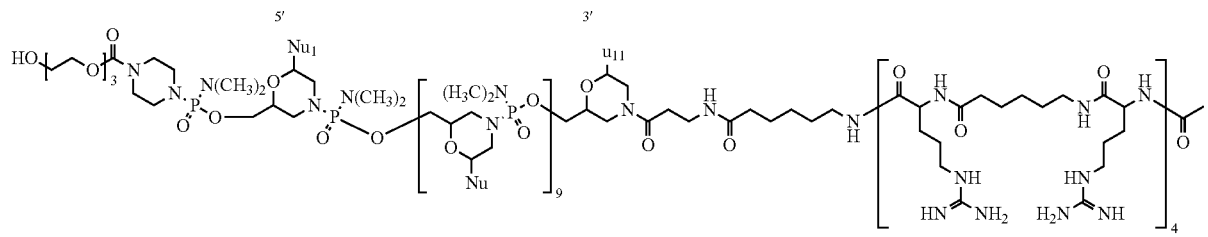

or a pharmaceutically acceptable salt thereof, wherein the targeting sequence, from 5' to 3', is selected from the group consisting of:

a)
(SEQ ID NO: 2)
GTT GTT TGA TC;

b)
(SEQ ID NO: 3)
TTC TCT CCT TT;

c)
(SEQ ID NO: 4)
CAT ACC TTG TT;

d)
(SEQ ID NO: 5)
CTC TAG ACA TG;

e)
(SEQ ID NO: 6)
AGC ACC TCA T;

f)
(SEQ ID NO: 7)
TGA CTC TCC TC;

g)
(SEQ ID NO: 8)
CCA CCT CCA GG;

h)
(SEQ ID NO: 9)
AGG CTT CCG TC;

i)
(SEQ ID NO: 10)
ATC AAA CTC AT;

j)
(SEQ ID NO: 11)
TAA TCC GTC AG;

k)
(SEQ ID NO: 12)
GCC AGG GTC AT;

l)
(SEQ ID NO: 13)
GCA TTT GAC CT;

m)
(SEQ ID NO: 14)
GTA CGG TTC AT;

n)
(SEQ ID NO: 15)
AGA ATT CTC AT;

o)
(SEQ ID NO: 16)
CAG TCG CCC CT;

p)
(SEQ ID NO: 17)
AGG CTC ATA GG;

q)
(SEQ ID NO: 18)
CTA GCA CTC CC;

r)
(SEQ ID NO: 19)
ATG TCC ATC AT;

s)
(SEQ ID NO: 20)
ACC TCC CAG GC;

t)
(SEQ ID NO: 21)
GCA AAG TCC TC;
and u)
(SEQ ID NO: 35)
CTC ATA CCT TG, wherein thymine bases may be uracil bases.

In some embodiments, the compound is selected from:

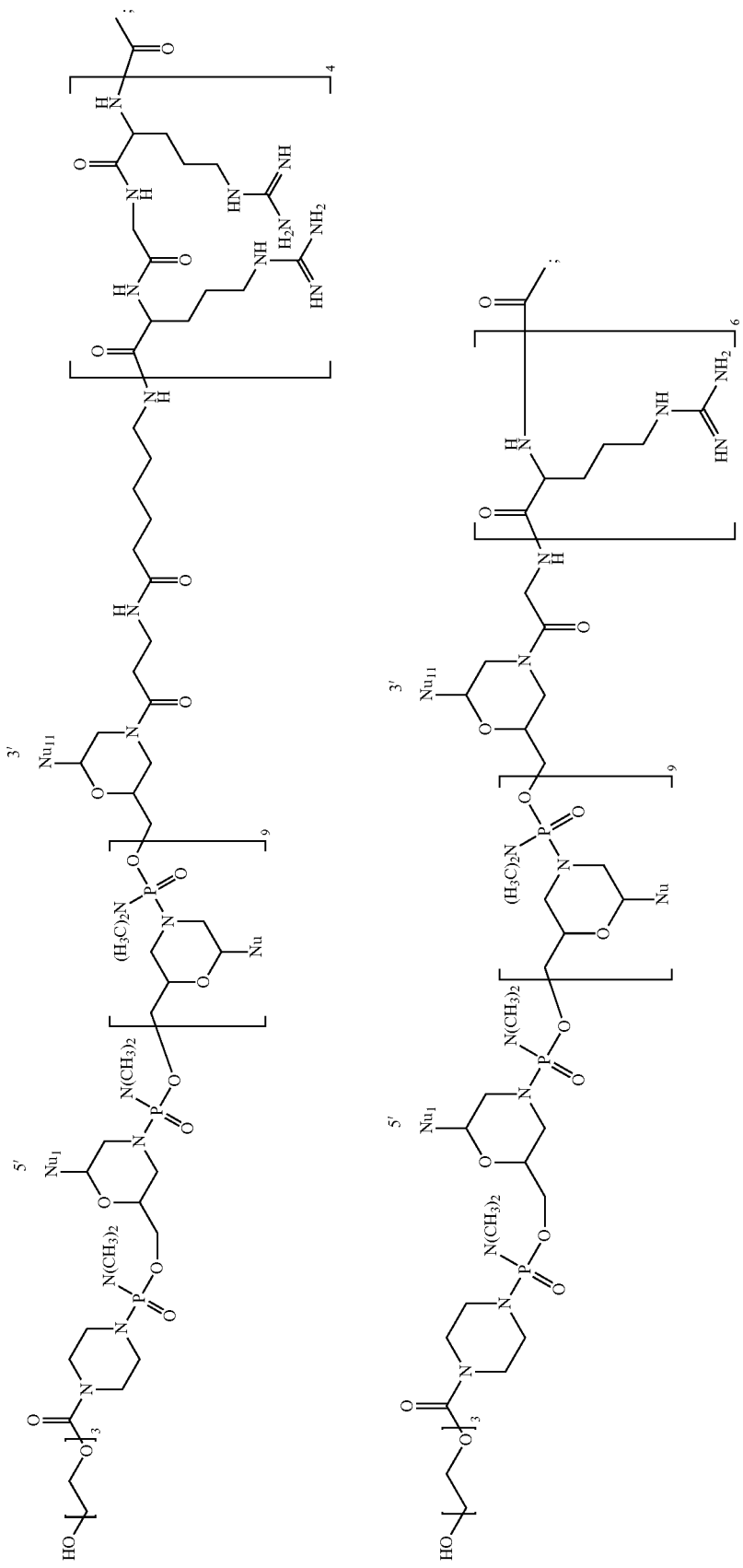

-continued
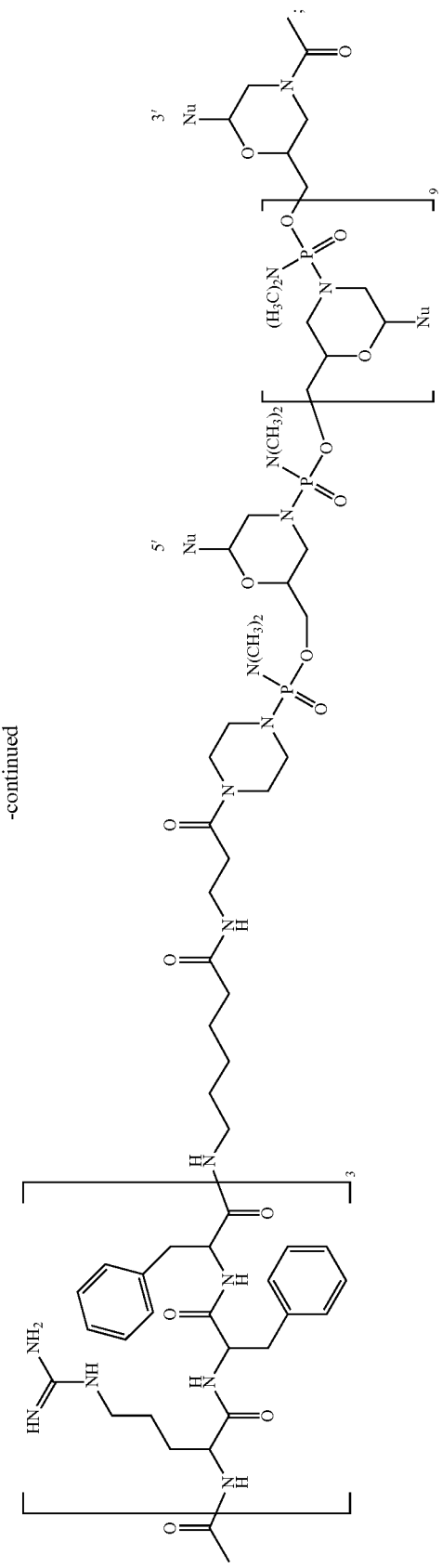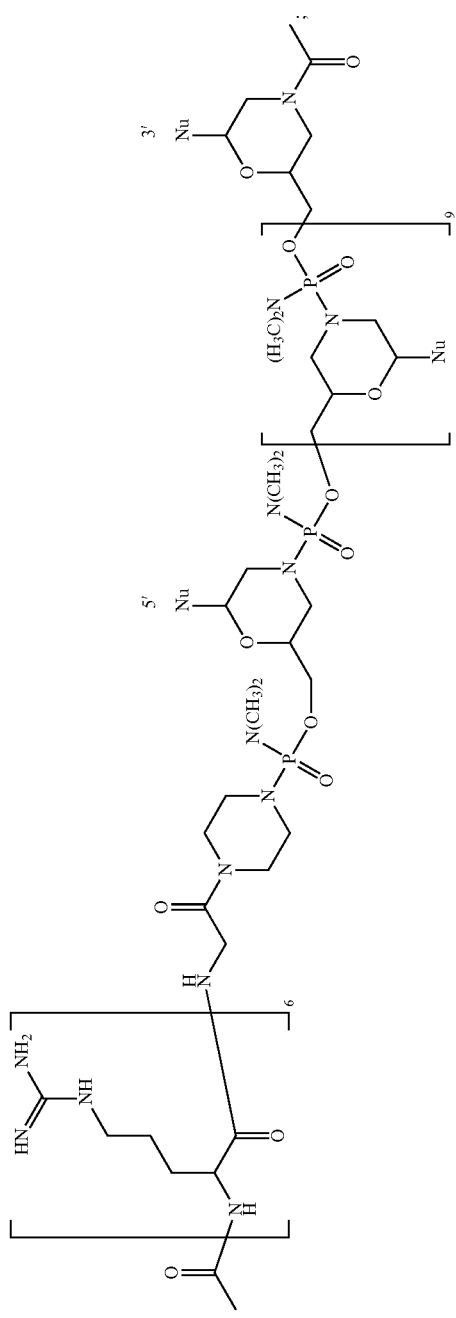

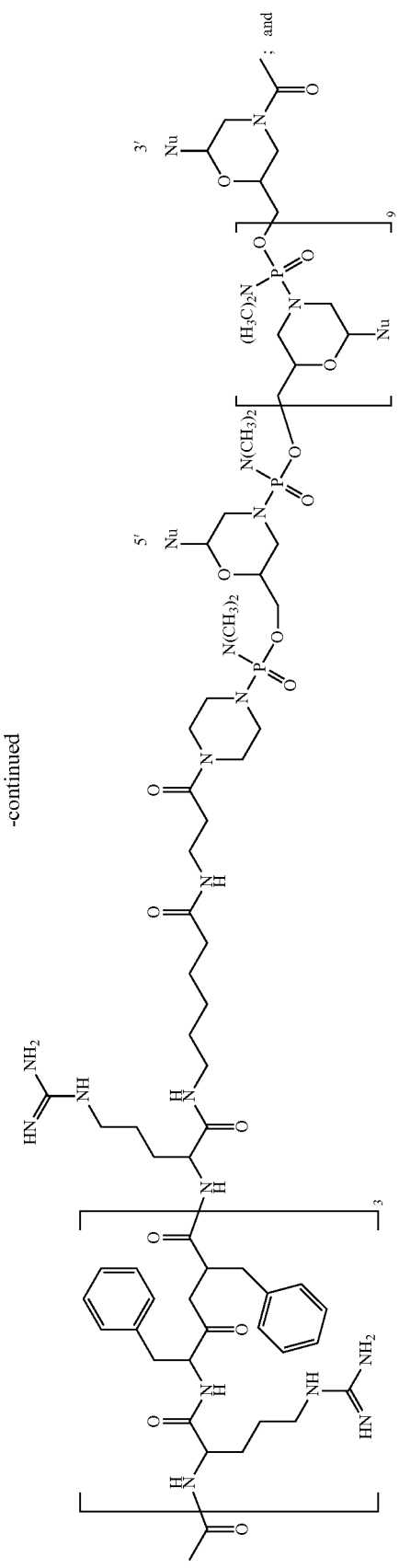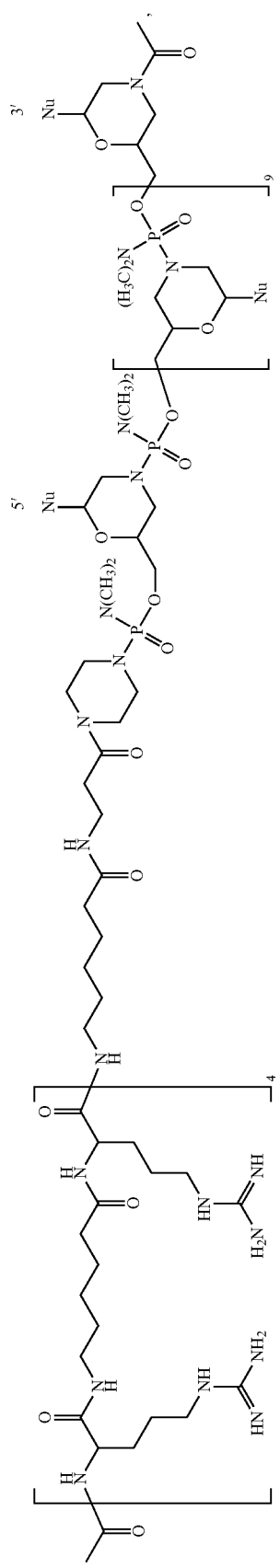

or a pharmaceutically acceptable salt thereof,
wherein the targeting sequence, from 5' to 3', is CCT CAG ACT CC (SEQ ID NO: 1), wherein thymine bases may be uracil bases.

In certain embodiments, the compound is of the formula:

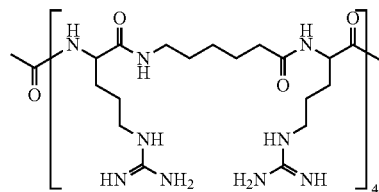 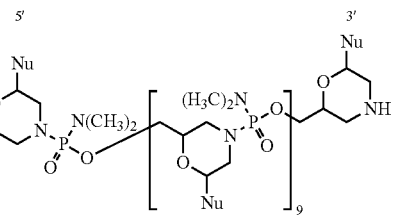

wherein the targeting sequence, from 5' to 3', is GTC GAA CCA AT (SEQ ID NO: 22), wherein thymine bases may be uracil bases.

In certain embodiments, the disclosure provides for a pharmaceutical composition further comprising a second compound selected from the group consisting of polymyxin E (PME), polymyxin B (PMB), polymyxin B nonapeptide (PMBN), polymyxin E nonapeptide, a pharmaceutically acceptable salt of any of the foregoing, and combinations thereof.

In some embodiments, the second compound is PME.

In some embodiments, the ratio of compound (I) to PME is selected from about 1:1, 2:1, 4:1, 8:1, 10:1, 12:1, 14:1, 16:1, 18:1, and 20:1.

In some embodiments, the second compound is PMBN.

In some embodiments, the ratio of compound (I) to PMBN is selected from about 1:1, 2:1, 4:1, 8:1, 10:1, 12:1, 14:1, 16:1, 18:1, and 20:1.

In some embodiments, in the pharmaceutical composition of the present disclosure, the thymine bases are uracil bases.

The compounds (e.g., antisense oligonucleotides, antimicrobial agents) described herein may generally be utilized as the free acid or free base. Alternatively, the compounds of this disclosure may be used in the form of acid or base addition salts. Acid addition salts of the free amino compounds of the present disclosure may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids.

Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" is intended to encompass any and all acceptable salt forms.

In addition, prodrugs are also included within the context of this disclosure. Prodrugs are any covalently bonded carriers that release a compound in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this disclosure wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the antisense oligonucleotides of the disclosure. Further, in the case of a carboxylic acid (—COOH), esters may be employed, such as methyl esters, ethyl esters, and the like.

In some instances, liposomes may be employed to facilitate uptake of the antisense oligonucleotide into cells (see, e.g., Williams, S. A., Leukemia 10(12):1980-1989, 1996; Lappalainen et al., Antiviral Res. 23:119, 1994; Uhlmann et al., antisense oligonucleotides: a new therapeutic principle, Chemical Reviews, Volume 90, No. 4, 25 pages 544-584, 1990; Gregoriadis, G., Chapter 14, Liposomes, Drug Carriers in Biology and Medicine, pp. 287-341, Academic Press, 1979). Hydrogels may also be used as vehicles for antisense oligomer administration, for example, as described in WO 93/01286. Alternatively, the oligonucleotides may be administered in microspheres or microparticles. (See, e.g., Wu, G. Y. and Wu, C. H., J. Biol. Chem. 262:4429-4432, 30 1987). Alternatively, the use of gas-filled microbubbles complexed with the antisense oligomers can enhance delivery to target tissues, as described in U.S. Pat. No. 6,245,747. Sustained release compositions may also be used. These may include semipermeable polymeric matrices in the form of shaped articles such as films or microcapsules.

In certain embodiments, the antisense oligonucleotide is administered to a mammalian subject, e.g., human or domestic animal, exhibiting the symptoms of a bacterial infection (e.g., antibiotic resistance or MDR bacterial infection), in a suitable pharmaceutical carrier. In some aspects, the subject is a human subject, e.g., a patient diagnosed as having a bacterial infection. In particular embodiments, the antisense oligonucleotide is contained in a pharmaceutically acceptable carrier, and is delivered orally. In some embodiments, the antisense oligonucleotide is contained in a pharmaceutically acceptable carrier, and is delivered intravenously (i.v.).

In some embodiments, the antisense oligonucleotide is administered in an amount and manner effective to result in a peak blood concentration of at least 200-400 nM antisense oligonucleotide. Typically, one or more doses of antisense oligonucleotide are administered, generally at regular intervals, for a period of about one to two weeks. Certain doses for oral administration are from about 1-1000 mg oligomer per 70 kg. In some cases, doses of greater than 1000 mg oligomer/patient may be necessary. For i.v. administration, some doses are from about 0.5 mg to 1000 mg oligomer per 70 kg. The antisense oligonucleotide may be administered at regular intervals for a short time period, e.g., daily for two weeks or less. However, in some cases the antisense oligonucleotide is administered intermittently over a longer period of time. Administration may be followed by, or concurrent with, administration of an antimicrobial (e.g., antibiotic) or other therapeutic treatment, as described herein. The treatment regimen may be adjusted (dose, frequency, route, etc.) as indicated, based on the results of immunoassays, other biochemical tests and physiological examination of the subject under treatment.

An effective in vivo treatment regimen using the antisense oligonucleotides of the disclosure may vary according to the duration, dose, frequency and route of administration, as well as the condition of the subject under treatment (i.e., prophylactic administration versus administration in response to localized or systemic infection). Accordingly, such in vivo therapy will often include monitoring by tests appropriate to the particular type of disorder or bacterial infection under treatment, and corresponding adjustments in the dose or treatment regimen, in order to achieve an optimal therapeutic outcome.

Treatment may be monitored, e.g., by general indicators of disease known in the art. The efficacy of an in vivo administered antisense oligonucleotide of the disclosure may be determined from biological samples (tissue, blood, urine etc.) taken from a subject prior to, during and subsequent to administration of the antisense oligonucleotide. Assays of such samples include (1) monitoring the presence or absence of heteroduplex formation with target and non-target sequences, using procedures known to those skilled in the art, e.g., an electrophoretic gel mobility assay; (2) monitoring the amount of a mutant mRNA in relation to a reference normal mRNA or protein as determined by standard techniques such as RT-PCR, Northern blotting, ELISA or Western blotting.

Combination Therapies

Certain embodiments include combination therapies, for example, the administration of antisense oligonucleotides in combination with antimicrobial agents such as antibiotics. Combination therapies can be employed, for example, to increase the sensitivity or susceptibility of a given bacteria to one or more antimicrobial agents, and thereby improve the therapeutic outcome (e.g., resolution of the infection). Likewise, certain combination therapies can be employed, for example, to reduce or reverse the antibiotic resistance of a given bacteria to one or more antimicrobial agents. In particular embodiments, the antisense oligonucleotide reduces the minimum inhibitory concentration (MIC) of an antibiotic against a bacterium. Also included are pharmaceutical compositions, as described herein, which comprise an antisense oligonucleotide and an antimicrobial agent such as an antibiotic. In particular embodiments, the antibiotic is a polymyxin, such as polymyxin B or polymyxin E (Colistin). In other embodiments, the antimicrobial agent is polymyxin B nonapeptide (PMBN) or polymyxin E nonapeptide (PMEN).

In some embodiments, the antisense oligonucleotide and the antimicrobial agent are administered separately. In certain embodiments, the antisense oligonucleotide and the antimicrobial agent are administered sequentially. In some embodiments, the antisense oligonucleotide and the antimicrobial agent are administered concurrently, for example, as part of the same or different pharmaceutical composition.

In certain embodiments, as noted above, the combination therapy includes the administration of one or more polymyxins. Polymyxin is a cationic, cyclic peptide antibiotic with a long hydrophobic tail derived from various species of *Paenibacillus* (*Bacillus*) *polymyxa*. It is a molecule that possesses both hydrophilic and hydrophobic properties. Polymyxins disrupt the structure of the bacterial cell membrane by interacting with its phospholipids. After binding to the lipid moiety, lipid A, of lipopolysaccharide (LPS) in the outer membrane of Gram-negative bacteria, polymyxins disrupt both the outer and inner membranes. The hydrophobic tail is important in causing membrane damage, suggesting a detergent-like mode of action. The resulting water uptake due to membrane permeabilization leads to cell death.

Polymyxins are produced by nonribosomal peptide synthetase systems in Gram-positive bacteria such as *Paenibacillus polymyxa* and are selectively toxic for Gram-negative bacteria due to their specificity for the LPS molecule that exists within many Gram-negative outer membranes. The great majority of isolates of *Escherichia coli*, *Klebsiella* spp., *Enterobacter* spp., *Pseudomonas aeruginosa*, and *Acinetobacter* spp., all important nosocomial pathogens, are usually susceptible to polymyxins. In addition, considerable activity exists against *Salmonella* spp., *Shigella* spp., *Pasteurella* spp., and *Haemophilus* spp. Several pathogens possess intrinsic resistance to the polymyxins: *Proteus* spp., *Providencia* spp., and most isolates of *Serratia* spp. In addition, isolates of *Brucella* spp., *Neisseria* spp., *Chromobacterium* spp., and *Burkholderia* spp. are resistant.

Five polymyxins were originally described (polymyxins A to E) and two, polymyxins B and E, have been used to treat Gram-negative bacterial infections. Polymyxins B and E differ by one amino acid change: Polymyxin B has D-phenylalanine and polymyxin E (Colistin) has D-leucine at position 6. Polymyxin B is composed of a number of related compounds including the major components polymyxins B1 and B2. Polymyxin M, known as "mattacin", is produced by *Paenibacillus kobensis* M. Studies have shown that its behavior was very similar to that observed in previous studies of polymyxin B, suggesting an identical mechanism of action. Thus, the methods and compositions provided herein can use or comprise any one or more of such polymyxins.

Gram-negative bacteria can develop resistance to polymyxins through various modifications of the LPS structure that inhibit the binding of polymyxins to LPS. Typically, polymyxins have less effect on Gram-positive organisms, and are sometimes combined with other agents (as with trimethoprim/polymyxin) to broaden the effective spectrum.

Polymyxin antibiotics are relatively toxic to the nervous system and kidneys, so they are usually used only as a last resort if modern antibiotics are ineffective or are contraindicated. Typical uses are for infections caused by strains of multiple drug-resistant *Pseudomonas aeruginosa* or carbapenemase-producing Enterobacteriaceae. Partly because of that toxicity, antisense oligonucleotides that reduce the MIC of a polymyxin can provide particular clinical benefits.

Polymyxins are not well-absorbed from the gastrointestinal tract, so certain combination therapies include routes of administration such as parenteral administration (often intravenously), or administration by inhalation (unless perhaps the targets are bacteria in the gastrointestinal tract). They are also used externally as a cream or drops to treat otitis externa (swimmers ear). Polymyxins are used in the topical first-aid preparation Neosporin.

In some embodiments in a pharmaceutical combination therapy for the treatment or prevention of a *Pseudomonas aeruginosa* infection, the targeting sequence is selected from Table 1, a fragment of at least 10 contiguous nucleotides of a targeting sequence in Table 1, or variant having at least 80% sequence identity to a targeting sequence in Table 1, wherein the thymine bases may be uracil bases.

In some embodiments in a pharmaceutical combination therapy for the treatment or prevention of a *Pseudomonas aeruginosa* infection, the compound is of the formula:

or a pharmaceutically acceptable salt thereof, wherein the targeting sequence, from 5' to 3', is selected from the group consisting of:

```
a)                                   (SEQ ID NO: 2)
GTT GTT TGA TC;

b)                                   (SEQ ID NO: 3)
TTC TCT CCT TT;

c)                                   (SEQ ID NO: 4)
CAT ACC TTG TT;

d)                                   (SEQ ID NO: 5)
CTC TAG ACA TG;

e)                                   (SEQ ID NO: 6)
AGC ACC CTC AT;

f)                                   (SEQ ID NO: 7)
TGA CTC TCC TC;

g)                                   (SEQ ID NO: 8)
CCA CCT CCA GG;

h)                                   (SEQ ID NO: 9)
AGG CTT CCG TC;

i)                                   (SEQ ID NO: 10)
ATC AAA CTC AT;
```

-continued

```
j)                                   (SEQ ID NO: 11)
TAA TCC GTC AG;

k)                                   (SEQ ID NO: 12)
GCC AGG GTC AT;
```

-continued

```
l)                                   (SEQ ID NO: 13)
GCA TTT GAC CT;

m)                                   (SEQ ID NO: 14)
GTA CGG TTC AT;

n)                                   (SEQ ID NO: 15)
AGA ATT CTC AT;

o)                                   (SEQ ID NO: 16)
CAG TCG CCC CT;

p)                                   (SEQ ID NO: 17)
AGG CTC ATA GG;

q)                                   (SEQ ID NO: 18)
CTA GCA CTC CC;

r)                                   (SEQ ID NO: 19)
ATG TCC ATC AT;

s)                                   (SEQ ID NO: 20)
ACC TCC CAG GC;

t)                                   (SEQ ID NO: 21)
GCA AAG TCC TC;
and u)                                   (SEQ ID NO: 35)
CTC ATA CCT TG,
``` wherein thymine bases may be uracil bases.

In some embodiments, the compound is selected from:

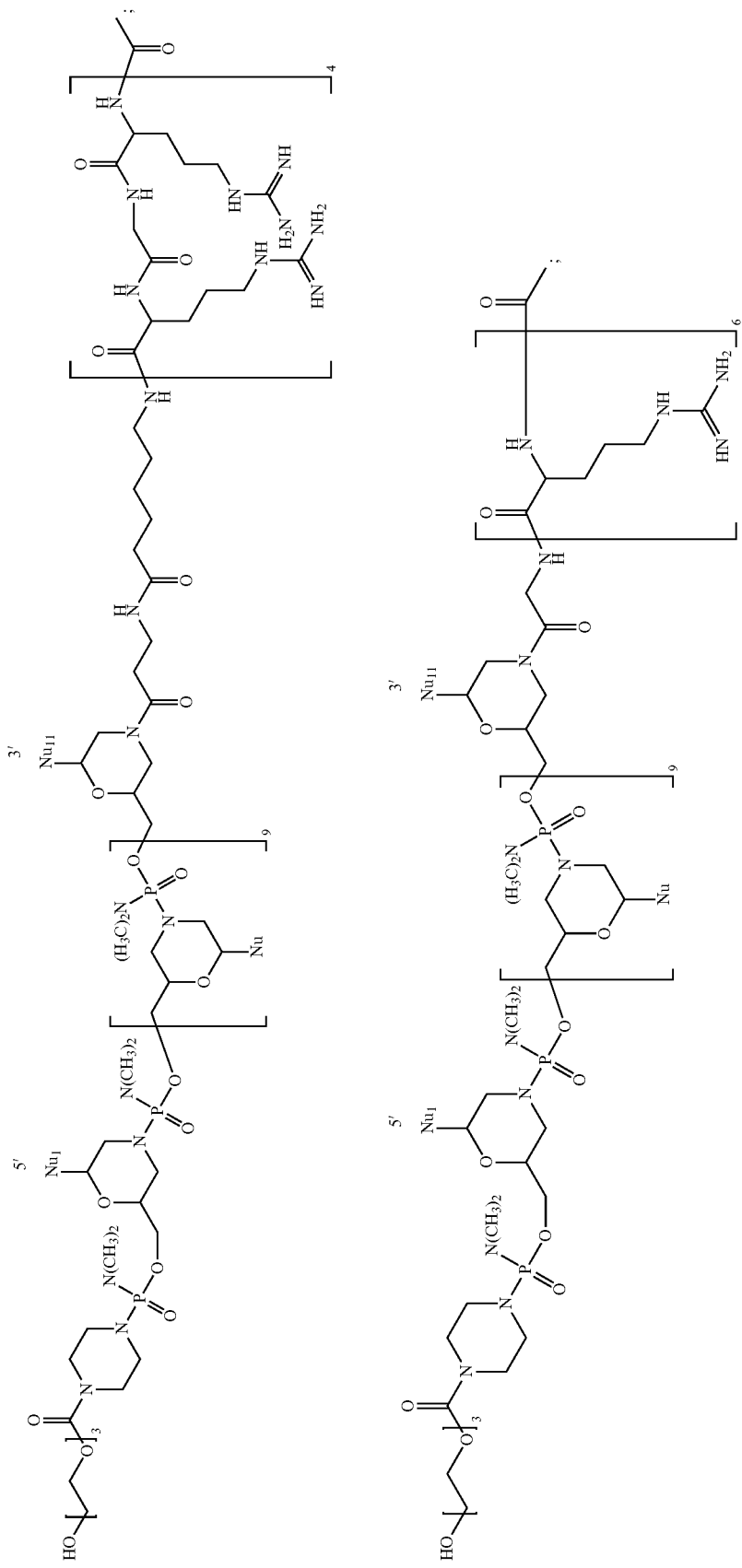

-continued
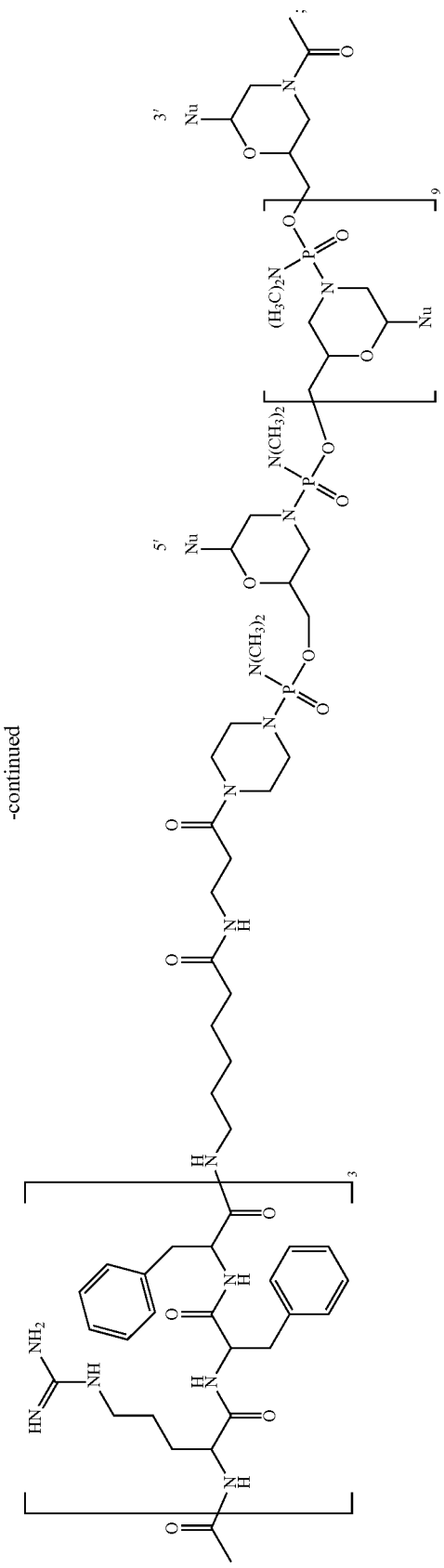
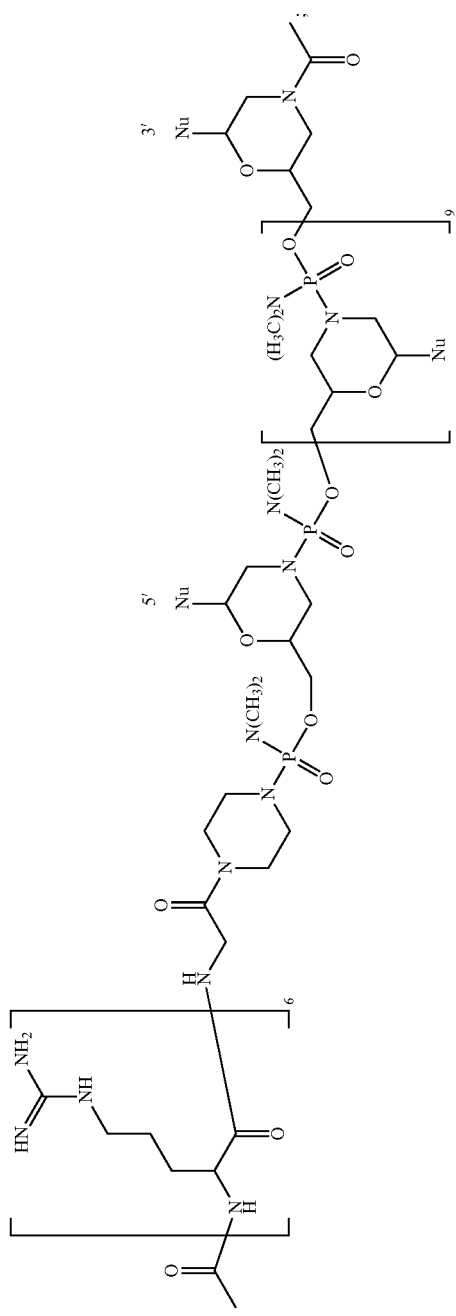

-continued
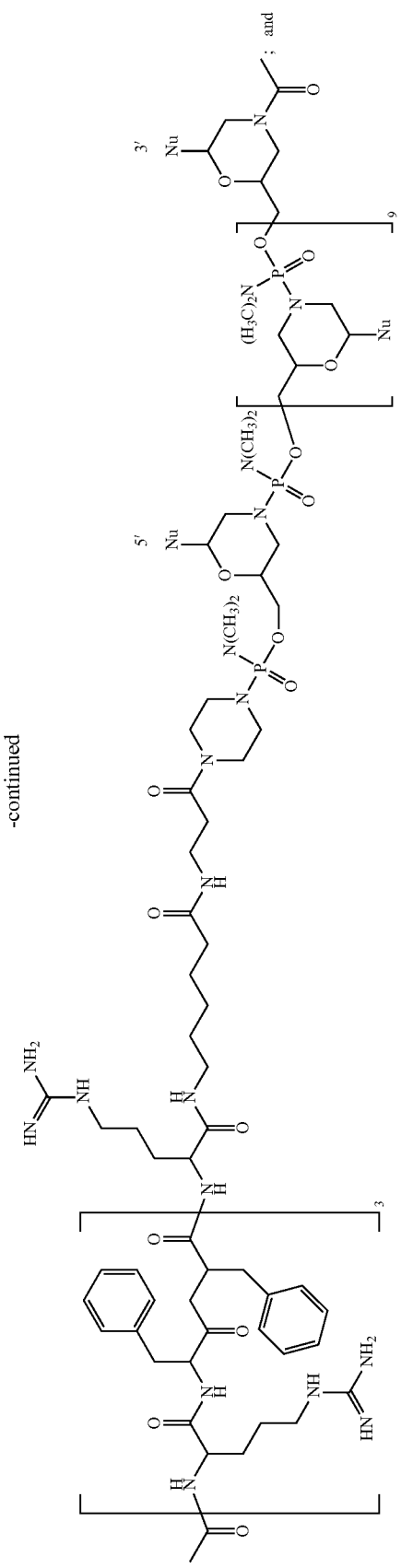
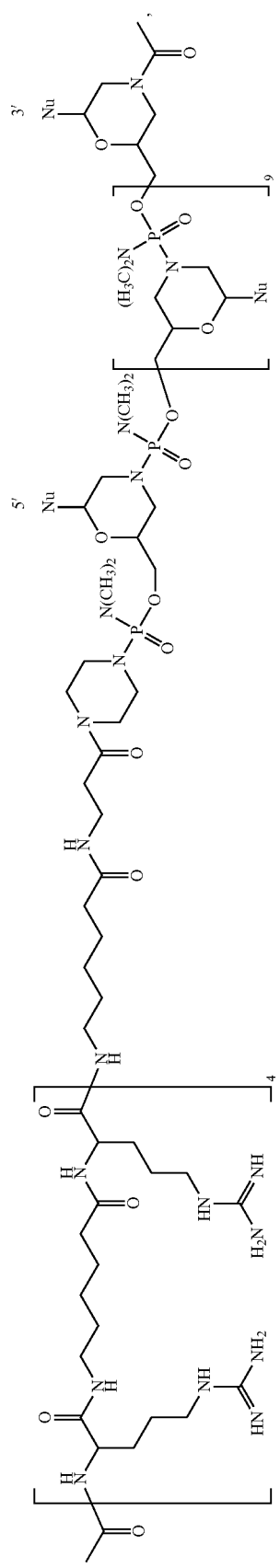

or a pharmaceutically acceptable salt thereof,
wherein the targeting sequence, from 5' to 3', is CCT CAG ACT CC (SEQ ID NO: 1), wherein thymine bases may be uracil bases.

In some embodiments, the compound is of the formula:

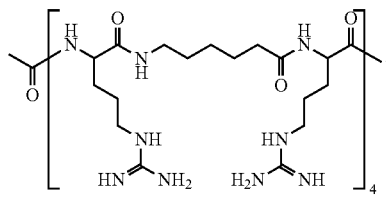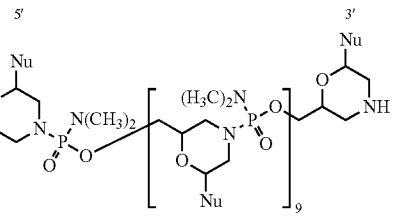

wherein the targeting sequence, from 5' to 3', is GTC GAA CCA AT (SEQ ID NO: 22), wherein thymine bases may be uracil bases.

In some embodiments, the second compound is PME.

In some embodiments, the ratio of compound (I) to PME is selected from about 1:1, 2:1, 4:1, 8:1, 10:1, 12:1, 14:1, 16:1, 18:1, and 20:1.

In some embodiments, the second compound is PMBN.

In some embodiments, the ratio of compound (I) to PMBN is selected from about 1:1, 2:1, 4:1, 8:1, 10:1, 12:1, 14:1, 16:1, 18:1, and 20:1.

In some embodiments, the amount of the second compound is below a therapeutic level for antibiotic activity of the second compound in treating the *Pseudomonas aeruginosa* infection.

In some embodiments in a pharmaceutical combination therapy for the treatment or prevention of a *Pseudomonas aeruginosa* infection, the pharmaceutical combination therapy further comprises ampicillin.

In some embodiments in a pharmaceutical combination therapy for the treatment or prevention of a *Pseudomonas aeruginosa* infection, the patient is immunocompromised.

In some embodiments in a pharmaceutical combination therapy for the treatment or prevention of a *Pseudomonas aeruginosa* infection, the patient has or is at risk for having cystic fibrosis (CF).

In some embodiments in a pharmaceutical combination therapy for the treatment or prevention of a *Pseudomonas aeruginosa* infection, the thymine bases are uracil bases.

In certain embodiments, the combination therapy includes the administration of one or more polymyxin nonapeptides. Removal of the hydrophobic tail of polymyxin B yields polymyxin nonapeptide (PMBN), which still binds to LPS, but no longer kills the bacterial cell. However, it still detectably increase the permeability of the bacterial cell wall to other antibiotics, indicating it still causes some degree of membrane disorganization. Similarly, enzymatic processing of polymyxin E to remove its hydrophobic tail yields polymyxin E nonapeptide. Accordingly, in some embodiments, the polymyxin nonapeptide is PMBN. In some embodiments, the polymyxin nonapeptide is a polymyxin E nonapeptide.

Thus, in some embodiments, the antimicrobial agent is a cationic, cyclic peptide antibiotic, as described herein. In certain of these and related embodiments, the bacterium comprises or expresses a ribosomal protein such as RpsJ, and the antisense oligonucleotide is targeted against RpsJ. In certain of these and related embodiments, the bacterium comprises or expresses a lipopolysaccharide biosynthesis gene such as LpxC, and the antisense oligonucleotide is targeted against LpxC. In some embodiments, the bacterium comprises or expresses a target gene selected from RpsJ, LpxC, FabG, AcpP, RpmB, WaaC, MraY, MurC, AccA, LpxA, LpxB, WaaG, WaaA, WaaF, MurB, MurE, AccB, FabZ, MurF, MurG, or AmpR, and the antisense oligonucleotide is targeted against a gene selected from RpsJ, LpxC, FabG, AcpP, RpmB, WaaC, MraY, MurC, AccA, LpxA, LpxB, WaaG, WaaA, WaaF, MurB, MurE, AccB, FabZ, MurF, MurG, or AmpR. In certain embodiments, the antisense oligonucleotides of the disclosure comprise a targeting sequence that is complimentary to a *Pseudomonas aeruginosa* mRNA that encodes RpsJ, LpxC, FabG, AcpP, RpmB, WaaC, MraY, MurC, AccA, LpxA, LpxB, WaaG, WaaA, WaaF, MurB, MurE, AccB, FabZ, MurF, MurG, or AmpR. In particular embodiments, the antimicrobial agent is polymyxin E (Colistin). In other embodiments, the antimicrobial agent is polymyxin B. In specific embodiments, the bacterium is *Pseudomonas aeruginosa*.

In some embodiments, the antimicrobial agent is a cationic, cyclic peptide antibiotic that has undergone enzymatic processing to create the nonapeptide, as described herein. In certain of these and related embodiments, the bacterium comprises or expresses a ribosomal protein such as RpsJ, and the antisense oligonucleotide is targeted against RpsJ. In certain of these and related embodiments, the bacterium comprises or expresses a lipopolysaccharide biosynthesis gene such as LpxC, and the antisense oligonucleotide is targeted against LpxC. In certain of these and related embodiments, the bacterium comprises or expresses a ribosomal protein such as RpmB, and the antisense oligonucleotide is targeted against RpmB. In some embodiments, the bacterium comprises or expresses a target gene selected from RpsJ, LpxC, FabG, AcpP, RpmB, WaaC, MraY, MurC, AccA, LpxA, LpxB, WaaG, WaaA, WaaF, MurB, MurE, AccB, FabZ, MurF, MurG, or AmpR, and the antisense oligonucleotide is targeted against a gene selected from RpsJ, LpxC, FabG, AcpP, RpmB, WaaC, MraY, MurC, AccA, LpxA, LpxB, WaaG, WaaA, WaaF, MurB, MurE, AccB, FabZ, MurF, MurG, or AmpR. In certain embodiments, the targeting sequence is complimentary to a *Pseudomonas aeruginosa* mRNA that encodes RpsJ, LpxC, FabG, AcpP, RpmB, WaaC, MraY, MurC, AccA, LpxA, LpxB, WaaG, WaaA, WaaF, MurB, MurE, AccB, FabZ, MurF, MurG, or AmpR. In particular embodiments, the antimicrobial agent is polymyxin B nonapeptide (PMBN). In some embodiments, the antimicrobial agent is polymyxin E nonapeptide. In specific embodiments, the bacterium is *Pseudomonas aeruginosa*.

In some embodiments, the antisense oligonucleotide increases the sensitivity of a given bacteria to the antimicrobial agent, relative to the antimicrobial agent alone. For example, in certain embodiments, the antisense oligonucleotide increases the sensitivity of the bacterium to the antimicrobial agent by increasing the bactericidal (cell-killing) and/or bacteriostatic (growth-slowing) activity of the antimicrobial agent against the bacterium being targeted, relative to the antimicrobial agent alone. In particular embodiments, the antisense increases the sensitivity by about or at least about 5, 10, 15, 20, 25, 30, 35, 40, 45, 50, 55, 60, 65, 70, 75, 80, 85, 90, 95, 100, 150, 200, 250, 300, 350, 400, 450, 500, 600, 700, 800, 900, or 1000% or more (including all integers and ranges in between), relative to the antimicrobial agent alone, or by about or at least about 2, 3, 4, 5, 6, 7, 8, 9, 10, 15, 20, 25, 30, 35, 40, 45, 50, 55, 60, 65, 70, 75, 80, 85, 90, 95, or 100-fold or more (including all integers and ranges in between), relative to the antimicrobial agent alone.

In some embodiments, the antisense oligonucleotide reduces the minimum inhibitory concentration (MIC) of an antimicrobial agent against the bacterium being targeted, relative to the antimicrobial agent alone. The "minimum inhibitory concentration" or "MIC" refers to the lowest concentration of an antimicrobial agent that will inhibit the visible growth of a microorganism after overnight (in vitro) incubation. Minimum inhibitory concentrations are important in diagnostic laboratories to confirm resistance of microorganisms to an antimicrobial agent and also to monitor the activity of new antimicrobial agents. The MIC is generally regarded as the most basic laboratory measurement of the activity of an antimicrobial agent against a bacterial organism. Thus, in certain embodiments, the oligonucleotide reduces the minimum inhibitory concentration (MIC) of an antimicrobial agent against the bacterium by at least about 5, 10, 15, 20, 25, 30, 35, 40, 45, 50, 55, 60, 65, 70, 75, 80, 85, 90, 95, 100, 150, 200, 250, 300, 350, 400, 450, 500, 600, 700, 800, 900, or 1000% or more (including all integers and ranges in between), relative to the antimicrobial agent alone. In certain embodiments, the oligonucleotide reduces the minimum inhibitory concentration (MIC) of an antimicrobial agent against the bacterium by about or at least about 2, 3, 4, 5, 6, 7, 8, 9, 10, 15, 20, 25, 30, 35, 40, 45, 50, 55, 60, 65, 70, 75, 80, 85, 90, 95, or 100-fold or more (including all integers and ranges in between), relative to the antimicrobial agent alone.

In some embodiments, the antisense oligonucleotide that increases the sensitivity or reduces the MIC is targeted against RpsJ, the bacterium is *Pseudomonas aeruginosa* that comprises or expresses RpsJ, and the antimicrobial agent is a cationic, cyclic peptide antibiotic such as polymyxin B or polymyxin E (Colistin) or is polymyxin B nonapeptide (PMBN) or polymyxin E nonapeptide (PMEN).

In particular embodiments, the antisense oligonucleotide that increases the sensitivity or reduces the MIC is targeted against LpxC, the bacterium is *Pseudomonas aeruginosa* that comprises or expresses LpxC, and the antimicrobial agent is a cationic, cyclic peptide antibiotic such as polymyxin B or polymyxin E (Colistin) or is polymyxin B nonapeptide (PMBN) or polymyxin E nonapeptide (PMEN).

In particular embodiments, the antisense oligonucleotide that increases the sensitivity or reduces the MIC is targeted against RpmB, the bacterium is *Pseudomonas aeruginosa* that comprises or expresses RpmB, and the antimicrobial agent is a cationic, cyclic peptide antibiotic such as polymyxin B or polymyxin E (Colistin) or is polymyxin B nonapeptide (PMBN) or polymyxin E nonapeptide (PMEN).

In some embodiments, the antisense oligonucleotide that increases the sensitivity or reduces the MIC is targeted against a gene selected from RpsJ, LpxC, FabG, AcpP, RpmB, WaaC, MraY, MurC, AccA, LpxA, LpxB, WaaG, WaaA, WaaF, MurB, MurE, AccB, FabZ, MurF, MurG, or AmpR, the bacterium is *Pseudomonas aeruginosa* that comprises or expresses a gene selected from RpsJ, LpxC, FabG, AcpP, RpmB, WaaC, MraY, MurC, AccA, LpxA, LpxB, WaaG, WaaA, WaaF, MurB, MurE, AccB, FabZ, MurF, MurG, or AmpR, and the antimicrobial agent is a cationic, cyclic peptide antibiotic such as polymyxin B or polymyxin E (Colistin) or is polymyxin B nonapeptide (PMBN) or polymyxin E nonapeptide (PMEN).

Additional antimicrobial agents can also be employed as part of any given combination therapy. Examples of antimicrobial agents (e.g., antibiotics) that can be administered in combination with an antisense oligonucleotide include beta-lactam antibiotics such as carbapenems, penicillin and penicillin derivatives (or penams), cephalosporins (e.g., Cefacetrile (cephacetrile), Cefadroxil (cefadroxyl; Duricef), Cephalexin (cefalexin; Keflex), Cefaloglycin (cephaloglycin), Cefalonium (cephalonium), Cefaloridine (cephaloradine), Cefalotin (cephalothin; Keflin), Cefapirin (cephapirin; Cefadryl), Cefatrizine, Cefazaflur, Cefazedone, Cefazolin (cephazolin; Ancef, Kefzol), Cefradine (cephradine; Velosef), Cefroxadine, Ceftezole, Cefaclor (Ceclor, Distaclor, Keflor, Raniclor), Cefonicid (Monocid), Cefprozil (cefproxil; Cefzil), Cefuroxime (Zefu, Zinnat, Zinacef, Ceftin, Biofuroksym, Xorimax), Cefuzonam, Cefmetazole, Cefotetan, Cefoxitin, loracarbef (Lorabid); Cephamycins: cefbuperazone, cefmetazole (Zefazone), cefrninox, cefotetan (Cefotan), cefoxitin (Mefoxin), Cefotiam (Pansporin), Cefcapene, Cefdaloxime, Cefdinir (Sefdin, Zinir, Omnicef, Kefnir), Cefditoren, Cefetamet, Cefixime (Fixx, Zifi, Suprax), Cefmenoxime, Cefodizime, Cefotaxime (Claforan), Cefovecin (Convenia), Cefpimizole, Cefpodoxime (Vantin, PECEF), Cefteram, Ceftibuten (Cedax), Ceftiofur, Ceftiolene, Ceftizoxime (Cefizox), Ceftriaxone (Rocephin), Cefoperazone (Cefobid), Ceftazidime (Meezat, Fortum, Fortaz), latamoxef (moxalactam), Cefclidine, cefepime (Maxipime), cefluprenam, cefoselis, Cefozopran, Cefpirome (Cefrom), Cefquinome, flomoxef, Ceftobiprole, Ceftaroline, Cefaloram, Cefaparole, Cefcanel, Cefedrolor, Cefempidone, Cefetrizole, Cefivitril, Cefmatilen, Cefmepidium, Cefoxazole, Cefrotil, Cefsumide, Ceftioxide, Cefuracetime), and monobactams (e.g., aztreonam, tigemonam, nocardin A, tabtoxin); aminoglycosides such as tobramycin, gentamicin, kanamycin a, amikacin, dibekacin, sisomicin, netilmicin, neomycin B, neomycin C, neomycin E (paromomycin), and streptomycin; tetracyclines such as tetracycline, chlortetracycline, oxytetracycline, demeclocycline, lymecycline, meclocycline, methacycline, minocycline, rolitetracycline, and doxycyline; sulfonamides such as sulfacetamide, sulfadiazine, sulfadimidine, sulfafurazole, sulfisomidine, sulfadoxine, sulfamethoxazole, sulfamoxole, sulfadimethoxine, sulfamethoxypyridazine, sulfametoxydiazine, sulfadoxine, and sulfametopyrazine; quinolones such as cinoxacin, nalidixic acid, oxolinic acid (Uroxin), piromidic acid (Panacid), pipemidic acid (Dolcol) rosoxacin (Eradacil), ciprofloxacin (Alcipro, Ciprobay, Cipro, Ciproxin, ultracipro), enoxacin (Enroxil, Penetrex), fleroxacin (Megalone, Roquinol), lomefloxacin (Maxaquin), nadifloxacin (Acuatim, Nadoxin, Nadixa), norfloxacin (Lexinor, Noroxin, Quinabic, Janacin), ofloxacin (Floxin, Oxaldin, Tarivid), pefloxacin (Peflacine), rufloxacin (Uroflox), balofloxacin (Baloxin), grepafloxacin (Raxar), levofloxacin (Cravit, Levaquin, Tavanic), pazufloxacin (Pasil, Pazucross), sparfloxacin (Zagam), temafloxacin (Omniflox), tosufloxacin (Ozex, Tosacin), clinafloxacin, gatifloxacin (Zigat, Tequin) (Zymar-opth.), gemifloxacin (Factive), moxifloxacin (Acflox Woodward, Avelox, Vigamox, sitafloxacin (Gracevit), trovafloxacin (Trovan), prulifloxacin (Quisnon);

oxazolidinones such as eperezolid, linezolid, posizolid, radezolid, ranbezolid, sutezolid, and tedizolid; polymyxins such as polysporin, neosporin, polymyxin B, polymyxin E (colistin); rifamycins such as rifampicin or rifampin, rifabutin, rifapentine, and rifaximin; lipiarmycins such as fidaxomicin; macrolides such as azithromycin, clarithromycin, dirithromycin, erythromycin, roxithromycin, telithromycin, carbomycin A, josamycin, kitasamycin, midecamycin/midecamycin acetate, oleandomycin, solithromycin, spiramycin, and troleandomycin; lincosamides such as lincomycin, clindamycin, and pirlimycin; cyclic lipopeptides such as daptomycin; glycopeptides such as vancomycin and teichoplanin; glycylcyclines such as tigecycline. Thus, any one or more of the foregoing antibiotics can be combined with any of the antisense oligonucleotides described herein, for the treatment of any of the bacteria described herein.

Treatment Monitoring Methods

The efficacy of a given therapeutic regimen involving the methods described herein may be monitored, for example, by general indicators of bacterial infection, such as complete blood count (CBC), nucleic acid detection methods, immunodiagnostic tests, or bacterial culture.

In some aspects, identification and monitoring of bacterial infection involves one or more of (1) nucleic acid detection methods, (2) serological detection methods, i.e., conventional immunoassay, (3) culture methods, and (4) biochemical methods. Such methods may be qualitative or quantitative.

Nucleic acid probes may be designed based on publicly available bacterial nucleic acid sequences, and used to detect target genes or metabolites (i.e., toxins) indicative of bacterial infection, which may be specific to a particular bacterial type, e.g., a particular species or strain, or common to more than one species or type of bacteria (i.e., Gram positive or Gram negative bacteria). Nucleic amplification tests (e.g., PCR) may also be used in such detection methods.

Serological identification may be accomplished using a bacterial sample or culture isolated from a biological specimen, e.g., stool, urine, cerebrospinal fluid, blood, etc. Immunoassay for the detection of bacteria is generally carried out by methods routinely employed by those of skill in the art, e.g., ELISA or Western blot. In addition, monoclonal antibodies specific to particular bacterial strains or species are often commercially available.

Culture methods may be used to isolate and identify particular types of bacteria, by employing techniques including, but not limited to, aerobic versus anaerobic culture, growth and morphology under various culture conditions. Exemplary biochemical tests include Gram stain (Gram, 1884; Gram positive bacteria stain dark blue, and Gram negative stain red), enzymatic analyses, and phage typing.

It will be understood that the exact nature of such diagnostic, and quantitative tests as well as other physiological factors indicative of bacterial infection will vary dependent upon the bacterial target, the condition being treated and whether the treatment is prophylactic or therapeutic.

In cases where the subject has been diagnosed as having a particular type of bacterial infection, the status of the bacterial infection is also monitored using diagnostic techniques typically used by those of skill in the art to monitor the particular type of bacterial infection under treatment.

The PMO or PPMO treatment regimen may be adjusted (dose, frequency, route, etc.), as indicated, based on the results of immunoassays, other biochemical tests and physiological examination of the subject under treatment.

From the foregoing, it will be appreciated how various objects and features of the disclosure are met. The method provides an improvement in therapy against bacterial infection, for example, multi-drug resistant (MDR) bacteria and/or biofilm-forming bacteria, using antisense oligonucleotides against bacterial genes involved in biochemical pathways and/or cellular processes to achieve enhanced cell uptake and anti-bacterial action. As a result, drug therapy is more effective and less expensive, both in terms of cost and amount of compound required.

One exemplary of the disclosure is that compounds effective against virtually any pathogenic bacterial can be readily designed and tested, e.g., for rapid response against new drug-resistant strains.

The following examples are intended to illustrate but not to limit the disclosure. Each of the patent and non-patent references referred to herein is incorporated by reference in its entirety.

EXAMPLES

Materials and Methods

*P. aeruginosa* PPMO-MIC Protocol

Day −1:

One colony (or more) of *P. aeruginosa* is picked from a fresh plate into 2 ml of MH and grown overnight.

Day 0:

The overnight culture is plated to determine CFU/ml of starting inoculum. From the overnight culture 4 µl is taken into 10 ml of fresh medium and mixed well to obtain a bacterial working suspension. From the 10 ml, 50 µl is taken into 450 µl of saline. Serial dilutions of $10^{-2}$, $10^{-3}$ and $10^{-4}$ are plated on BA. If Polymyxin B Nonapeptide (PMBN) is to be added, 4 µl/ml of PMBN is added from a stock of 1 mg/ml (in water) to the bacterial suspension for a 4 µg/ml final PMBN concentration.

For every PPMO to be tested, the following is done: 6.8 µl of a 1 mM PPMO stock is added to 413.2 µl of bacterial working suspension and vortexed. 200 µl is placed in the first row (A) of a 96-well plate in duplicate. 100 µl of bacterial working suspension is added to rows B thru F. Row A is mixed well by pipetting 10 times. Then 100 µl from each well of row A is added to the 100 µl of bacterial working suspension in each well of row B and mixed well 10 times. Serial dilutions are continued in the same manner through to row F. Finally, 100 µl in the last row is removed and discarded. Thus row A has PPMO at 16 µM, row B has PPMO at 8 µM, row C has PPMO at 4 µM, row D has PPMO at 2 µM, row E has PPMO at 1 µM and row F has PPMO at 0.5 µM. Row H can be used for controls. Controls (in duplicate) can include media alone, bacterial suspension alone, any additional treatment with media or with bacterial suspension. The 96-well plate is covered with a breathable membrane and incubated for 18 hrs at 37° C. and 225 rpm.

Day +1:

The plate is read in a plate reader to measure $OD_{600}$.

*Pseudomonas aeruginosa* Biofilm Prevention in MBEC Plate Protocol

Day 0:

A fresh plate is streaked and grown overnight in an incubator.

Day 1:

1. 10 mL of MH is inoculated with a single colony and incubated at 37° C. and ~250 rpm for about 5 hours.
2. The sample is centrifuged for 10 minutes at ~4000 rpm at 4° C., the supernatant is decanted and the pellet resuspended in 10 mL of 150 mM NaCl or PBS. This step is repeated to wash the pellet 3 times.

3. The sample is resuspended in 10 mL 150 mM NaCl or PBS.
4. The $OD_{600}$ of the sample is taken and cfu/mL is calculated. ($OD_{600}$ usually between 0.65-0.80).
5. A Bacterial Working Solution (BWS) is made by inoculating 10 mL of MH to $5\times10^5$ cfu/mL final concentration.
6. 2 µL/mL of 1 mg/mL stock PMBN is added to the BWS and vortexed 3 times.
7. 1 mL of BWS is pipetted into each separate Eppendorf tube for each condition that is tested.
8. An appropriate amount of PPMO is added to each Eppendorf tube and vortexed 3 times.
9. Outside wells are filled with fresh MH, NaCl, or PBS to keep the outer pegs from drying out.
10. One column of the MBEC plate is filled with 150 µL per well from each Eppendorf tube (one condition per column).
11. Pegs are placed into the MBEC plate and the edges covered with a breathable membrane.
12. The MBEC plate is incubated for 18-20 hours at 37° C. and 110 rpm.

Day 2:
1. MBEC plate processing:
   a. Rinse: Membrane strips are removed and the pegs are carefully lowered into a 96-well round bottom plate with 150 µL of 150 mM NaCl in each well. The pegs are allowed to sit in the NaCl solution for 1 min.
   b. Fix: The pegs are moved to another 96-well round bottom plate with 100% methanol (150 µL per well). Pegs are allowed to sit in methanol for 15 min.
   c. Dry: The pegs are removed from the methanol and air dried for at least 3 hours in a fume hood. The pegs can also be left to dry overnight for this step.
   d. Stain: The pegs are moved to another round bottom plate that has 150 µL per well of crystal violet (CV) solution. The plate is rocked on a plate rocker on the lowest setting for 20 min.
      i. Crystal violet (CV) solution recipe: 0.07 grams of CV powder are mixed into 100 mL of pure water (for a 0.07% concentration) and mixed overnight. 25 mL of this 0.07% CV solution is mixed into 500 mL of Medium 199. 12.5 mL of 1M HEPES solution is added to the mixture. The final $OD_{570}$ of the 10× dilution of solution should be approximately 0.500 absorbance. The solution is shaken well and stored at 4° C. when not in use.
   e. Dissolve: The pegs are moved to another 96-well plate with 150 µL of acetic acid in each well, and the plate is rocked vigorously for 10 min.
2. OD reading: The $OD_{570}$ for the 96-well plate from step 1e is determined.

Optional Step: In order to assess the growth of the bacteria, 100 µL is pipetted from the overnight MBEC plate into a new 96-well plate and the $OD_{600}$ determined.

*Pseudomonas aeruginosa* Biofilm Reduction in MBEC Plate Protocol

Day 1:
1. 10 mL of MH is inoculated with a single colony and incubated at 37° C. and ~250 rpm for about 5 hours.
2. The sample is centrifuged for 10 minutes at ~4000 rpm at 4° C., the supernatant decanted and the pellet resuspended in 10 mL of 150 mM NaCl or PBS. This step is repeated to wash the pellet 3 times.
3. The sample is resuspended in 10 mL 150 mM NaCl or PBS.
4. The $OD_{600}$ of the sample is taken and cfu/mL is calculated. ($OD_{600}$ usually between 0.65-0.80).
5. A Bacterial Working Solution (BWS) is made by inoculating 10 mL of MH to $5\times10^5$ cfu/mL final concentration.
6. 150 µL of BWS is placed into each well of an MBEC plate with no PPMO and covered.
7. The plate is incubated for 24 hours at 37° C. and 110 rpm.
8. A solution of approximately 15 mL of fresh media is made.
9. 2 µL/mL of 1 mg/mL stock PMBN is added to the fresh media and vortexed 3 times.
10. 1 mL of fresh media is pipetted into each separate Eppendorf tube for each condition that is tested.
11. An appropriate amount of PPMO is added to each Eppendorf tube and vortexed 3 times.
12. Three wells of a fresh 96-well plate are filled with 150 µL per well from each Eppendorf tube (one condition per three wells).
13. Pegs are placed into a fresh 96-well plate and the edges covered with a breathable membrane.
14. The plate is incubated for 8 hours at 37° C. and 110 rpm.
15. Steps 8-14 are repeated two more times (3× total) until 48 hours total. The plate is then removed and processed.

Day 2:
1. MBEC plate processing:
   a. Rinse: Membrane strips are removed and the pegs are carefully lowered into a 96-well round bottom plate with 150 µL of 150 mM NaCl in each well. The pegs are allowed to sit in the NaCl solution for 1 min.
   b. Fix: The pegs are moved to another 96-well round bottom plate with 100% methanol (150 µl per well). Pegs are allowed to sit in methanol for 15 min.
   c. Dry: The pegs are removed from the methanol and air dried for at least 3 hours in a fume hood. The pegs can also be left to dry overnight for this step.
   d. Stain: The pegs are moved to another round bottom plate that has 150 µL per well of crystal violet (CV) solution. The plate is rocked on a plate rocker on the lowest setting for 20 min.
      i. Crystal violet solution recipe: 0.07 grams of CV powder are mixed into 100 mL of pure water (for a 0.07% concentration) and mixed overnight. 25 mL of this 0.07% CV solution is mixed into 500 mL of Medium 199. 12.5 mL of 1M HEPES solution is added to the mixture. The final $OD_{570}$ of the 10× dilution of solution should be approximately 0.500 absorbance. The solution is shaken well and stored at 4° C. when not in use.
   e. Dissolve: The pegs are moved to another 96-well plate with 150 µL of acetic acid in each well, and the plate is rocked vigorously for 10 min.
2. OD reading: The $OD_{570}$ for the 96-well plate from step 1e is determined.

Optional Step: In order to assess the growth of the bacteria, 100 µL is pipetted from the overnight MBEC plate into a new 96-well plate and the $OD_{600}$ determined.

Example 1

Inhibition of *Pseudomonas* with PPMOs Alone

Cell-penetrating peptide-conjugated phosphorodiamidate morpholino oligonucleotides (PPMOs) were designed, synthesized and tested against essential genes representing a variety of biochemical pathways and cellular processes. These included: murein biosynthesis, cell division, global gene regulatory mechanisms, fatty acid biosynthesis, ribosomal proteins, DNA replication, transcription, translation initiation, lipopolysaccharide biosynthesis, nucleic acid biosynthesis, and intermediary metabolism.

Each PPMO (Tables 3 and 4) was first tested by measuring the minimal inhibitory concentration (MIC) according to the method used in hospital clinical labs (CLSI microdilution assay). The MIC of each PPMO was tested against a panel of P. aeruginosa strains. The composition of the panel was mostly clinical isolates and included multidrug-resistant isolates.

Pseudomonas Essential Gene Screen

A variety of Pseudomonas isolates were tested, including clinical isolates obtained from various body sites with varying levels of antibiotic resistance. The majority of PPMOs tested had MICs>16 µM when tested alone (FIG. 1).

Example 2

PPMOs are Synergistic with Polymyxin E (Colistin) in P. aeruginosa

Polymyxin is a naturally occurring cationic cyclic decapeptide isolated from Bacillus polymyxa. Polymyxin is highly bactericidal in Gram-negative bacteria. Due to its high-affinity binding to lipid A, polymyxin is one of the most efficient cell-permeabilizing compounds. However, therapeutic applications of polymyxin are very limited because of its relatively high toxicity.

Figure 2:
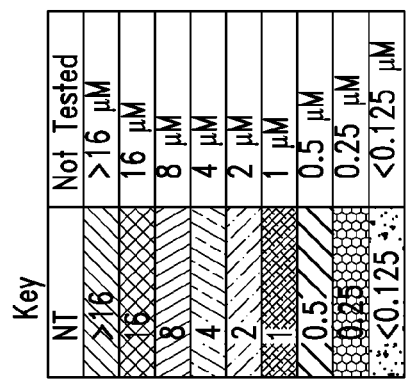
FIG. 2 shows a heat map of the minimal inhibitory concentration (MIC) values for PPMOs of Tables 3 and 4 combined with sub-inhibitory concentrations of Colistin (polymyxin E) tested against a panel of *P. aeruginosa* clinical isolates with varying levels of antibiotic resistance. MICs are indicated by color and numerical value as in FIG. 1. All MICs were performed in the presence of 1 µg/mL of Colistin unless otherwise noted (*Strains with an asterisk were tested with 0.5 µg/mL of Colistin). While there was no growth inhibition of *Pseudomonas* by Colistin alone, PPMOs demonstrated enhanced activity across a wide range of gene targets. The most potent PPMOs had $IC_{50}$ concentrations of 0.5 µM.

It was discovered that PPMOs were synergistic with an older traditional antibiotic, polymyxin E (Colistin). Colistin alone at either 1 or 0.5 µg/ml (depending on the strain) did not inhibit growth of any Pseudomonas strain tested, meaning Colistin was sub-therapeutic or at a sub-bactericidal level for Pseudomonas strains. However, as seen in the heat map in FIG. 2, when the same PPMOs (Tables 3 and 4) were combined with sub-inhibitory concentrations of Colistin, there was a dramatic synergistic effect. There were 18 PPMOs where 75% of the strains tested had MICs of 8 µM or less. The PPMOs that showed activity were across a number of essential gene targets including: LpxC, RpsJ, AccA, WaaG, FabG, MraY, AcpP and LpxB. These PPMOs target a number of essential bacterial pathways including lipopolysaccharide (LPS), peptidoglycan and fatty acid biosynthesis as well as ribosomal targets.

Example 3

Sub-Inhibitory Concentrations of Polymyxin B Nonapeptide (PMBN) Enhance PPMO Activity in MHII Media and MOPS Minimal Media Without being bound by any particular theory, given the fact that a number of PPMOs were effective when combined with Colistin, it was hypothesized that the main issues in increasing potency were related to cellular uptake of the PPMO. Studies were undertaken to determine alternative ways to get enhanced uptake of PPMOs by Pseudomonas.

Figure 3:
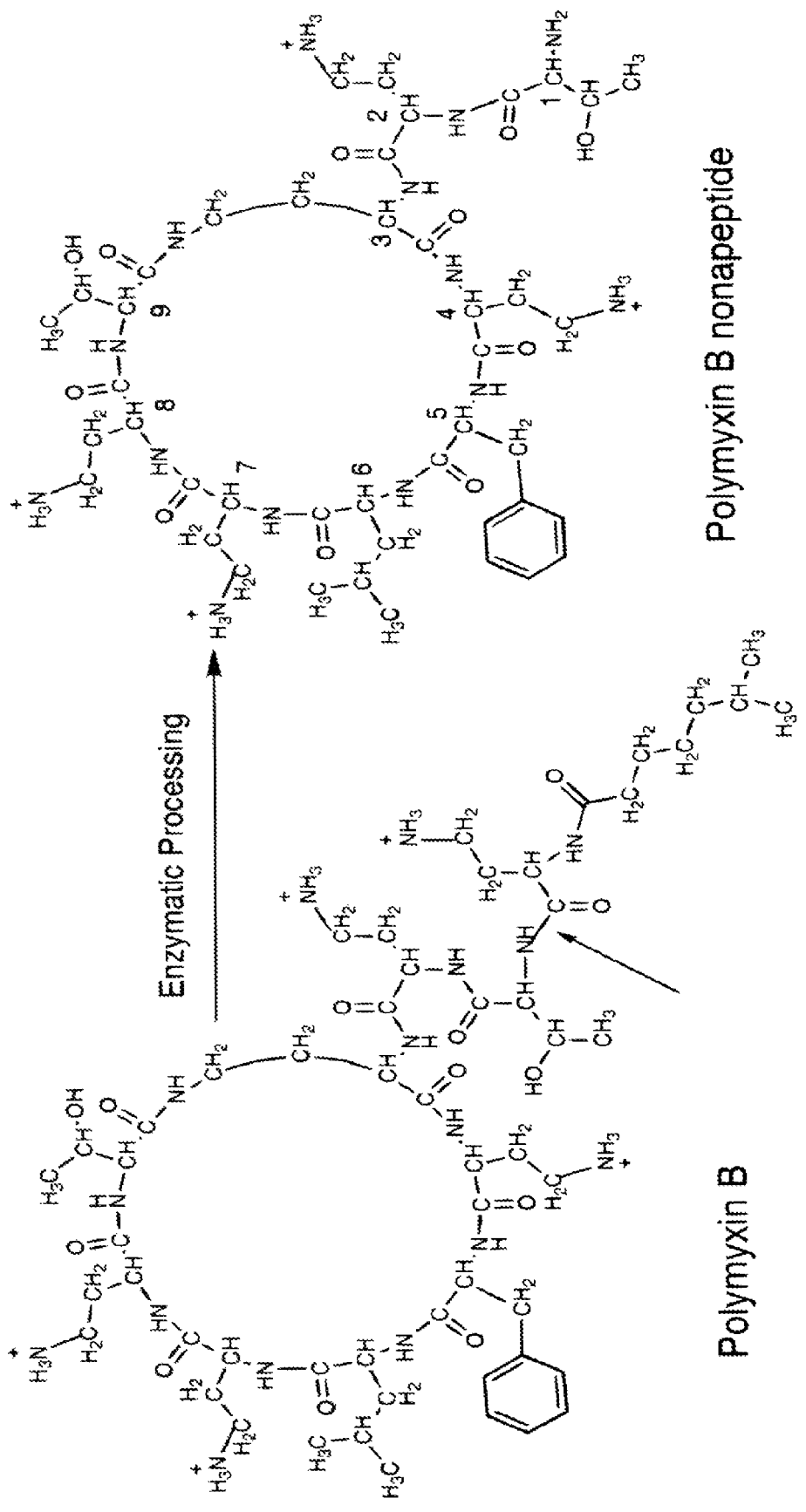
FIG. 3 shows generation of Polymyxin B nonapeptide (PMBN) from Polymyxin B (PMB) by enzymatic processing.

A chemical modification in a related polymyxin antibiotic, Polymyxin B (PMB), results in the cationic cyclic peptide Polymyxin B Nonapeptide (PMBN) (FIG. 3). This cyclic peptide has been shown, by itself, to have poor antibacterial activity. However, just like the unmodified PMB, the peptide still binds to LPS on the surface of Gram-negative bacteria, but unlike PMB, PMBN has very low toxicity on human cells. Given the synergistic results of PPMOs and Colistin, the PPMOs (Tables 3 and 4) were screened in the presence of different concentrations of PMBN.

Figure 4A:
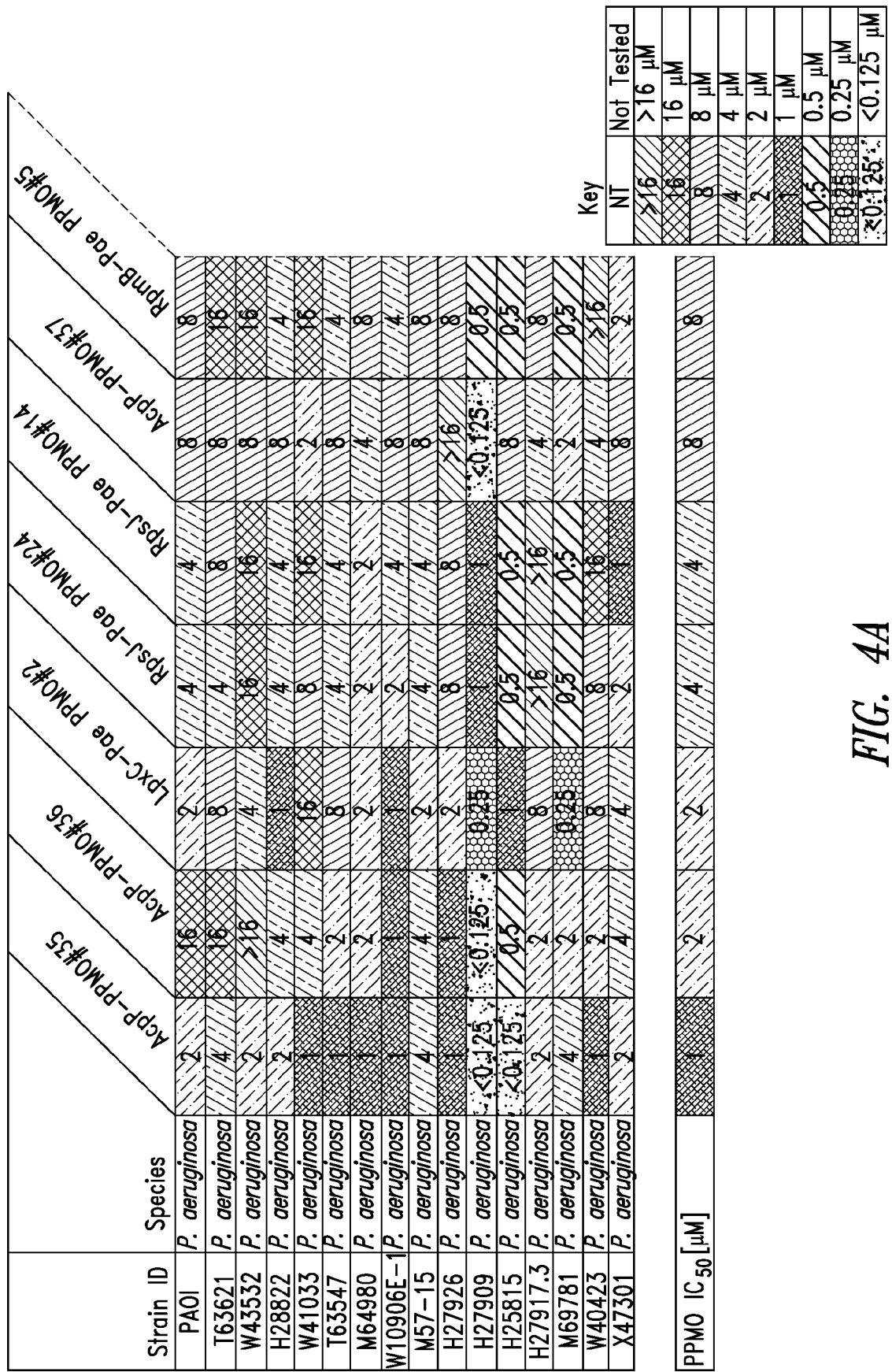
FIGS. 4A-4C show heat maps of PPMO MICs with sub-inhibitory concentrations of PMBN. PPMOs showed increased activity in MHII media in the presence of PMBN as compared to PPMOs alone. PPMOs also showed activity in MOPS MM without PMBN.
Figure 4A:
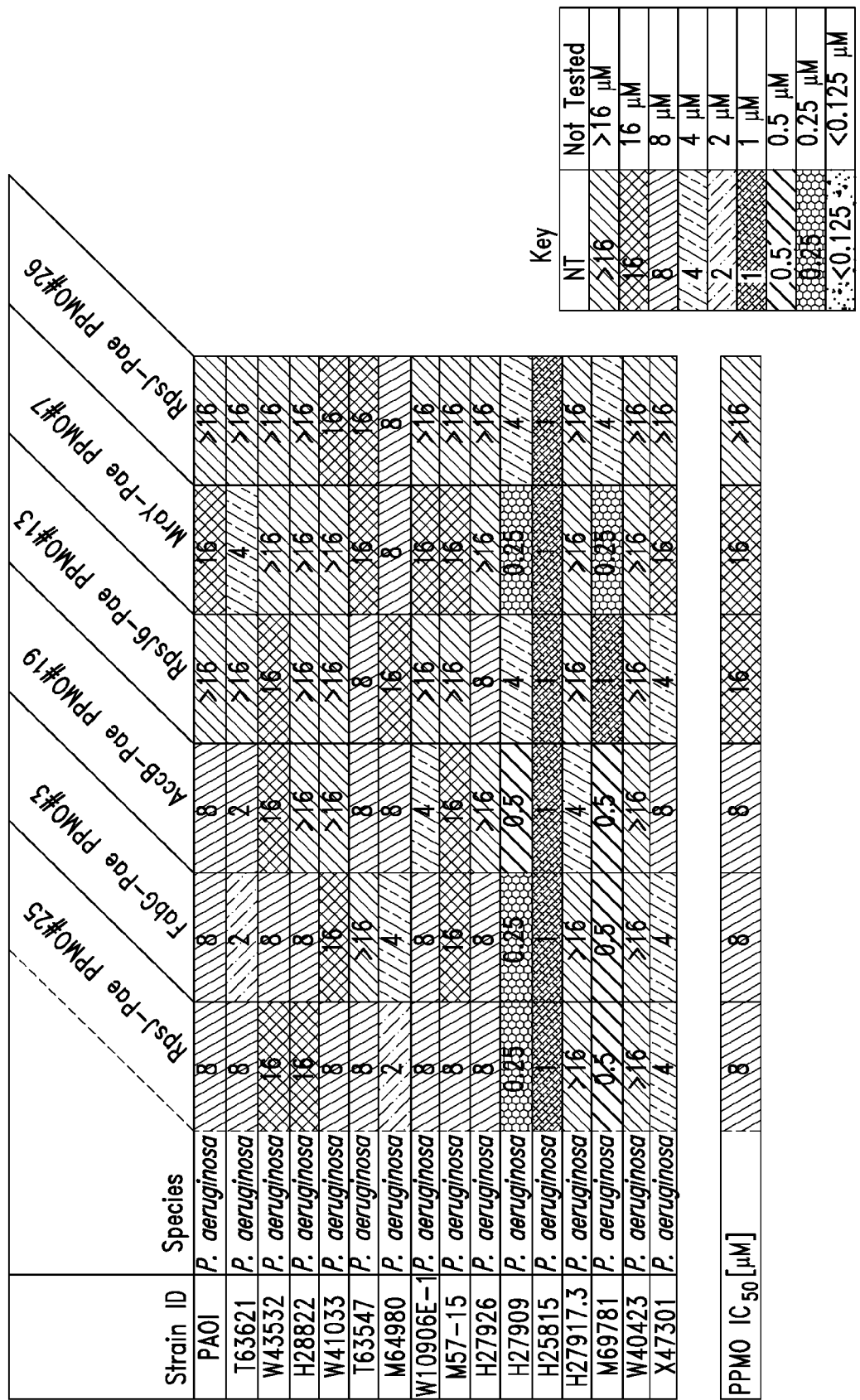
Figure 4B:
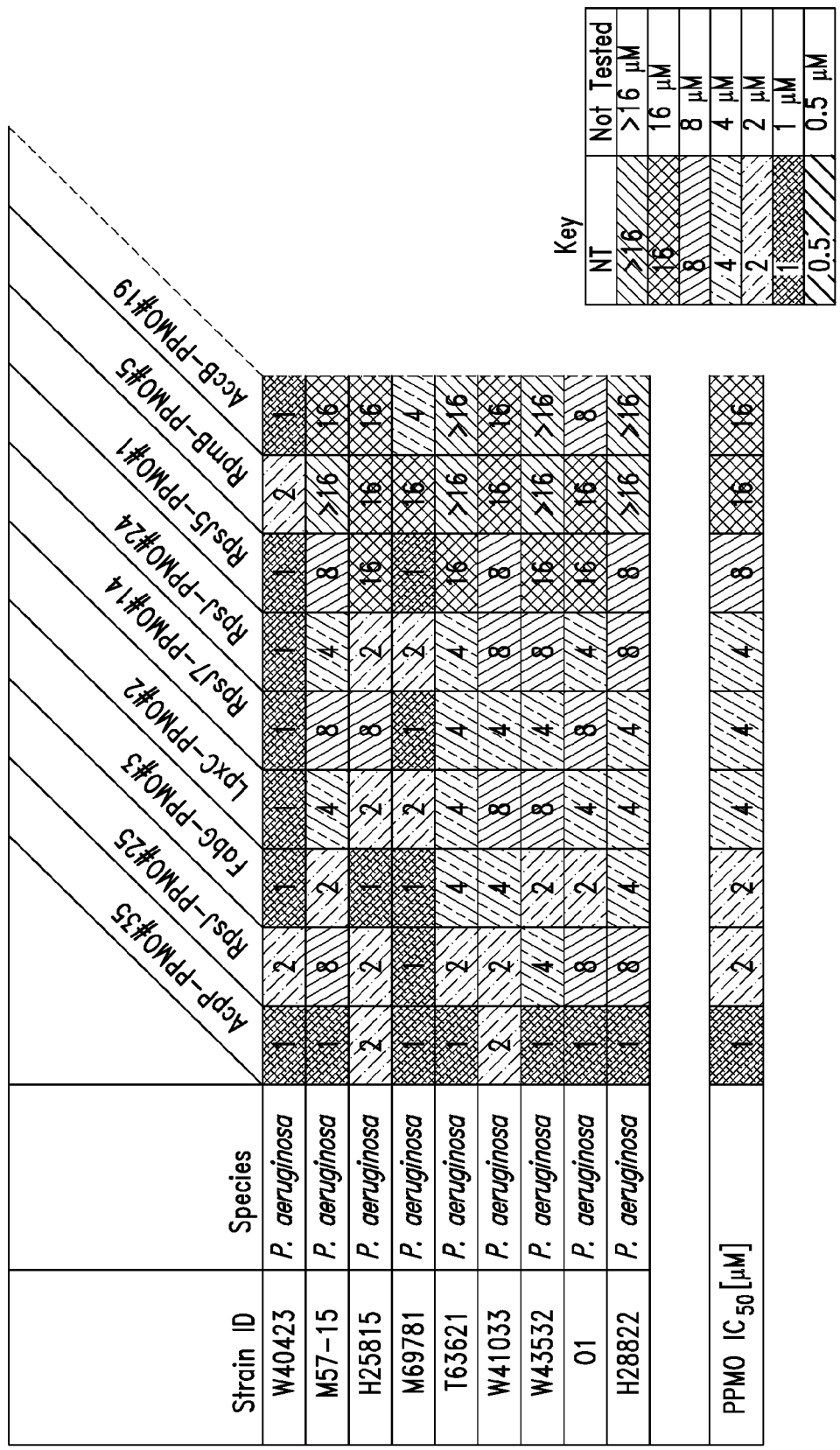
Figure 4B:
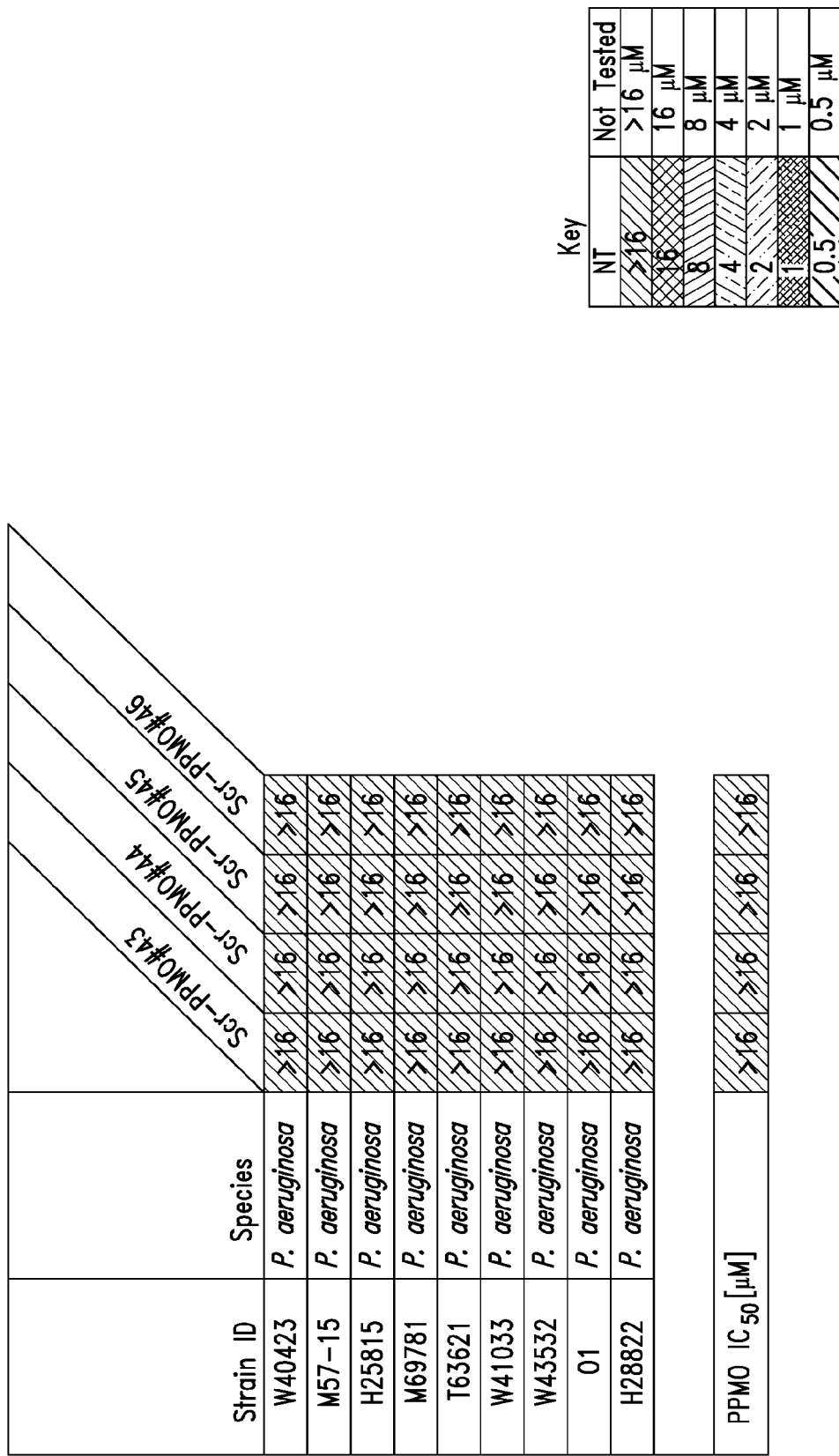
Figure 4C:
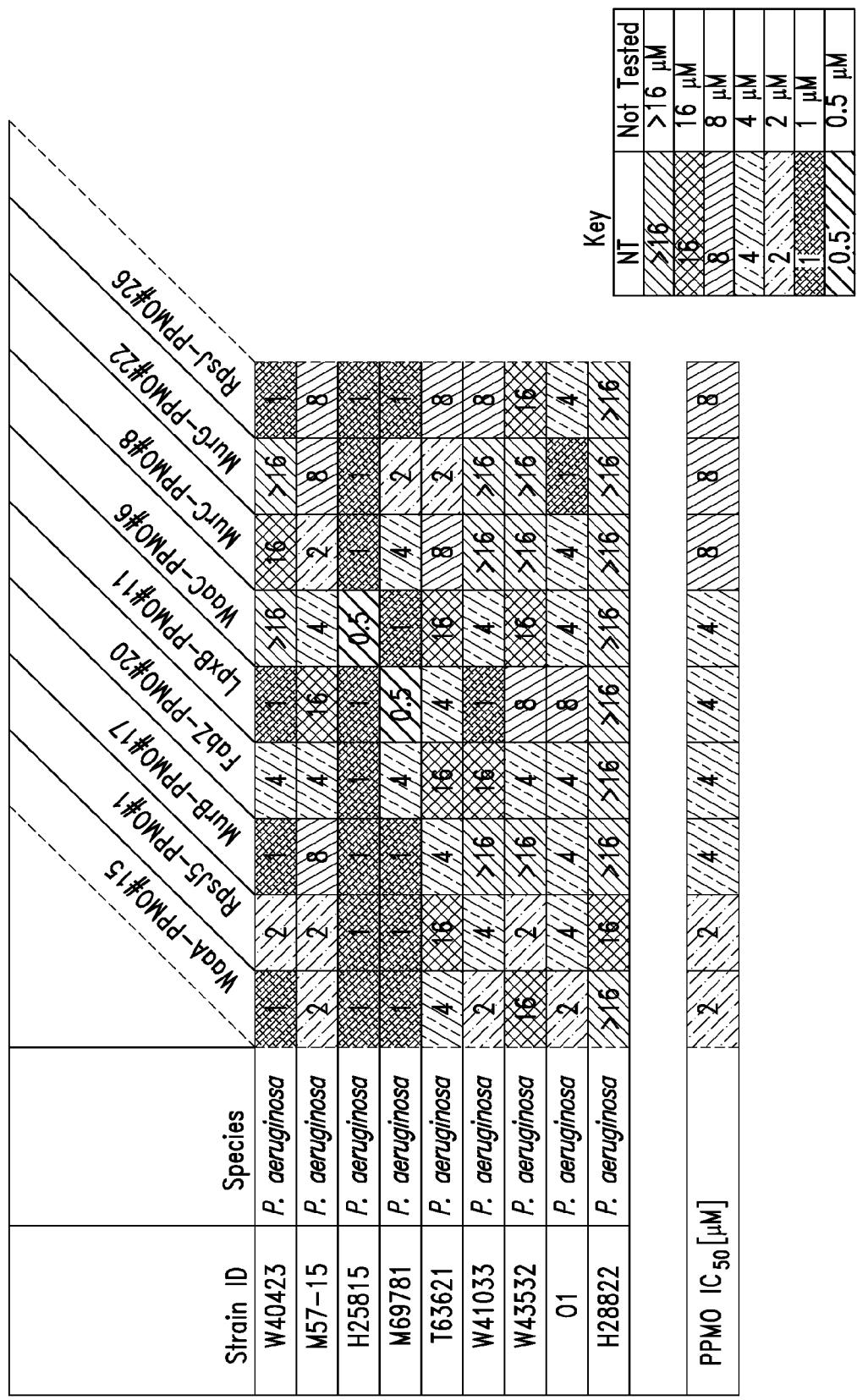

As shown in FIGS. 4A-4C, PPMOs showed increased activity in MHII media in the presence of PMBN as compared to PPMOs alone. PPMOs also showed activity in MOPS MM without PMBN. FIG. 4A: MICs were performed in MH with 2 µg/mL PMBN. FIG. 4B: MICs were performed in MOPS MM without PMBN. FIG. 4C: MICs were performed in MOPS MM with 0.25 µg/mL of PMBN.

Example 4

PPMO+PMBN Cause Time and Dose Dependent Killing of Pseudomonas

Figures 5A, 5B:
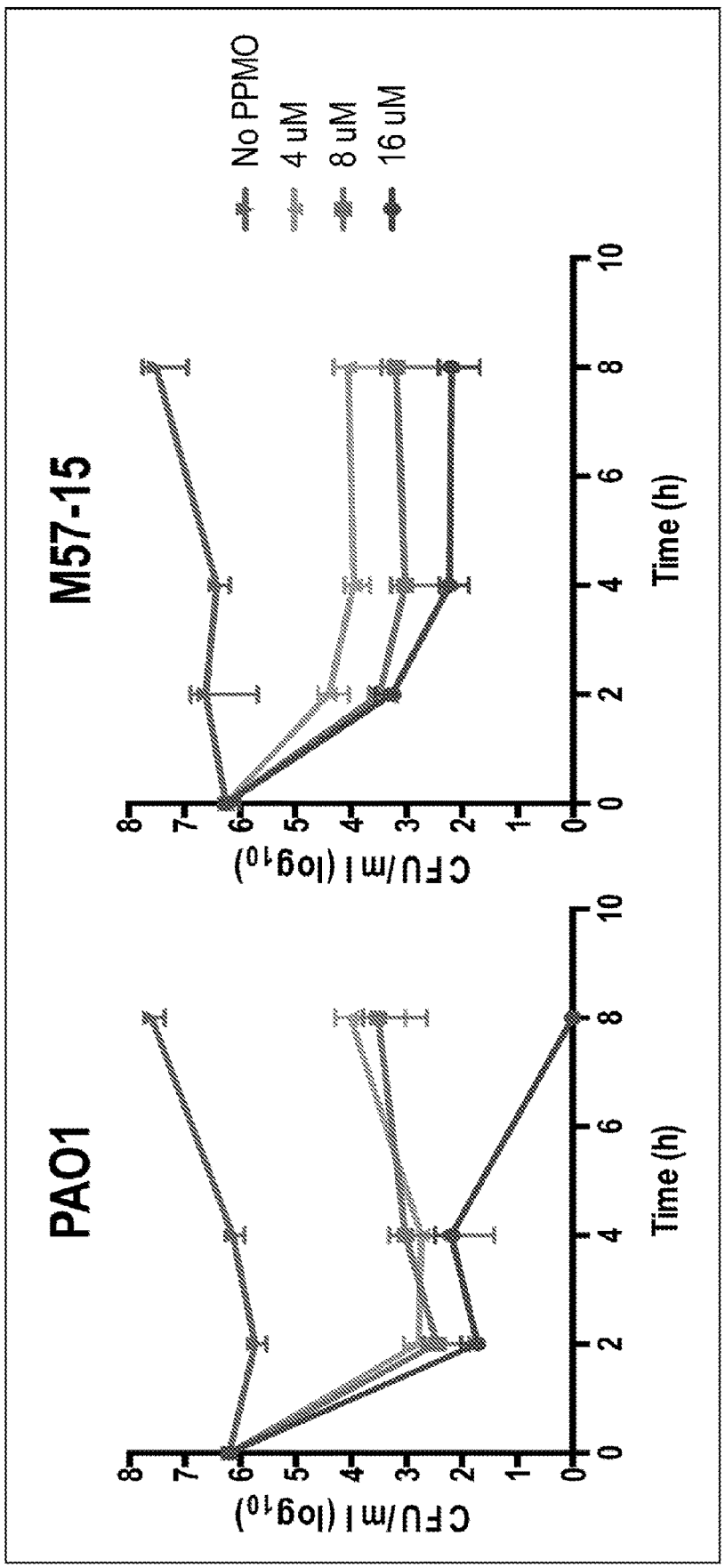
FIG. 5 shows the colony forming units (CFU)/ml (log 10) over time in two different *P. aeruginosa* strains (PAO1 and M57-15) with various concentrations of RpsJ PPMO incubated with a fixed concentration of PMBN (4 µg/ml). PPMOs inhibit growth of *P. aeruginosa* in a time and concentration-dependent fashion.

PPMOs displayed both time and concentration-dependent killing as shown in FIG. 5. By 8 hours of incubation, RpsJ PPMO with 4 µg/ml PMBN had an approximately 3-log decrease in CFU/ml at 4 µM in two different P. aeruginosa strains (PAO1 and M57-15). At 16 µM of PPMO, the CFU/ml was at or below the limit of detection. In addition, MIC values of 8 µM or less in P. aeruginosa strains that are multidrug resistant have been achieved. For example, strain T63547 was isolated from the sputum of a CF patient and was resistant to extended-spectrum penicillins, cephalosporins, quinolones and carbapenems. The RpsJ PPMOs and the RpmB PPMO had MIC values of 4 µM. PPMOs also retained activity in mucoid strains of P. aeruginosa (such as strain H27925; CF sputum sample). This is a critically important finding, as mucoid Pseudomonas poses significant treatment challenges.

Example 5

PPMO Treatment Prevents Formation of P. aeruginosa Biofilm

Figure 6A:
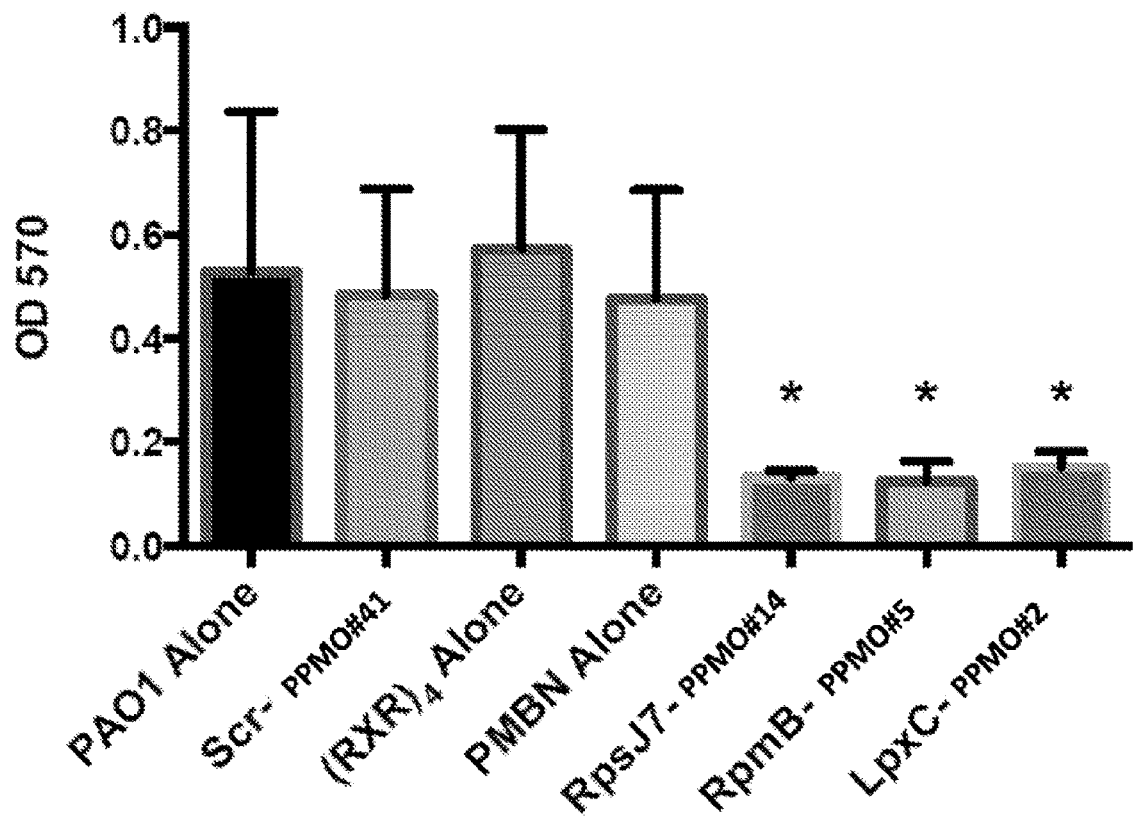
FIG. 6A: Crystal violet analysis of 20 hour biofilms showed statistically significant prevention of biofilm with RpsJ (PPMO #14), RpmB (PPMO #5) and LpxC (PPMO #2) PPMOs at 5 µM concentrations (one-way ANOVA p<0.0001. *Statistically significant difference from No PPMO, Scr PPMO #41, Peptide, and Nonapeptide when analyzed by Tukey's Multiple comparisons test).
Figure 6B:
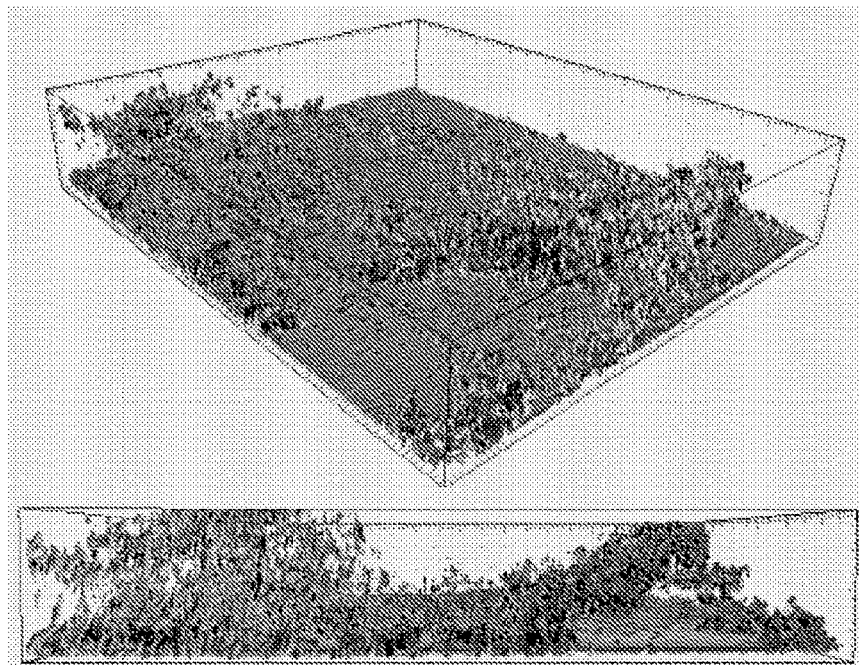
FIGS. 6B-6D: Spinning Disk confocal microscopy images of 20 hour biofilm treated with (FIG. 6B) No PPMO, (FIG. 6C) 5 µM Scr PPMO #41, (FIG. 6D) 5 µM RpsJ PPMO #14. PAO1 GFP is shown in green and biofilm is shown in red. The biofilm is stained with 200 µg/mL of Concanavalin A, Alexafluor 647 conjugate.
Figure 6C:
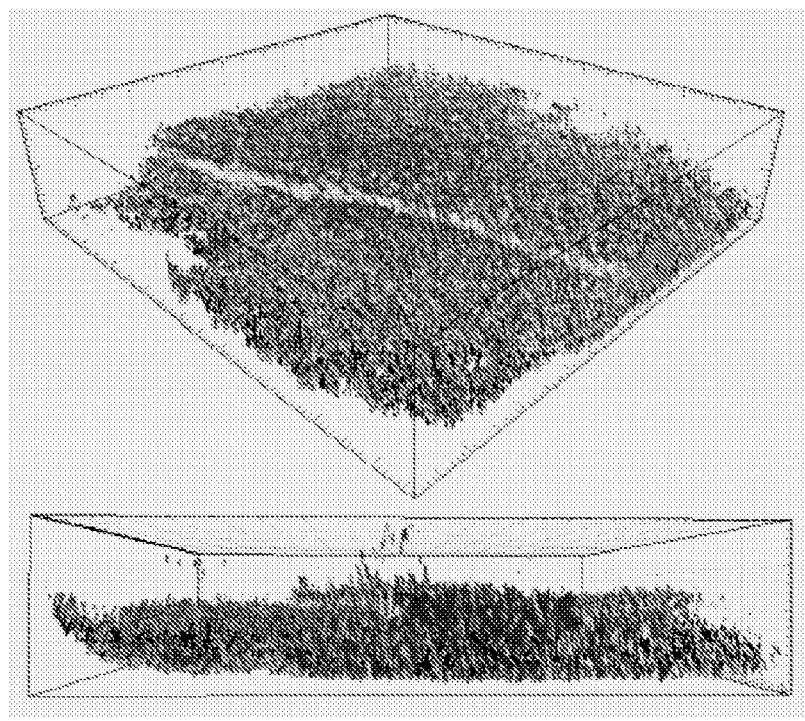
Figure 6D:
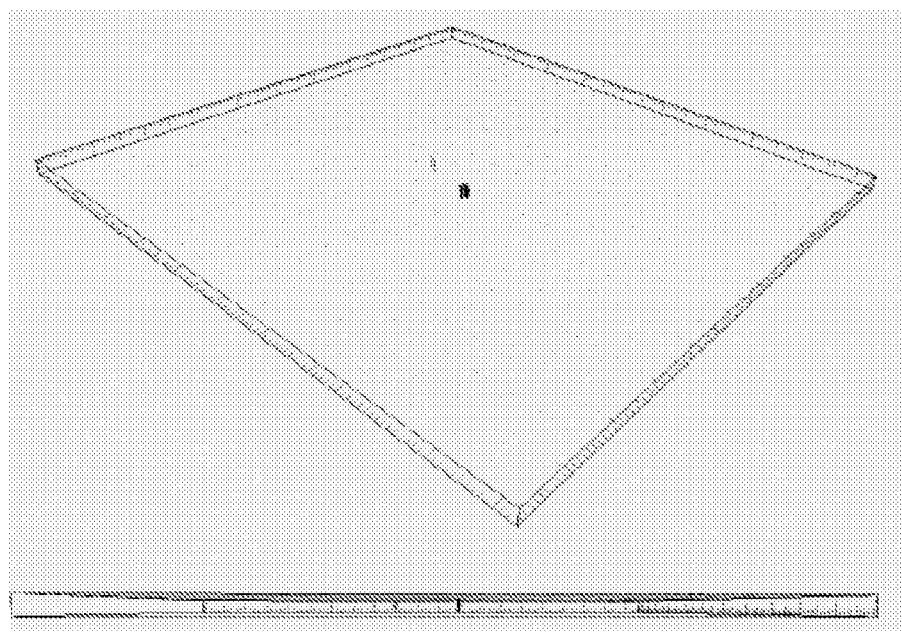

P. aeruginosa PAO1 ($5 \times 10^5$ cfu/mL) was grown in MHII media in an MBEC plate for 20 hours either alone or in the presence of 5 µM of the indicated PPMOs, PMBN alone, (RXR)$_4$, or a scrambled PPMO. All conditions contained 2 µg/mL of PMBN unless indicated otherwise. Pegs were processed for crystal violet or visualized by microscopy at 20 hours. FIG. 6A: Crystal violet analysis of 20 hour biofilms showed statistically significant prevention of biofilm with RpsJ (PPMO #14), RpmB (PPMO #5) and LpxC (PPMO #2) PPMOs at 5 µM concentrations (one-way ANOVA p<0.0001. *Statistically significant difference from No PPMO, Scr #1, Peptide, and Nonapeptide when analyzed by Tukey's Multiple comparisons test). FIGS. 6B-6D: Spinning Disk confocal microscopy images of 20 hour biofilm treated with (FIG. 6B) No PPMO, (FIG. 6C) 5 µM Scr #1, (FIG. 6D) 5 µM RpsJ PPMO #14. PAO1 GFP is shown in green and biofilm is shown in red. The biofilm is stained with 200 µg/mL of Concanavalin A, Alexafluor 647 conjugate.

Example 6

PPMO Treatment Diminishes Existing P. aeruginosa Biofilm

Figure 7A:
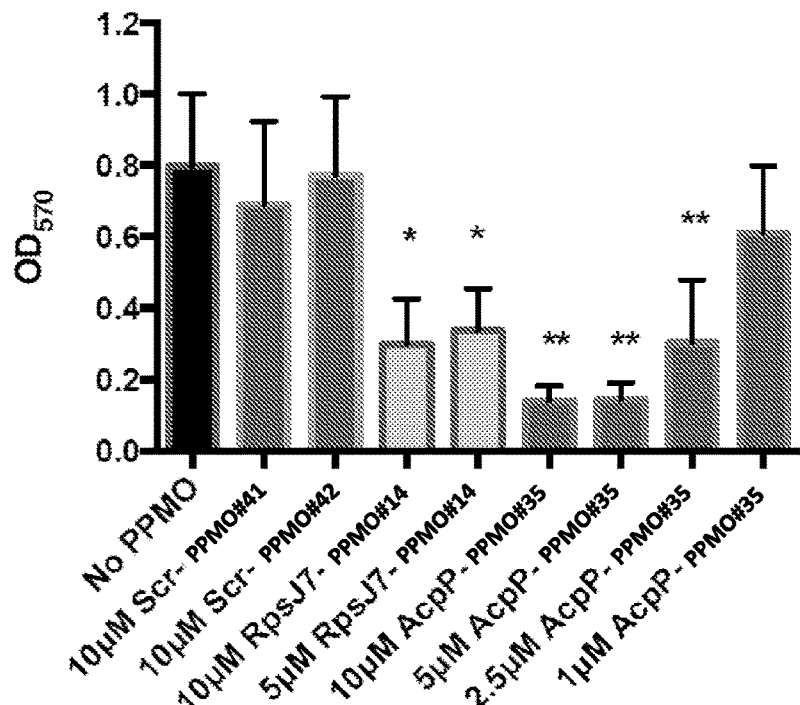
FIG. 7A: Crystal violet analysis of 48 hour biofilms showed statistically significant reduction of biofilm with RpsJ (PPMO #14) at 10 and 5 µM, and with AcpP PPMO #35 at 10, 5, 2.5, and 1 µM (one-way ANOVA p<0.0001. *Statistically significant difference from No PPMO and Scr PPMO #41, ** Statistically significant difference from No PPMO and Scr PPMO #42 when analyzed by Tukey's Multiple comparisons test).
Figure 7B:
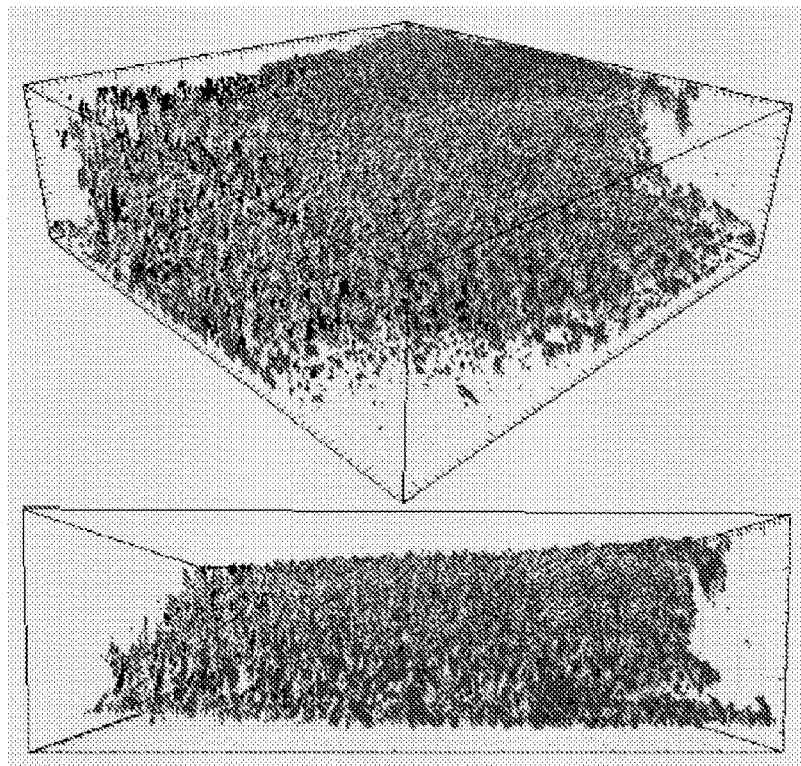
FIGS. 7B-7D: Spinning Disk confocal microscopy images of 48 hour biofilm treated with (FIG. 7B) 10 µM Scr PPMO #42, (FIG. 7C) 2.5 µM AcpP PPMO #35, (FIG. 7D) 10 µM AcpP PPMO #35. Green channel is PAO1 GFP; Red channel is biofilm stained with 200 µg/mL of Concanavalin A, Alexafluor 647 conjugate.
Figure 7C:
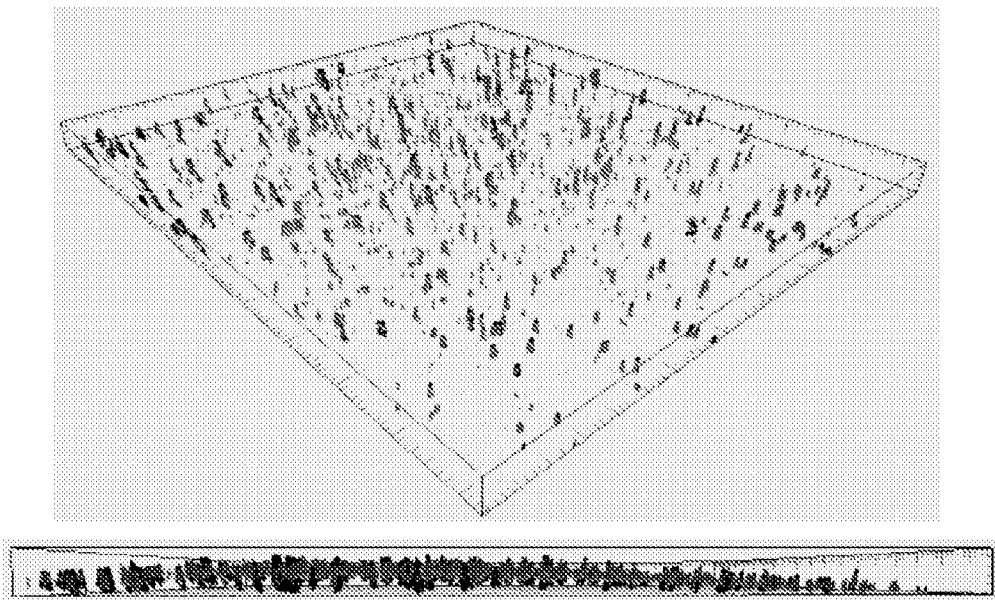
Figure 7D:
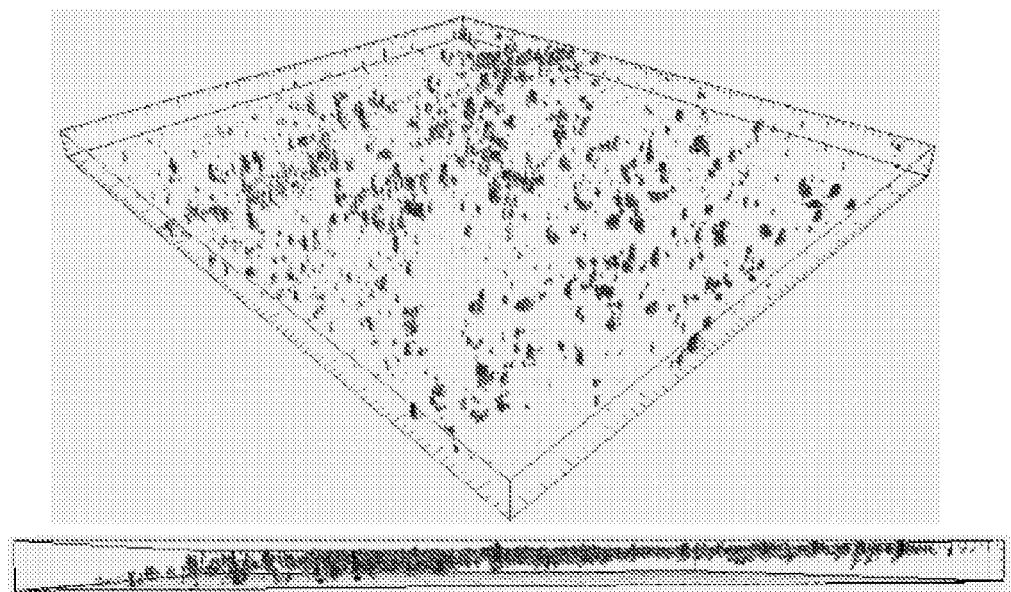

P. aeruginosa PAO1 ($5 \times 10^5$ cfu/mL) was grown in an MBEC plate for 24 hours. At 24 hours, the pegs were moved to a new 96-well plate containing fresh MHII media and either scrambled, RpsJ, or AcpP PPMO at the indicated concentrations. All wells containing PPMOs (including Scrambled) contained 2 µg/mL of PMBN. The pegs were again moved to new plates with or without PPMOs at 32 and 40 hours. Pegs were processed for crystal violet or visualized with microscopy at 48 hours. FIG. 7A: Crystal violet analysis of 48 hour biofilms showed statistically significant reduction of biofilm with RpsJ (PPMO #14) at 10 and 5 µM, and with AcpP PPMO #35 at 10, 5, 2.5, and 1 µM (one-way ANOVA p<0.0001. *Statistically significant difference from No PPMO and Scr #1 (PPMO #41),  Statistically significant difference from No PPMO and Scr #2 (PPMO #42) when analyzed by Tukey's Multiple comparisons test). FIGS. 7B-7D: Spinning Disk confocal microscopy images of 48 hour biofilm treated with (FIG. 7B) 10 µM Scr #2, (FIG. 7C) 2.5 µM AcpP PPMO, (FIG. 7D**) 10 µM AcpP PPMO. Green channel is PAO1 GFP; Red channel is biofilm stained with 200 µg/mL of Concanavalin A, Alexafluor 647 conjugate.

Example 7

AcpP PPMO #35 is Synergistic with Piperacillin Tazobactam

Figure 8:
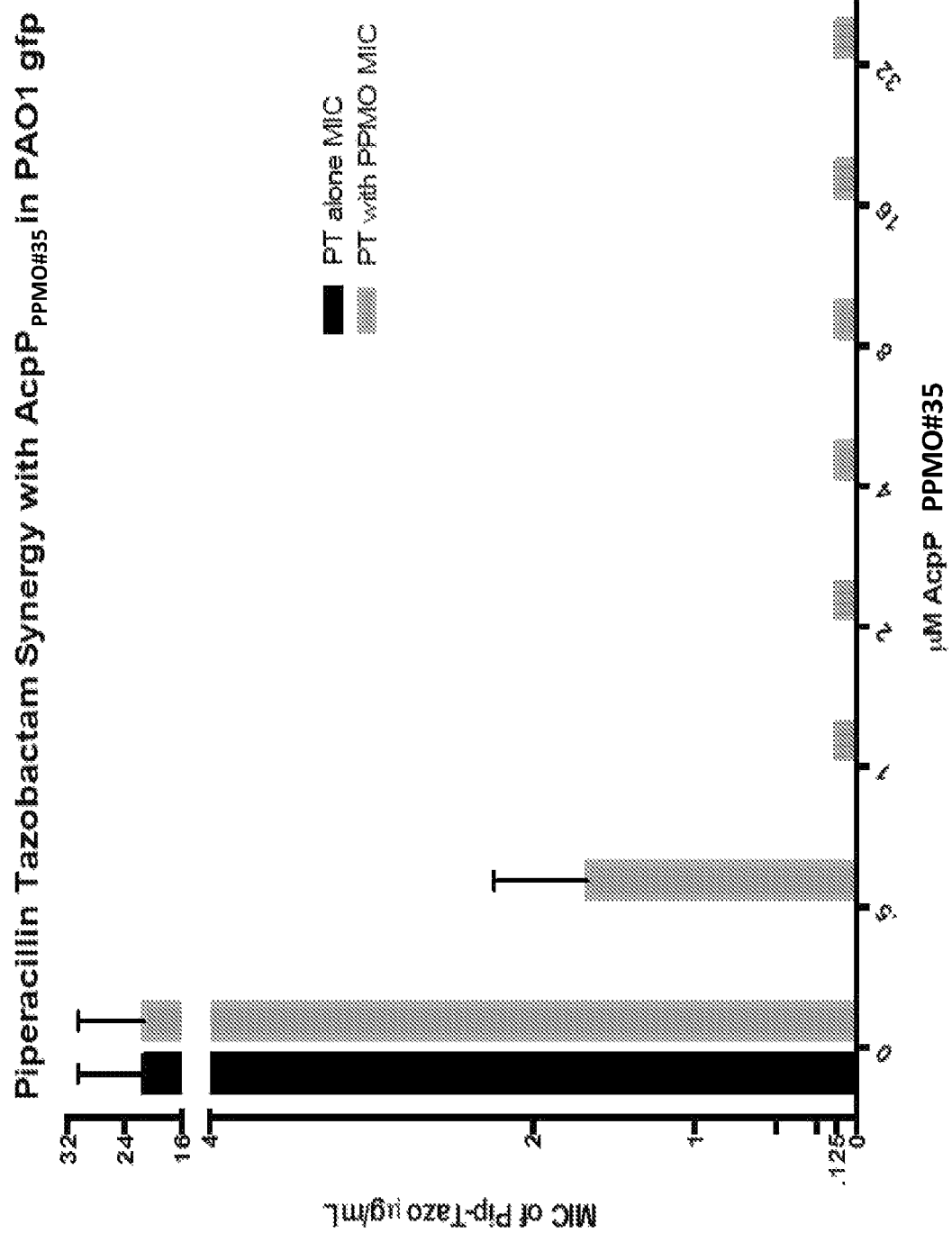
FIG. 8 shows AcpP PPMO #35 is synergistic with Piperacillin Tazobactam. A synergy assay was performed with Piperacillin Tazobactam and AcpP PPMO #35 in *P. aeruginosa* PAO1. $1 \times 10^6$ cfu/mL of PAO1 was inoculated into Mueller Hinton II media in an 96-well plate in the presence of 2 µs/mL PMBN. Piperacillin Tazobactam (PT) was serial diluted by half dilutions in the lateral direction from 128 to 0.124 µg/mL. AcpP PPMO #35 was vertically diluted in the same manner from 32 to 0.5 µM. The 96-well plate was then incubated for 18 hours at 37° C. The graph shows the MIC of PT alone versus PT with increasing concentrations of AcpP PPMO #35. The PT with AcpP PPMO #35 combination showed decreasing MIC values as the PPMO concentration increased.

A synergy assay was performed with Piperacillin Tazobactam and AcpP PPMO #35 in *P. aeruginosa* PAO1. 1×10$^6$ cfu/mL of PAO1 was inoculated into Mueller Hinton II media in an 96-well plate in the presence of 2 µg/mL PMBN. Piperacillin Tazobactam (PT) was serial diluted by half dilutions in the lateral direction from 128 to 0.124 µg/mL. AcpP PPMO #35 was vertically diluted in the same manner from 32 to 0.5 µM. The 96-well plate was then incubated for 18 hours at 37° C. FIG. 8 shows the MIC of PT alone versus PT with increasing concentrations of AcpP PPMO #35. The PT with AcpP PPMO #35 combination showed decreasing MIC values as the PPMO concentration increased.

Example 8

An AmpR PPMO Restores Activity of Ampicillin in *P. aeruginosa* PAO1

Figure 9:
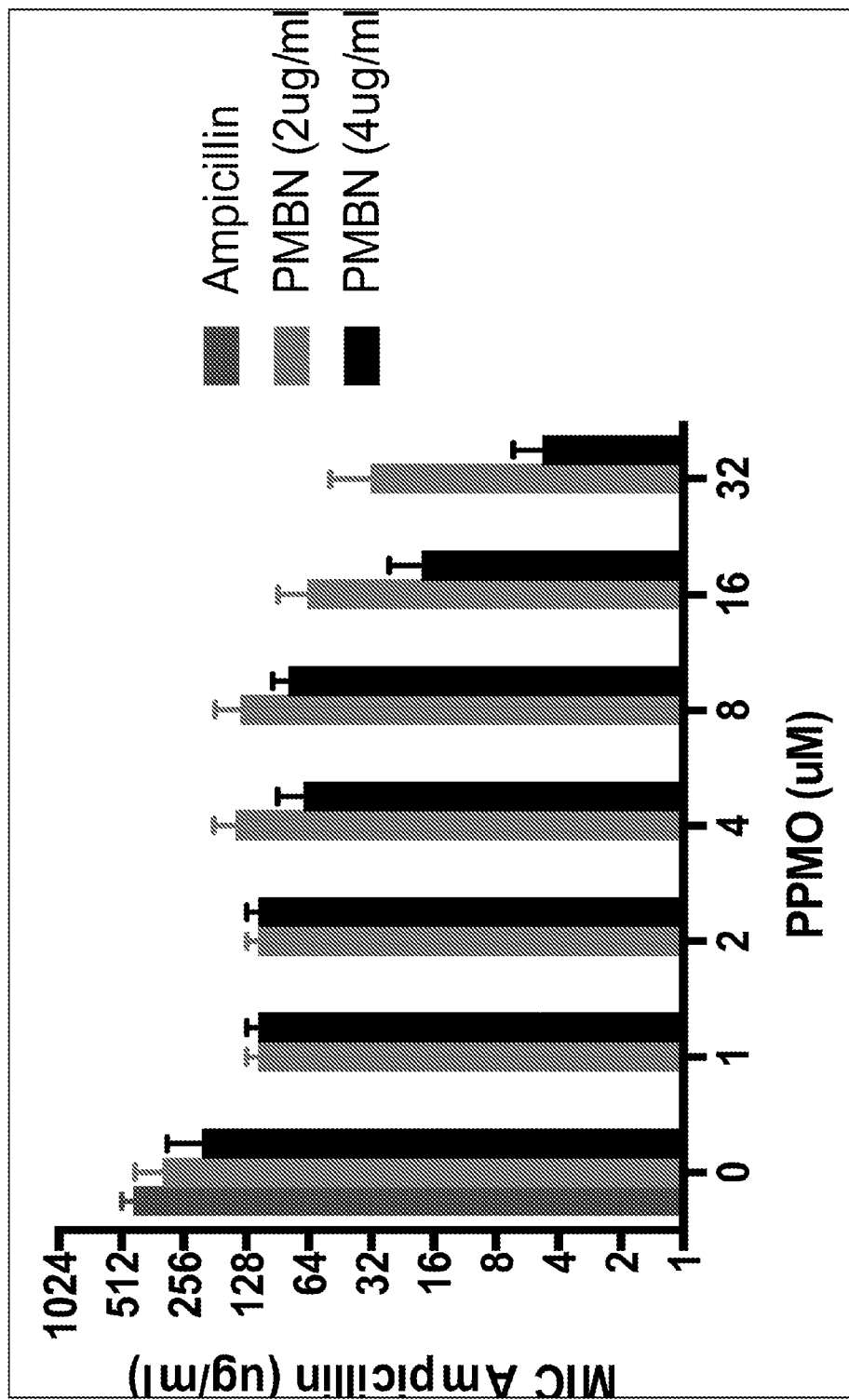
FIG. 9 shows the minimal inhibitory concentration (MIC) of Ampicillin as a function of AmpR PPMO and PMBN concentration. An AmpR PPMO combined with PMBN restores activity of Ampicillin in *P. aeruginosa* PAO1.

The ability to use PPMOs as adjunctive therapeutics to restore antibiotic sensitivity to existing drugs could be an intriguing way to explore treatment of multidrug-resistant pathogens that are increasingly being found in chronically infected patients. Frequently encountered resistance genes (β-lactamases, efflux pumps) were targeted. Proof of principle studies demonstrate that this could be a viable approach that is worthy of further animal study. An exemplary PPMO, as set forth in Table 5 and illustrated below, was designed to target AmpR in *P. aeruginosa*, a global transcriptional regulator that regulates β-lactamases such as AmpC. FIG. 9 demonstrates that an AmpR PPMO (PPMO #28) combined with PMBN restores activity of the antibiotic ampicillin. As the concentration of PPMO increased, the MIC of Ampicillin progressively decreased from an MIC of 512 µg/ml in the absence of PPMO down to an MIC of 4 µg/ml in the presence of 32 µM AmpR PPMO and 4 µg/ml PMBN. Testing the AmpR PPMO in animal models would be a reasonable alternative approach to thinking of antisense as adjuvant therapy with traditional antibiotics.

TABLE 5

Exemplary AmpR PPMO Compound

| PPMO Name | Target Gene | Targeting Sequence (TS)* | TS SEQ ID NO: | 5' CPP/ Linker | 3' | CPP SEQ ID NO: |
|---|---|---|---|---|---|---|
| PPMO #28 | ampR | GTCGAAC CAAT | 22 | (RXR)4XB | COCH3 | 23 |

*The thymines (T) can be uracils (U), and vice versa

Exemplary structure of PPMO #28:

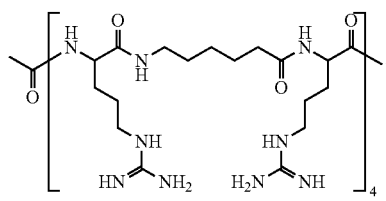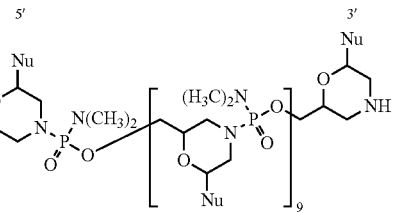

wherein the targeting sequence is GTC GAA CCA AT (SEQ ID NO: 22), wherein thymine bases may be uracil bases.

In some embodiments, the thymine bases of the targeting sequence of Table 5 and/or the targeting sequence of the above structure are uracil bases.

The invention claimed is:

1. A compound of the formula:

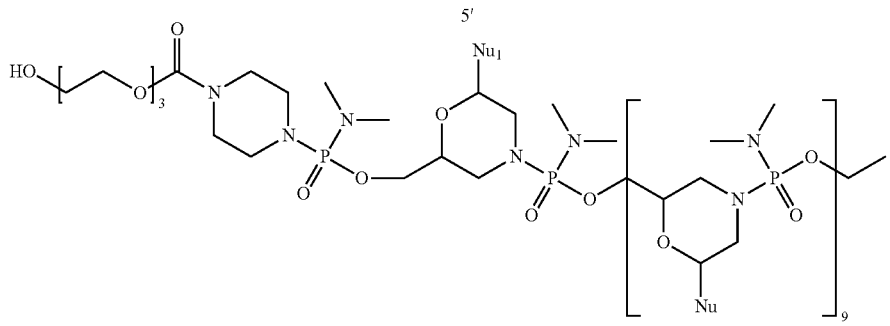

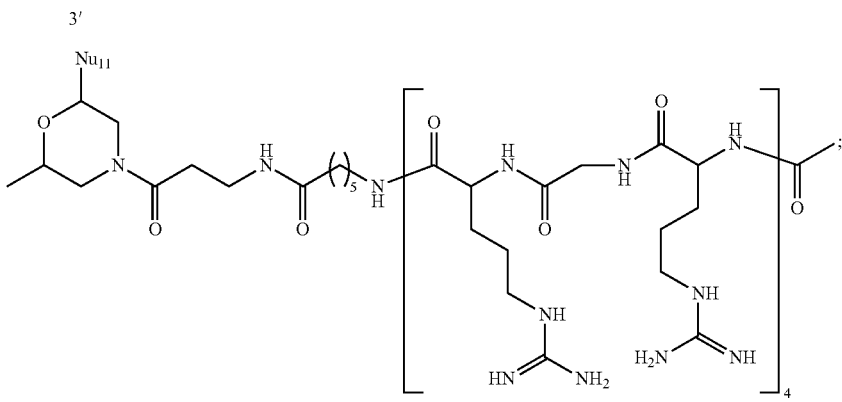

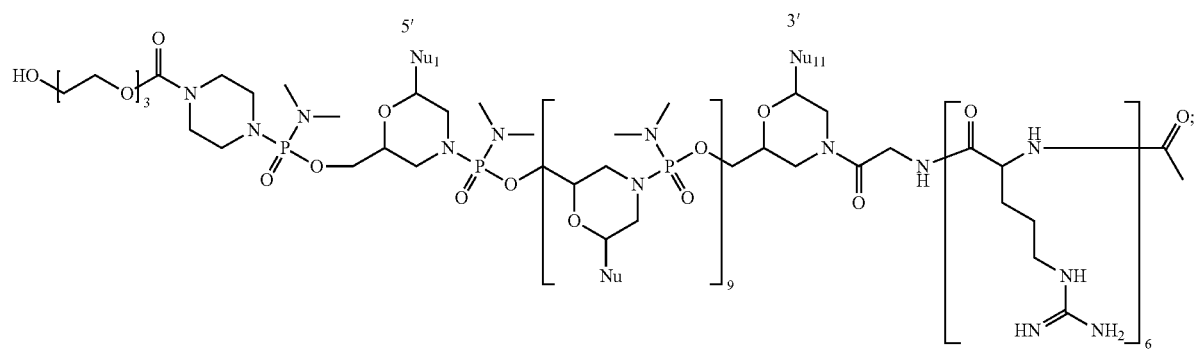
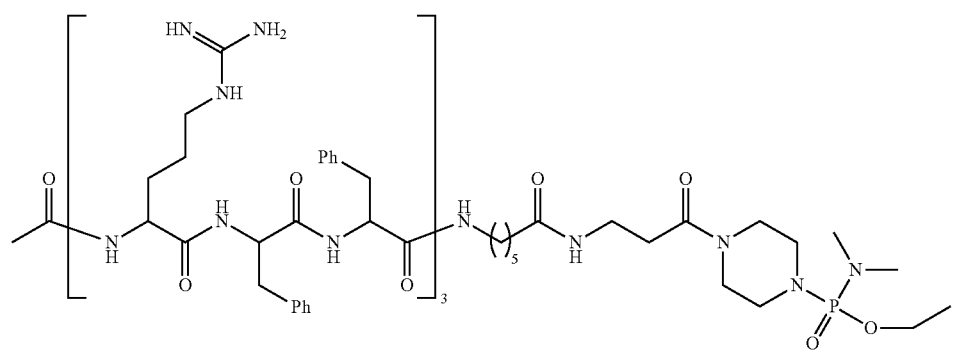
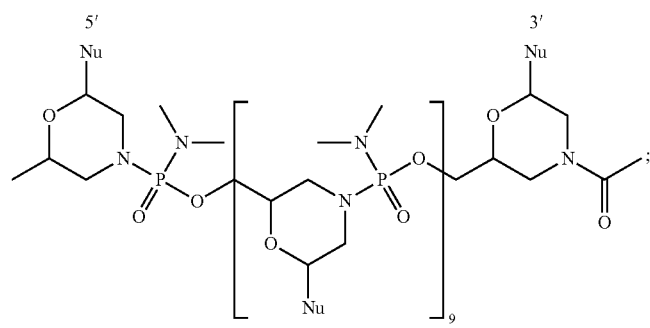
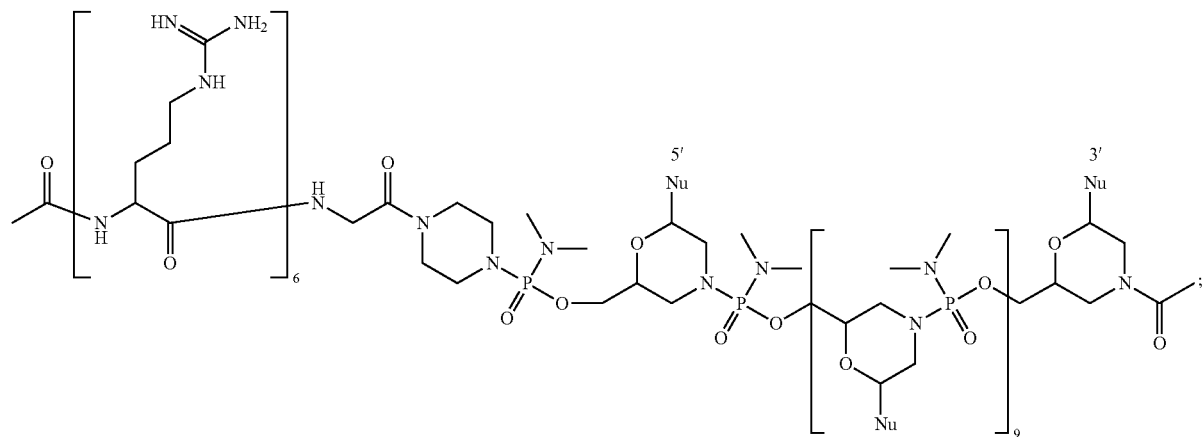

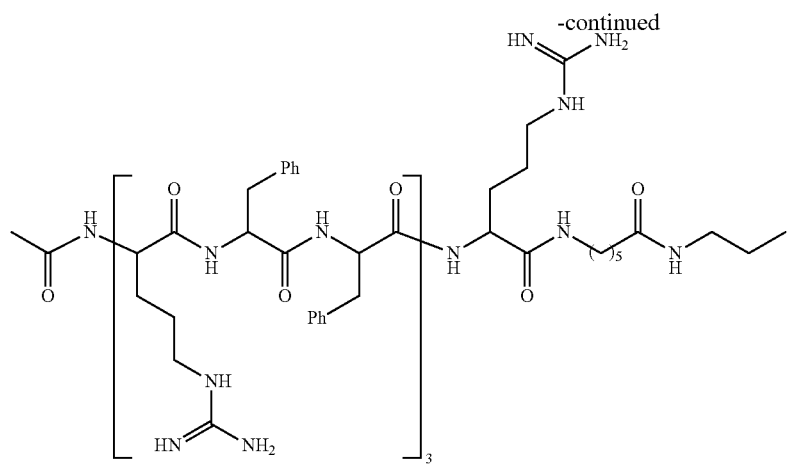

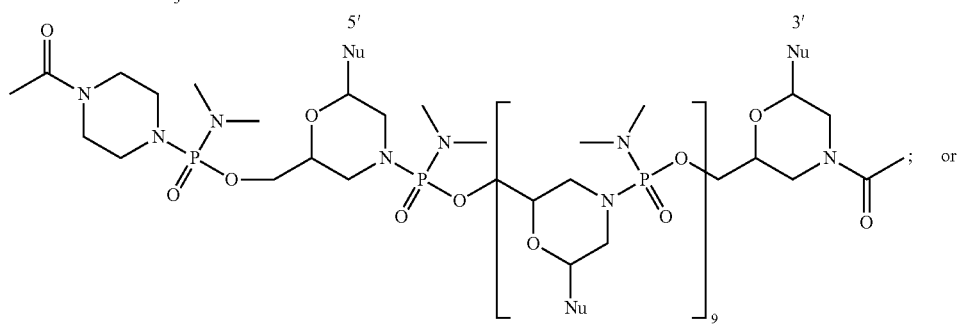

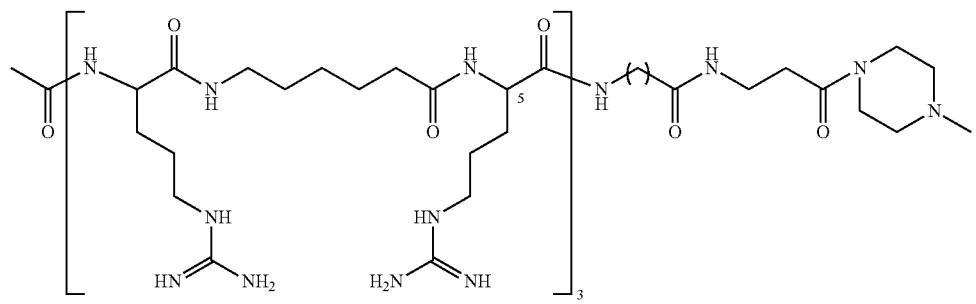

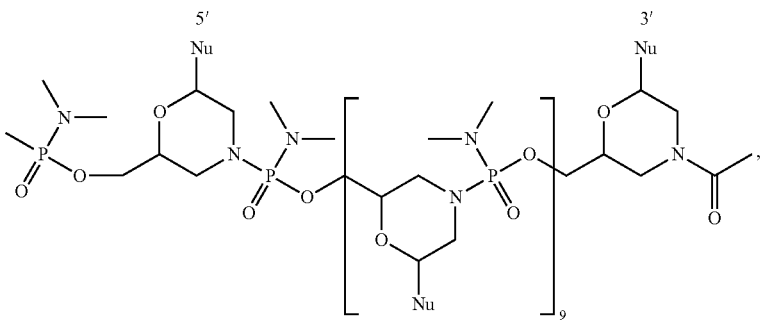

or a pharmaceutically acceptable salt thereof, wherein:

each Nu is a nucleobase which taken together forms a nucleobase sequence;

wherein the nucleobase sequence comprises a targeting sequence having a sequence, from 5' to 3', of CCT CAG ACT CC (SEQ ID NO: 1), GTC GAA CCA AT (SEQ ID NO: 22), or wherein the nucleobase sequence consists of a sequence from 5'to 340, of GTT GTT TGA TC (SEQ ID NO: 2), wherein thymine bases may be uracil bases.

2. The compound of claim 1, wherein the compound is selected from:

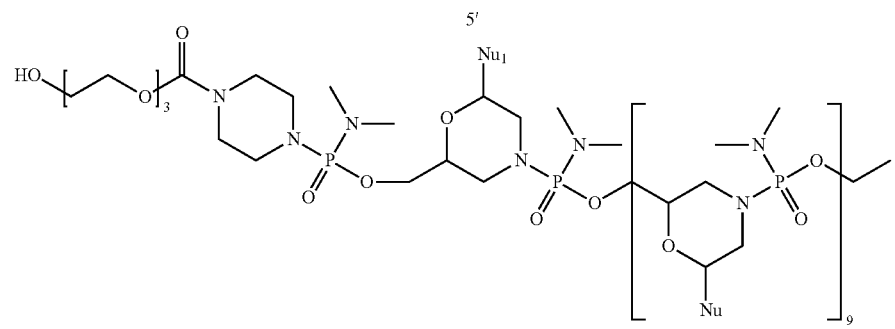
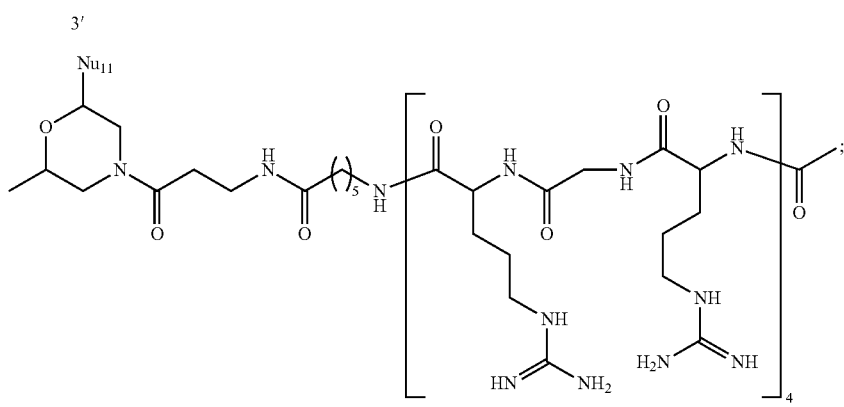
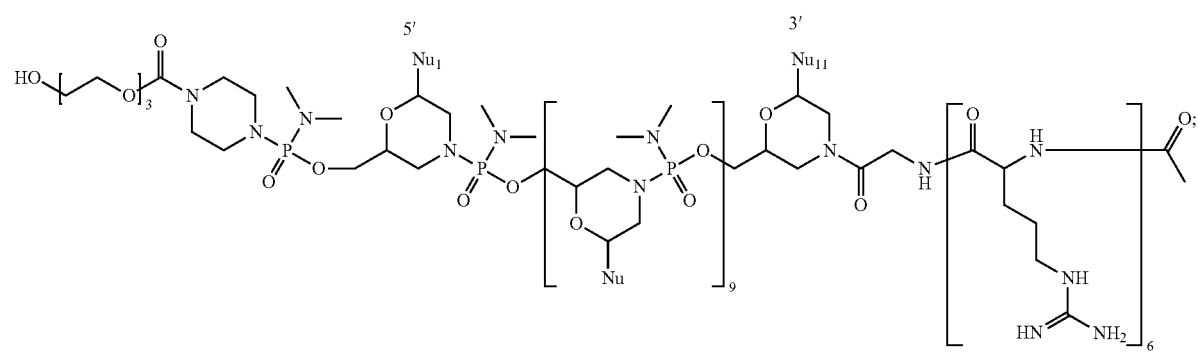
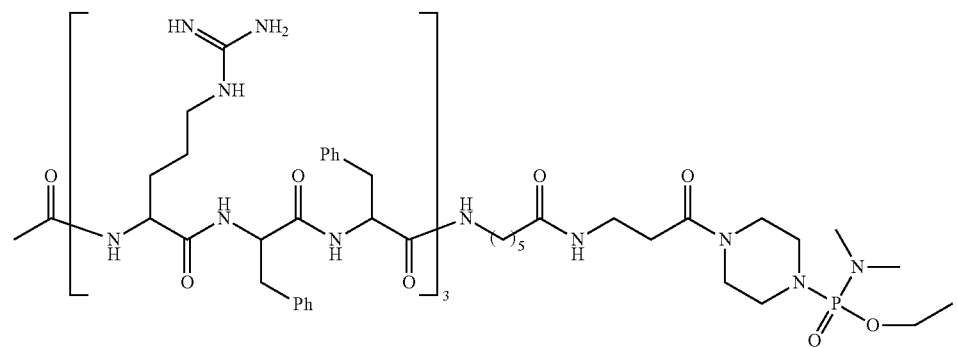

-continued
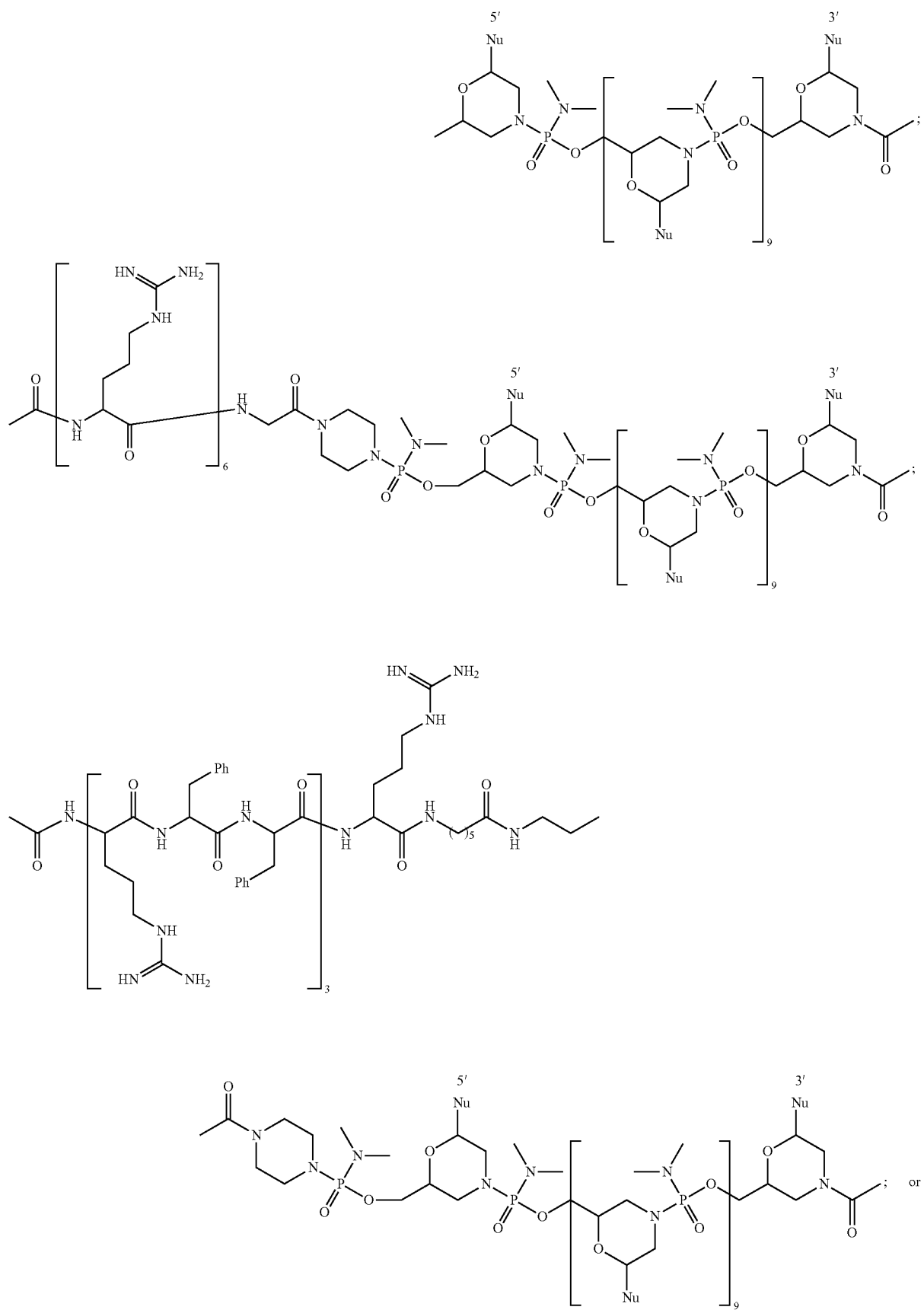

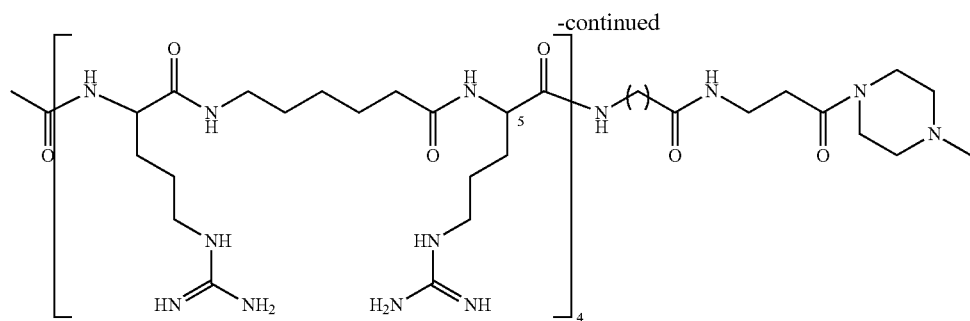
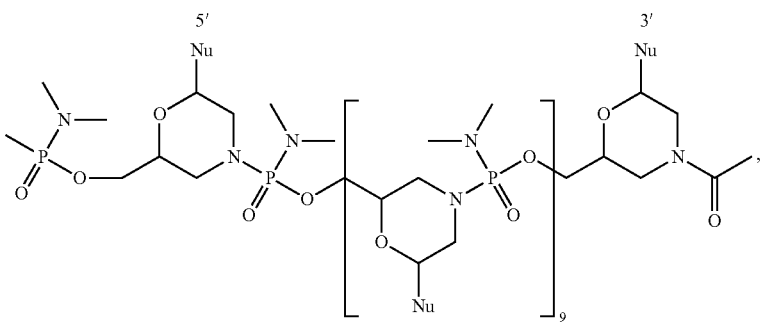
or a pharmaceutically acceptable salt thereof,
wherein the targeting sequence, from 5' to 3', is CCT CAG ACT CC (SEQ ID NO: 1),
wherein thymine bases may be uracil bases.
3. The compound of claim 1, wherein the compound is of the formula:
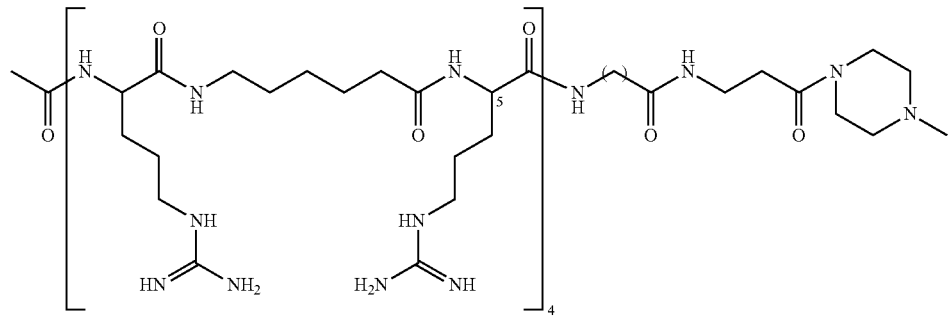
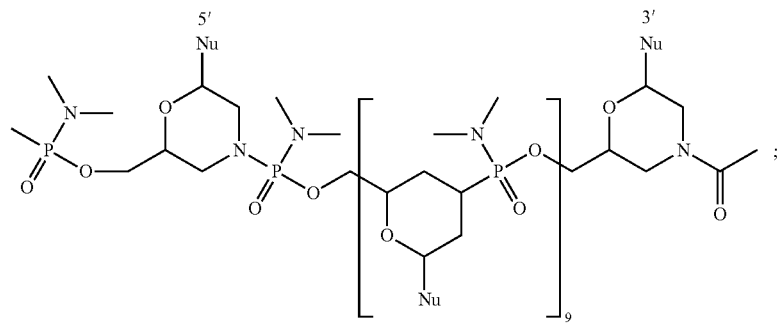

103
104
-continued
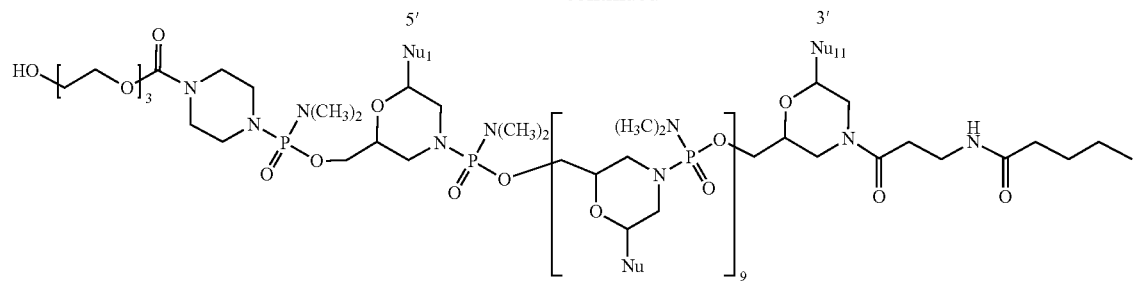
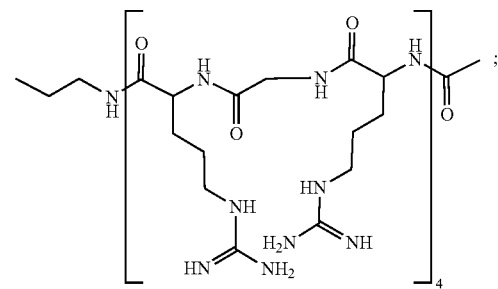
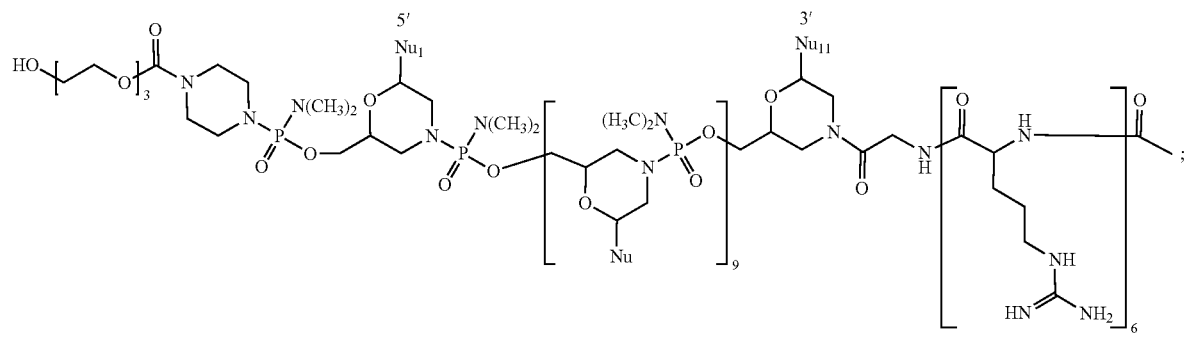
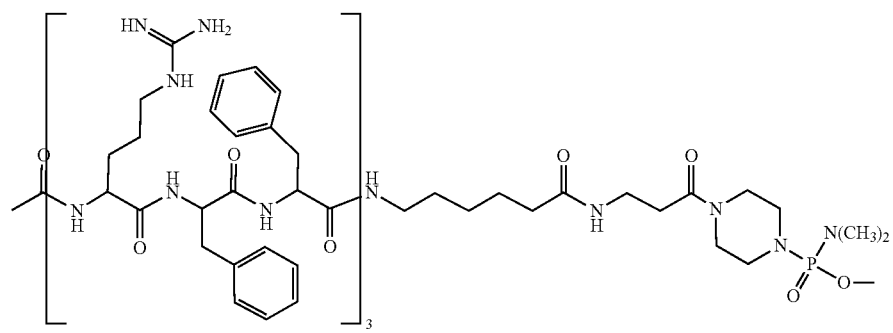
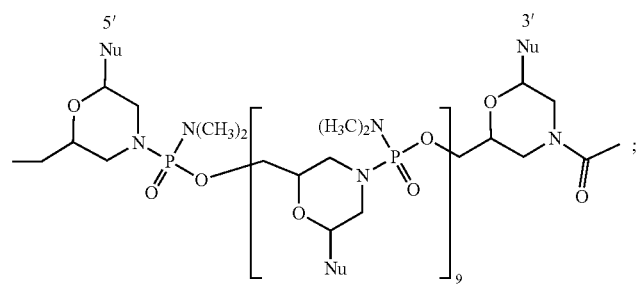

-continued

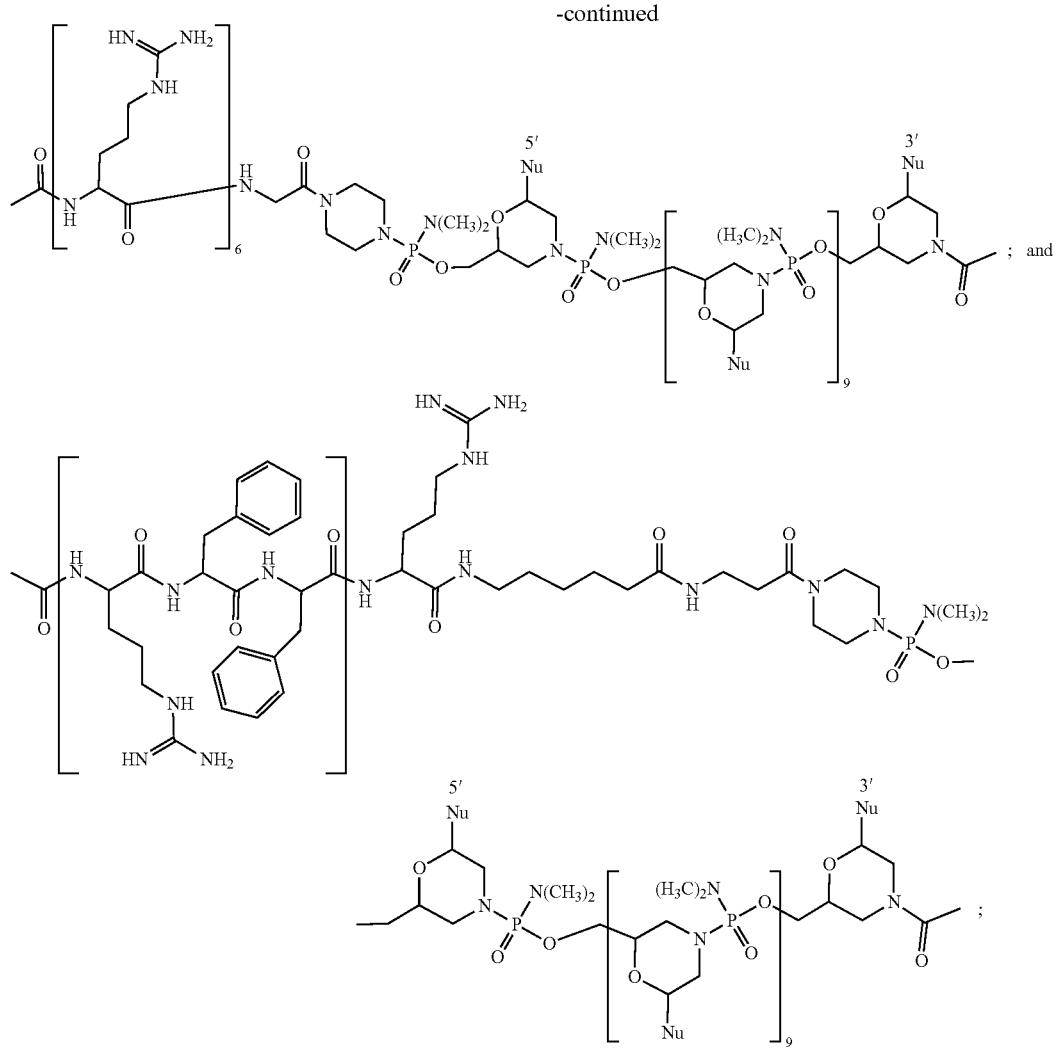

wherein the targeting sequence, from 5' to 3', is GTC GAA CCA AT (SEQ ID NO: 22), wherein thymine bases may be uracil bases.

4. A combination, comprising:
   a) the compound according to claim 1, or a pharmaceutically acceptable salt thereof; and
   b) a second compound selected from the group consisting of polymyxin E (PME), polymyxin B (PMB), polymyxin B nonapeptide (PMBN), polymyxin E nonapeptide, a pharmaceutically acceptable salt of any of the foregoing, and combinations thereof.

5. The combination of claim 4, wherein the second compound is PME.

6. The combination of claim 4, wherein the second compound is PMBN.

7. The compound of claim 1, wherein the compound is selected from:

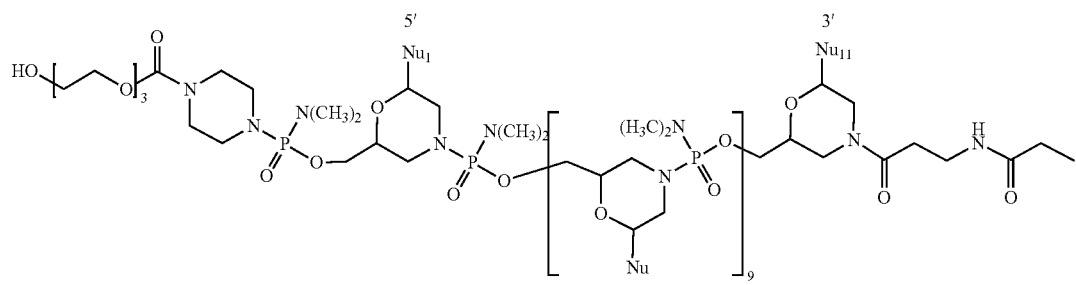

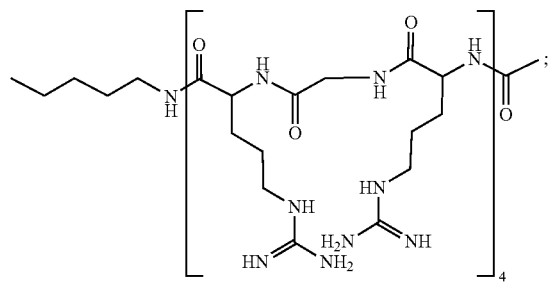
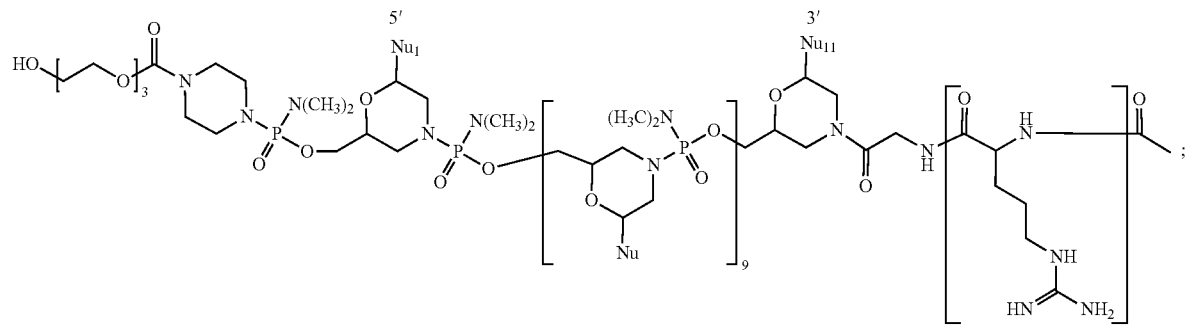
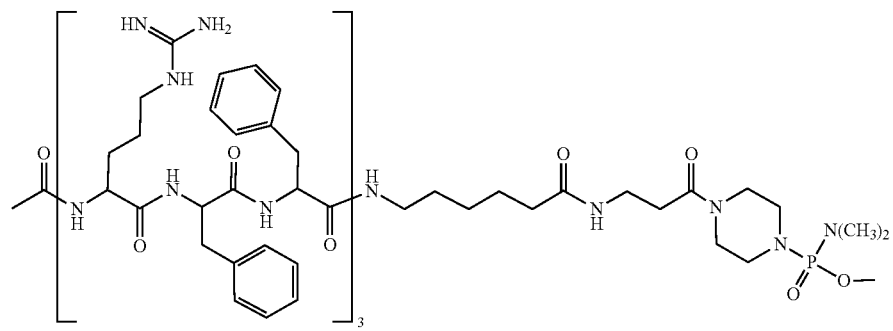
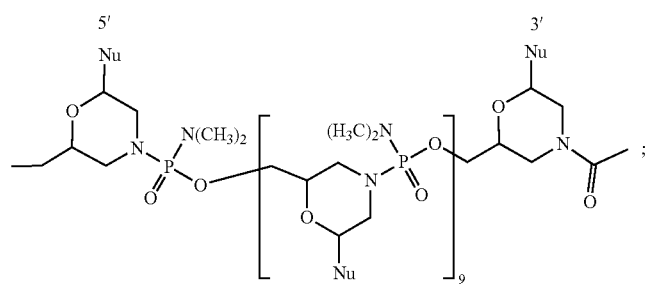
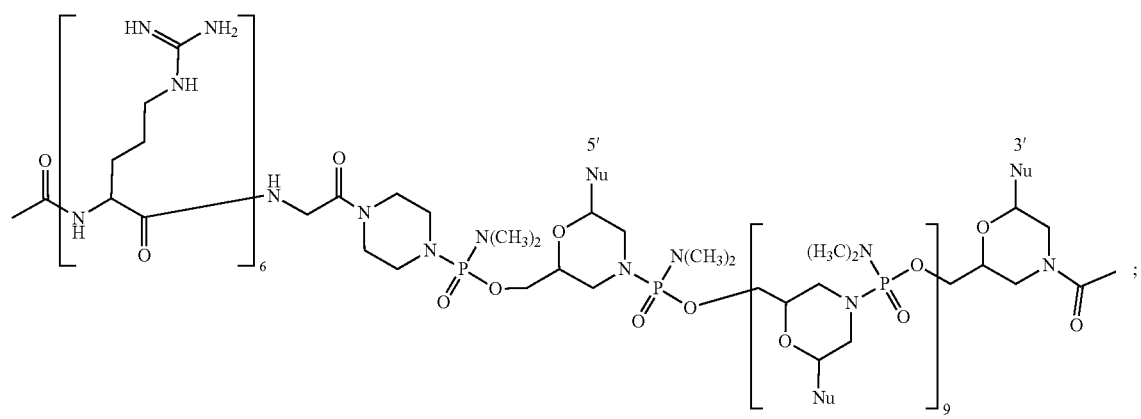

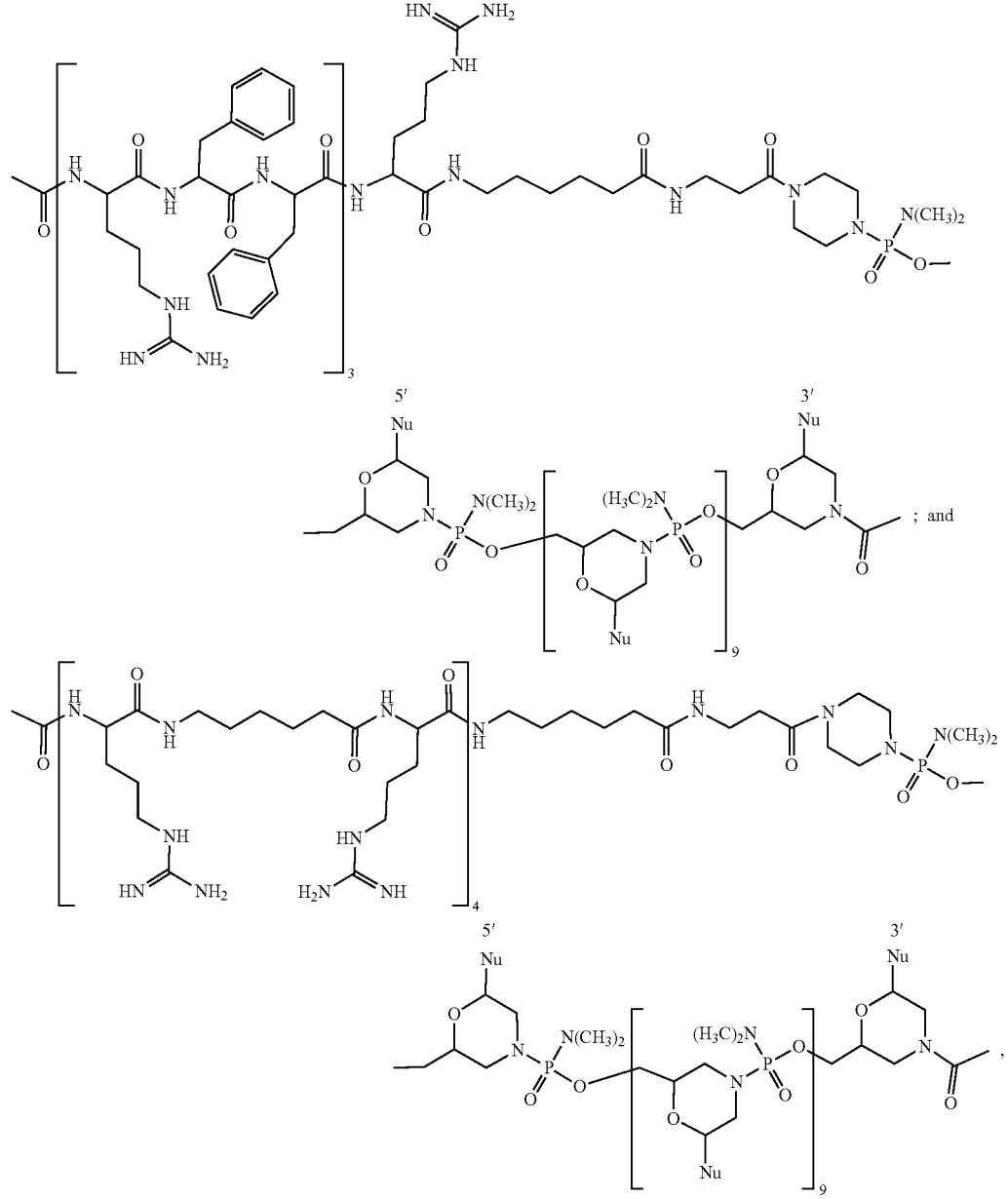
or a pharmaceutically acceptable salt thereof,
wherein the targeting sequence, from 5' to 3', consists of GTT GTT TGA TC (SEQ ID NO: 2), wherein thymine bases may be uracil bases.
* * * * *

UNITED STATES PATENT AND TRADEMARK OFFICE
CERTIFICATE OF CORRECTION

| | |
|---|---|
| PATENT NO. | : 11,293,024 B2 |
| APPLICATION NO. | : 15/540387 |
| DATED | : April 5, 2022 |
| INVENTOR(S) | : Bruce L. Geller et al. |

It is certified that error appears in the above-identified patent and that said Letters Patent is hereby corrected as shown below:

In the Specification

In Column 1, Line 26, insert:
--STATEMENT REGARDING FEDERALLY SPONSORED RESEARCH OR DEVELOPMENT
This invention was made with government support under grant number AI 105980 awarded by National Institutes of Health. The government has certain rights in the invention.--.

Signed and Sealed this
Second Day of August, 2022

Katherine Kelly Vidal
*Director of the United States Patent and Trademark Office*